United States Patent
Lattner et al.

(10) Patent No.: US 8,076,524 B2
(45) Date of Patent: Dec. 13, 2011

(54) PROCESS FOR GENERATING ALPHA OLEFIN COMONOMERS

(75) Inventors: James R. Lattner, Laporte, TX (US); John F. Walzer, Jr., Seabrook, TX (US); Krishnan Sankaranarayanan, South Riding, VA (US); John Scott Buchanan, Lambertville, NJ (US); Milind Bholanath Ajinkya, Oakton, VA (US); Stephen M Wood, Beaumont, TX (US); Anastasios I Skoulidas, Bristow, VA (US); Jay L Reimers, Geismar, LA (US); Timothy Daniel Shaffer, Hackettstown, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 948 days.

(21) Appl. No.: 11/654,187

(22) Filed: Jan. 17, 2007

(65) Prior Publication Data
US 2007/0185362 A1   Aug. 9, 2007

Related U.S. Application Data

(63) Continuation-in-part of application No. 11/518,456, filed on Sep. 8, 2006, and a continuation-in-part of application No. 11/517,871, filed on Sep. 8, 2006, which is a continuation-in-part of application No. 11/346,651, filed on Feb. 3, 2006, and a continuation-in-part of application No. 11/346,652, filed on Feb. 3, 2006.

(60) Provisional application No. 60/873,162, filed on Dec. 6, 2006, provisional application No. 60/873,221, filed on Dec. 6, 2006, provisional application No. 60/841,226, filed on Aug. 30, 2006.

(51) Int. Cl.
*C07C 2/22* (2006.01)

(52) U.S. Cl. ........ 585/513; 585/502; 585/510; 585/511; 585/512; 585/520; 585/521; 585/522; 585/523

(58) Field of Classification Search .................. 585/512, 585/513, 517, 521, 522, 523, 502, 510, 511, 585/520
See application file for complete search history.

(56) References Cited

U.S. PATENT DOCUMENTS 3,300,458 A   1/1967   Manyik et al.
(Continued)

FOREIGN PATENT DOCUMENTS

CA   2087578   7/1994
(Continued)

OTHER PUBLICATIONS

Agrawal, "More Operable Fully Thermally Coupled Distillation Column Configurations for Multicomponent Distillation", Trans. I. Chem. E., 77(A), 543-553 (1999).*

(Continued)

*Primary Examiner* — In Suk Bullock
*Assistant Examiner* — Bradley Etherton
(74) *Attorney, Agent, or Firm* — Frank E. Reid; Robert L. Abdon

(57) ABSTRACT

The present invention relates to a method for preparing olefin comonomers from ethylene. The comonomer generated can be used in a subsequent process, such as a polyethylene polymerization reactor. The comonomer generated can be transported, optionally without isolation or storage, to a polyethylene polymerization reactor. One method includes the steps of: feeding ethylene and a catalyst in a solvent/diluent to one or more comonomer synthesis reactors; reacting the ethylene and the catalyst under reaction conditions sufficient to produce an effluent comprising a desired comonomer; forming a gas stream comprising unreacted ethylene, and a liquid/bottoms stream comprising the comonomer, optionally by passing the effluent to one or more downstream gas/liquid phase separators; and purifying at least a portion of said liquid/bottoms stream by removing at least one of solid polymer, catalyst, and undesirable olefins therefrom.

46 Claims, 20 Drawing Sheets

Flow diagram for the ethylene trimerization reactor system using evaporative cooling.

U.S. PATENT DOCUMENTS

| | | | |
|---|---|---|---|
| 3,333,016 A | 7/1967 | Schultz | |
| 4,472,525 A | 9/1984 | Singleton | |
| 4,511,746 A | 4/1985 | Miller | |
| 4,668,838 A | 5/1987 | Briggs | |
| 4,689,437 A | 8/1987 | Murray | |
| 4,777,315 A | 10/1988 | Levine et al. | |
| 4,853,356 A | 8/1989 | Briggs | |
| 5,000,840 A | 3/1991 | Anthes et al. | |
| 5,137,994 A | 8/1992 | Goode et al. | |
| 5,198,563 A | 3/1993 | Reagen et al. | |
| 5,376,612 A | 12/1994 | Reagen et al. | |
| 5,382,738 A | 1/1995 | Reagen et al. | |
| 5,438,027 A | 8/1995 | Reagen et al. | |
| 5,439,862 A | 8/1995 | Kemp | |
| 5,451,645 A | 9/1995 | Reagen et al. | |
| 5,491,272 A | 2/1996 | Tanaka et al. | |
| 5,523,507 A | 6/1996 | Reagen et al. | |
| 5,541,270 A | 7/1996 | Chinh et al. | |
| 5,543,375 A | 8/1996 | Lashier et al. | |
| 5,550,305 A | 8/1996 | Wu | |
| 5,557,026 A | 9/1996 | Tanaka et al. | |
| 5,563,312 A | 10/1996 | Knudsen et al. | |
| 5,637,660 A | 6/1997 | Nagy et al. | |
| 5,668,249 A | 9/1997 | Baardman et al. | |
| 5,731,487 A | 3/1998 | Tamura et al. | |
| 5,744,677 A | 4/1998 | Wu | |
| 5,750,813 A * | 5/1998 | Hess et al. | 585/12 |
| 5,750,816 A | 5/1998 | Araki et al. | |
| 5,750,817 A | 5/1998 | Tanaka et al. | |
| 5,763,723 A | 6/1998 | Reagen et al. | |
| 5,811,618 A | 9/1998 | Wu | |
| 5,814,575 A | 9/1998 | Reagen et al. | |
| 5,853,551 A | 12/1998 | Boucot et al. | |
| 5,856,257 A | 1/1999 | Freeman et al. | |
| 5,856,610 A | 1/1999 | Tamura et al. | |
| 5,856,612 A * | 1/1999 | Araki et al. | 585/522 |
| 5,859,303 A | 1/1999 | Lashier | |
| 5,910,619 A | 6/1999 | Urata et al. | |
| 5,919,996 A | 7/1999 | Freeman et al. | |
| 5,968,866 A | 10/1999 | Wu | |
| 6,004,256 A | 12/1999 | Townsend et al. | |
| 6,031,145 A | 2/2000 | Commereuc et al. | |
| 6,103,657 A | 8/2000 | Murray | |
| 6,133,495 A | 10/2000 | Urata et al. | |
| 6,136,748 A | 10/2000 | Smith | |
| 6,137,748 A | 10/2000 | Murakami | |
| 6,265,513 B1 | 7/2001 | Murray et al. | |
| 6,268,447 B1 | 7/2001 | Murray et al. | |
| 6,274,783 B1 | 8/2001 | Gildert et al. | |
| 6,277,841 B1 | 8/2001 | Rajagopalan et al. | |
| 6,303,719 B1 | 10/2001 | Murray et al. | |
| 6,320,002 B1 | 11/2001 | Murray et al. | |
| 6,320,005 B1 | 11/2001 | Murray | |
| 6,337,297 B1 | 1/2002 | Mimura et al. | |
| 6,344,594 B1 | 2/2002 | Sen et al. | |
| 6,380,451 B1 | 4/2002 | Kreischer et al. | |
| 6,399,843 B1 | 6/2002 | Koves | |
| 6,423,791 B1 | 7/2002 | Kral | |
| 6,437,161 B1 | 8/2002 | Mihan et al. | |
| 6,455,648 B1 | 9/2002 | Freeman et al. | |
| 6,489,263 B2 | 12/2002 | Murray et al. | |
| 6,521,806 B1 | 2/2003 | Tamura et al. | |
| 6,559,091 B1 | 5/2003 | Moody et al. | |
| 6,583,083 B2 | 6/2003 | Murray et al. | |
| 6,610,627 B2 | 8/2003 | Murray | |
| 6,610,805 B1 | 8/2003 | Guram et al. | |
| 6,706,829 B2 | 3/2004 | Boussie et al. | |
| 6,713,577 B2 * | 3/2004 | Boussie et al. | 526/161 |
| 6,727,361 B2 | 4/2004 | LaPointe et al. | |
| 6,750,345 B2 | 6/2004 | Boussie et al. | |
| 6,800,702 B2 * | 10/2004 | Wass | 526/124.3 |
| 6,828,269 B2 | 12/2004 | Commereuc et al. | |
| 6,828,397 B2 | 12/2004 | Boussie et al. | |
| 6,844,290 B1 | 1/2005 | Maas et al. | |
| 6,844,920 B2 | 1/2005 | Louellau | |
| 6,900,152 B2 | 5/2005 | Yoshida et al. | |
| 7,045,583 B2 | 5/2006 | Kuchta et al. | |
| 7,157,612 B2 | 1/2007 | Ewert et al. | |
| 7,214,842 B2 | 5/2007 | Mihan et al. | |
| 2001/0034297 A1 | 10/2001 | Murray et al. | |
| 2002/0035029 A1 | 3/2002 | Yoshida et al. | |
| 2002/0065379 A1 | 5/2002 | Murray | |
| 2002/0137845 A1 | 9/2002 | Boussie et al. | |
| 2002/0142912 A1 | 10/2002 | Boussie et al. | |
| 2002/0147288 A1 | 10/2002 | Boussie et al. | |
| 2002/0153697 A1 | 10/2002 | Amirola | |
| 2002/0156279 A1 | 10/2002 | Boussie et al. | |
| 2002/0173419 A1 | 11/2002 | Boussie et al. | |
| 2002/0177711 A1 | 11/2002 | LaPointe et al. | |
| 2002/0183574 A1 | 12/2002 | Dixon et al. | |
| 2003/0130551 A1 | 7/2003 | Drochon et al. | |
| 2003/0149198 A1 | 8/2003 | Small et al. | |
| 2003/0153697 A1 | 8/2003 | Boussie et al. | |
| 2003/0166456 A1 | 9/2003 | Wass | |
| 2004/0122247 A1 | 6/2004 | Boussie et al. | |
| 2004/0122271 A1 * | 6/2004 | Van Zon et al. | 585/530 |
| 2004/0228775 A1 * | 11/2004 | Ewert et al. | 422/131 |
| 2004/0236163 A1 | 11/2004 | Ewert et al. | |
| 2005/0020788 A1 | 1/2005 | Wass | |
| 2005/0020866 A1 | 1/2005 | Kobayashi et al. | |
| 2005/0113524 A1 | 5/2005 | Stevens et al. | |
| 2005/0197521 A1 | 9/2005 | Kreischer | |
| 2006/0094839 A1 | 5/2006 | Diamond et al. | |
| 2006/0094867 A1 | 5/2006 | Diamond et al. | |
| 2006/0173226 A1 | 8/2006 | Blann et al. | |
| 2006/0211903 A1 | 9/2006 | Blann et al. | |
| 2006/0229480 A1 | 10/2006 | Blann et al. | |
| 2006/0247339 A1 | 11/2006 | Harashina et al. | |
| 2006/0247399 A1 | 11/2006 | McConville et al. | |
| 2006/0247483 A1 | 11/2006 | McConville et al. | |
| 2006/0293546 A1 | 12/2006 | Nabika | |
| 2007/0027350 A1 | 2/2007 | Nabika | |
| 2007/0049781 A1 | 3/2007 | Brown et al. | |
| 2007/0185358 A1 | 8/2007 | Buchanan et al. | |
| 2007/0185360 A1 | 8/2007 | Buchanan et al. | |
| 2007/0185361 A1 | 8/2007 | Buchanan et al. | |
| 2007/0185362 A1 | 8/2007 | Lattner et al. | |
| 2007/0185364 A1 | 8/2007 | Buchanan et al. | |
| 2008/0058486 A1 | 3/2008 | McCullough et al. | |
| 2008/0182989 A1 | 7/2008 | Ackerman et al. | |
| 2008/0188633 A1 | 8/2008 | Ackerman et al. | |
| 2008/0200626 A1 | 8/2008 | Ackerman et al. | |
| 2008/0200743 A1 | 8/2008 | Ackerman et al. | |

FOREIGN PATENT DOCUMENTS

| | | |
|---|---|---|
| CA | 2115639 | 9/1994 |
| CN | 1256968 | 6/2000 |
| EP | 0 230 983 | 8/1987 |
| EP | 237 079 | 7/1990 |
| EP | 416 304 | 3/1991 |
| EP | 537 609 | 4/1993 |
| EP | 608 447 | 8/1994 |
| EP | 614 865 | 9/1994 |
| EP | 622 347 | 11/1994 |
| EP | 668 106 | 8/1995 |
| EP | 699 648 | 3/1996 |
| EP | 706 983 | 4/1996 |
| EP | 780 353 | 6/1997 |
| EP | 889 061 | 1/1999 |
| EP | 993 464 | 4/2000 |
| EP | 1 110 930 | 6/2001 |
| EP | 1 308 450 | 5/2003 |
| EP | 1 364 974 | 11/2003 |
| EP | 1 607 415 | 12/2005 |
| EP | 1607415 A1 * | 12/2005 |
| GB | 2 298 864 | 9/1996 |
| JP | 07010780 | 1/1995 |
| JP | 06515873 | 3/1995 |
| JP | 07215896 | 8/1995 |
| JP | 07267881 | 10/1995 |
| JP | 09020692 | 1/1997 |
| JP | 09020693 | 1/1997 |
| JP | 09268133 | 10/1997 |
| JP | 09268134 | 10/1997 |
| JP | 09268135 | 10/1997 |
| JP | 10-007712 | 1/1998 |
| JP | 10007593 | 1/1998 |

| | | |
|---|---|---|
| JP | 10007594 | 1/1998 |
| JP | 10007595 | 1/1998 |
| JP | 10036431 | 2/1998 |
| JP | 10036432 | 2/1998 |
| JP | 10045638 | 2/1998 |
| JP | 10087518 | 4/1998 |
| JP | 11092407 | 4/1999 |
| JP | 11092408 | 4/1999 |
| JP | 11222445 | 8/1999 |
| JP | 10007712 | 1/2000 |
| JP | 2000176291 | 6/2000 |
| JP | 2000202299 | 7/2000 |
| JP | 2000212212 | 8/2000 |
| JP | 2001009290 | 1/2001 |
| JP | 2001187345 | 7/2001 |
| JP | 2002045703 | 2/2002 |
| JP | 2002066329 | 3/2002 |
| JP | 2002102710 | 4/2002 |
| JP | 2002172327 | 6/2002 |
| JP | 2002200429 | 7/2002 |
| JP | 2002205960 | 7/2002 |
| JP | 2002233765 | 8/2002 |
| JP | 3351068 | 11/2002 |
| JP | 2003071294 | 3/2003 |
| JP | 3540827 | 7/2004 |
| JP | 3540828 | 7/2004 |
| JP | 3577786 | 10/2004 |
| JP | 2007-010780 | 1/2007 |
| WO | WO 97/37765 | 10/1997 |
| WO | WO 99/01460 | 1/1999 |
| WO | WO 99/19280 | 4/1999 |
| WO | WO 00/37175 | 6/2000 |
| WO | WO 00/50470 | 8/2000 |
| WO | WO 01/10876 | 2/2001 |
| WO | WO 01/47839 | 7/2001 |
| WO | WO 01/48028 | 7/2001 |
| WO | WO 01/68572 | 9/2001 |
| WO | WO 01/83447 | 11/2001 |
| WO | WO 02/04119 | 1/2002 |
| WO | WO 02/38628 | 5/2002 |
| WO | WO 02/46249 | 6/2002 |
| WO | WO 02/066404 | 8/2002 |
| WO | WO 02/066405 | 8/2002 |
| WO | WO 02/083306 | 10/2002 |
| WO | WO 03/004158 | 1/2003 |
| WO | WO 03/053890 | 7/2003 |
| WO | WO 03/053891 | 7/2003 |
| WO | WO 2004/056477 | 7/2004 |
| WO | WO 2004/056478 | 7/2004 |
| WO | WO 2004/056479 | 7/2004 |
| WO | WO 2004/056480 | 7/2004 |
| WO | 2004/064798 | 8/2004 |
| WO | 2004/083263 | 9/2004 |
| WO | WO 2004/083263 | 9/2004 |
| WO | WO 2005/123633 | 12/2005 |
| WO | WO 2005/123884 | 12/2005 |
| WO | WO 2006/096881 | 9/2006 |
| WO | WO 2007/007272 | 1/2007 |
| WO | 2008/118923 | 10/2008 |

OTHER PUBLICATIONS

Shah, et. al., "Design Parameters Estimations for Bubble Column Reactors," AIChE J., 28(3), 353-379 (1982).*
ACHEMA News, "Novel LAO Technology Makes Commercial Debut," in Chemical Engineering Progress, Jul. 2006, p. 13.*
Lide, et al., CRC Handbook of Chemistry and Physics, 90th Edition, 2010 Internet Version.*
Lide, et al.,(CRC Handbook of Chemistry and Physics, 90th Edition, 2010 Internet Version.*
Seador, et al., "Distillation" in Perry's Chemical Engineers Handbook, R. H. Perry and D. W. Green, eds., 1997, Wiley, available on-line at www.knovel.com.*
A. Ranwell et al., "Potential Application of Ionic Liquids for Olefin Oligomerization," ACS Symposium Series, Chapter 12, 2002, 818, pp. 147-160.
R.D. Kohn et al., 1,3,5-Triazacyclohexane Complexes of Chromium as Homogeneous Model Systems for the Phillips Catalyst, ACS Symposium Series, 2003, 857, pp. 88-100.
K.R. Dunbar et al., "Structure of [HTMPP]$_3$W$_2$CL$_9$[HTMPP=Tris(2,4,6-trimethoxyphenyl)-phosphonium]," Acta Cryst., 1991, C47, pp. 23-26.
D.H. Morgan et al., "The Effect of Aromatic Ethers on the Trimerisation of Ethylene using a Chromium Catalyst and Aryloxy Ligands," Adv. Synth. & Catalysis, 2003, 345, pp. 939-942.
Y.Yang et al., "Roles of chloro compound in homogeneous [Cr(2-ethylhexanoate)$_3$/2,5-dimethylpyrrole/triethylaluminum/chloro compound] catalyst system for ethylene trimerization," Applied Catalysis A: General, 2000, 193, pp. 29-38.
H. Mahomed et al., "Ethylene trimerisation catalyst based on substituted cyclopentadienes," Applied Catalysis A: General, 2003, 255, pp. 355-359.
Kohn et al., Triazacyclohexane complexes of chromium as highly active homogeneous model sytstems for the Philips catalyst, Chem. Commun., 2000, pp. 1927-1928.
A. Carter et al., "High activity ethylene trimerisation catalysts based on diphosphine ligands," Chem. Commun., 2002, pp. 858-859.
D.S. McGuinness et al., "Novel Cr-PNP complexes as catalysts for the trimerisation of ethylene," Chem. Commun. 2003, pp. 334-335.
C.N. Nenu et al., "Single-site heterogeneous Cr-based catalyst for the selective trimerisation of ethylene," Chem. Commun., 2005, pp. 1865-1867.
K. Blann et al., "Highly selective chromium-based ethylene trimerisation catalysts with bulky diphosphinoamine ligands," Chem. Commun., 2005, pp. 620-621.
M.J. Overett et al., "Ethylene trimerisation and tetramerisation catalysts with polar-substituted diphosphinoamine ligands," Chem. Commun., 2005, pp. 622-624.
Hecheng Shuzhi Ji Suliao, China Synthetic Resin and Plastics, 2001, 18(2), 23-25, 43.
T. Imamoto et al., "Synthesis and reactions of Optically Pure Cyclohexyl (o-methoxyphenyl)phosphine-Borane and t-Butyl-(o-methoxyphenyl)phosphine-Borane," Heteroatom Chemistry, 1993, vol. 4, No. 5, pp. 475-486.
N.J. Robertson et al., "Chromium(II) and Chromium (III) Complexes Supported by Tris(2-pyridylmethyl)amine: Synthesis, Structures, and Reactivity," Inorg. Chem., 42, pp. 6876-6885 (2003).
L. Hirsivaara et al., "M(CO)$_6$ (M=Cr, Mo, W) derivatives of (o-anisyl)diphenylphosphine, bis(o-anisyl)phenylphosphine tris(o-anisyl)phosphine and (p-anisyl)bis(o-anisyl)phosphine," Inorganica Chimica ACTA, 2000, 307, pp. 47-56.
D.S. McGuinness et al., "First Cr(III)-SNS Complexes and Their Use as Highly Efficient Catalysts for the Trimerization of Ethylene to 1-Hexene," J. Am .Chem. Soc., 2003, 125, pp. 5272-5273.
C. Andes et al., "New Tantalum-based Catalyst System for the Selective Trimerization of Ethene to 1-Hexene," J. Am. Chem. Soc., 2001, 123, pp. 7423-7424.
T.Agapie et al., "Mechanistic Studies of the Ethylene Trimerization Reaction with Chromium-Diphosphine Catalysts: Experimental Evidence for a Mechanism Involving Metallacyclic Intermediates," J. Am. Chem. Soc., 126, 2004, pp. 1304-1305.
A. Bollmann et al., "Ethylene Tetramerization: A New Route to Produce 1-Octene in Exceptionally High Selectivities," J. Am. Chem. Soc., 126, 2004, pp. 14712-14713.
A. Ariffin et al., "The asymmetric synthesis of phosphorus- and sulfur-containing tricarbonyl(n$^6$-arene) chromium complexes using the chiral base approach," J. Chem. Soc., Perkin Trans., 1, 1999, pp. 3177-3189.
T. Monoi et al., "Silica-supported Cr[N(SiMe$_3$)$_2$]$_3$/isobutylalumoxane catalyst for selective ethylene trimerization," Journal of Mol. Catalysis A: Chemical, 187, 2002, pp. 135-141.
J.T. Dixon et al., "Advances in selective ethylene trimerisation—a critical overview," Jrnl. of Organometallic Chem., 689, 2004, pp. 3641-3668.
R.M. Manyik et al., "A Soluble Chromium-Based Catalyst for Ethylene Trimerization and Polymerization," Journal of Catalysts, 1977, 47, pp. 197-209.
L. Hirsivaara et al., "Organometallic derivatives of multidentate phosphines [o-(methylthio)phenyl]diphenylphosphine and bis(o-(methylthio)phenyl(phenylphosphine: preparation and characterization of group 6 metal carbonyl derivatives," Jrnl. of Organometallic Chem., 579, 1999, pp. 45-52.

J. Pietsch et al., "Koordinationschemie funktioneller Phosphine II. Carbonyl(nitrosyl) wolfram-Komplexe mit 2-Diphenylphosphphinoanisol sowie 2-Diphenylphosphinoanilid, -benzoat und -phenolat als Liganden," Journal of Organometallic Chemistry, 495, 1995, pp. 113-125.

L. Dahlenburg et al., "Koordinationschemie funktioneller Phosphane VIII. Tetracarbonylkomplexe des Wolframs und Molybdans mit 2-(Diphenylphosphanyl)anilin-Liganden," Journal of Organometallic Chemistry, 585, 1999, pp. 225-233.

D. de Wet-Roos et al., "Homogeneous Tandem Catalysis of Bis(2-decylthioethyl)amine-Chromium Trimerization Catalyst in Combination with Metallocene Catalysts," Macromolecules, 2004, 37, pp. 9314-9320.

R. Blom et al., "1,3,5-Triazacyclohexane Complexes of Chromium as Homogeneous Model Systems for the Phillips Catalyst," Organometallic Catalysts and Olefin Polymerization, 2001, pp. 147-155.

K. Burgess, Stereochemically Matched (and Mismatched) Bisphosphine Ligands: DIOP-DIPAMP Hybrids, Organometallics, 1992, 11, pp. 3588-3600.

K.R. Dunbar et al., Carbon Monoxide Reactions of the Fluxional Phosphine Complex $(n^3-PR_3)Mo(CO)_3$ (R = 2,4,6-Trimethoxyphenyl), Organometallics, 1994, 13, pp. 2713-2720.

G. Boni et al., "Heterobimetallic Dibridged Complexes $[Cp_2Ta(u-CO)(u-PMe_2)M'(CO)_4]$ (M' = Cr, W): Synthesis and Reactivity toward Two-Electron Donor Ligands L (L = $PR_3$, $Me_2P(CH_2)nPMe_2$, CNR)," Organometallics, 1995, 14, pp. 5652-5656.

T. Agapie et al.; "A Chromium-Diphosphine System for Catalytic Ethylene Trimerization: Synthetic and Structural Studies of Chromium Complexes with a Nitrogen-Bridged Diphosphine Ligand with ortho-Methoxyaryl Substituents"; Organometallics, 25; 2006, pp. 2733-2742.

R.L. Wife et al., "Phosphine Oxide Anions in the Synthesis of Phosphine Ligands," Synthesis, 1983, pp. 71-73.

P.J.W. Deckers et al., "Catalytic Trimerization of Ethene with Highly Active Cyclopentadienyl-Arene Titanium Catalysts," Organometallics, 2002, 21, pp. 5122-5135.

S. Naqvi, "1-Hexene From Ethylene by the Phillips Trimerization Technology," available on-line at http://www.sriconsulting.com/PEP/Reports/Phase_95/RW95-1-1/RW95-1-8.html, Dec. 1997.

R. Agrawal "More Operable Fully Thermally Coupled Distillation Column Configurations for Multicomponent Distillation", Transactions of the Institution of Chemical Engineers, 1999, 77(A) pp. 543-553.

Y. T. Shah, et al. "Design Parameters Estimations for Bubble Column Reactors", American Institute of Chemical Engineers' Journal, 1982, vol. 28 No. 3, pp. 353-379.

K.M. Sundaram, et al. "Ethylene" Kirk-Othmer Encyclopedia of Chemical Technology, John Wiley, 2001, vol. 10, pp. 593-632, posted on-line Apr. 16, 2001.

H. Bohme et al., "Darstellung, Eigenschaften Und Umsetzungen Von (β-Alkoxycarbonyl-Alkyliden) Ammoniumsalzen", Tetrahedron, 1977, vol. 33, pp. 841-845.

D. Taniyama et al., "A Facile Asymmetric Synthesis of 1-Substituted Tetrahydroisoquinoline Based on a Chiral Ligand-Mediated Addition of Organolithium to Imine", Tetrahedron Asymmetry, 1999, vol. 10, pp. 221-223.

G. Domski et al, "Polymerization of α-olefins with Pyridylamidohafnium Catalysts: Living Behavior and Unexpected Isoselectivity from a $C_s$-Symmetric Catalyst Precursor", Macromolecules, 2007, vol. 40, pp. 3510-3513.

H. Gilman et al., "The Relative Reactivities of Organolithium and Organomagnesuim Compounds", J. Am. Chem. Soc., 1933, vol. 55, pp. 1265-1270.

M. Hasegawa et al., "Facile Asymmetric Synthesis of α-amino Acids Employing Chiral Ligand-Mediated Asymmetric Addition Reactions of Phenyllithium with Imines", Tetrahedron, 2000, vol. 56, 10153-10158.

J. Seador, et al. "Distillation", Perry's Chemical Engineers' Handbook 1997, Section 13, pp. 13-1-13-9, posted on-line Mar. 1, 2001.

P. Gros et al., "Aminoalkoxide-Mediated Formation and Stabilization of Phenylpyridyllithium: Straightforward Access to Phenylpyridine Derivatives", J. Org. Chem., 2003, vol. 68, pp. 2028-2029.

S. Walas, "Chemical Reactors", Perry's Chemical Engineers' Handbook 7th Edition, 1997, pp. 26-36-23-40.

S. Saito et al, "Nucleophilic Addition of Organomagnesiums to Aldimines: Scandium Triflate ($Sc(OTf)_3$) as an Effective Catalyst", Synlett, 2001, vol. 12, pp. 1859-1861.

SRI Consulting PEP Review, "1-Hexene From Ethylene by the Phillips Trimerization Technology", Jan. 8, 1995, available on-line at http://www.sriconsulting.com?PEP/Reports/Phase_95/RW95-1-8/RW95-1-8.html.

U. Jahn et al., "3,3-Dichloroprop-2-ene Iminium Salts (Vinylogous Viehe Salts): A Study of Their Reactivity Towards Nucleophiles", Synthesis, 1997, vol. 5, pp. 573-588.

V. Gibson, "Advances in Non-Metallocene Olefin Polymerization Catalysis", Chem Review, 2003, vol. 103, pp. 283-315.

T. Yamauchi et al., "Diastereoselective Addition of Organolithiums to 1,3-Oxazolidines Complexed With Aluminum Tris (2,6-Diphenylphenoxide) (ATPH)", Tetrahedron, 2005, vol. 61, pp. 1731-1736.

B. L. Small et al., "New Chromium Complexes for Ethylene Oligomerization: Extended Use of Tridentate Ligands in Metal-Catalyzed Olefin Polymerization," Macromolecules, vol. 37, No. 12, 2004, pp. 4375-4386.

Chandhua, D. "Expetiting Commercialization of 1-Hexene by Ethylene Trimerization in China" Petroleum & Petrochemical Today, 2002, vol. 10, No. 11, pp. 25-29.

"Hexene-1 via Ethylene Trimerization" PERP Report, Nexant/ Chem Systems, 2004, pp. 57-60.

Rao G.Y. et al. "On the coordinate mode of the Cr(2-ethylhecanoate) 3/triethylaluminum/ dimethylpyrrole/ tetrachloroethane", Journal of Beijing University of Chemical Technology, 2003, vol. 30, No. 1, pp. 80-82.

Washabaugh, M.W. et al., "Thiazolium C(2)-Proton Exchange: General-Base Catalysis, Direct Proton Transfer, and Acid Inhibition", Journal of American Society, 1989, vol. 111, pp. 674-683.

* cited by examiner

Process Schematic for the Production of 1-Hexene with 1-Hexene as a Solvent

Process Schematic for the Production of 1-Hexene with Toluene as a Solvent

Process Schematic for the Production of 1-Hexene with Isopentane as a Solvent at 800 psia Process Schematic for the Production of 1-Butene with Isopentane as a Solvent at 800 psia Process Schematic for the Production of 1-Hexene with Isopentane as a Solvent and Polymer Grade Feed

Fig. 8
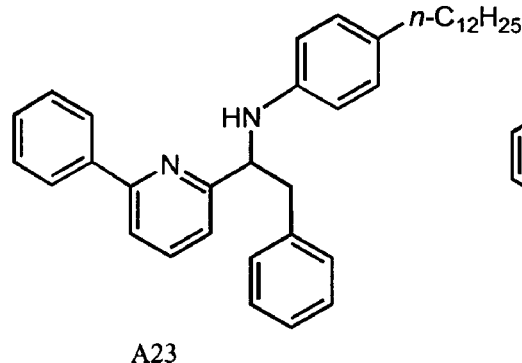
A23
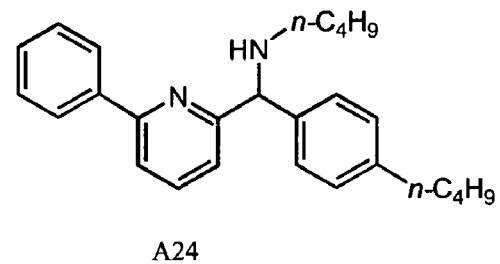
A24
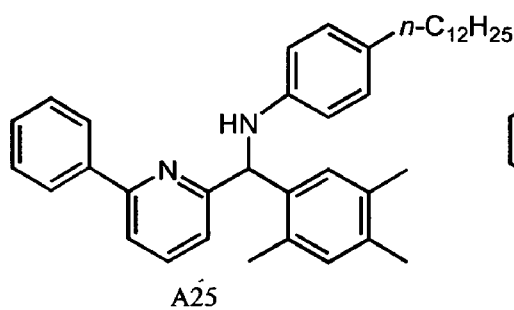
A25
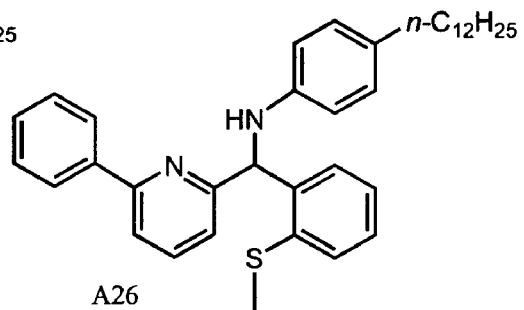
A26
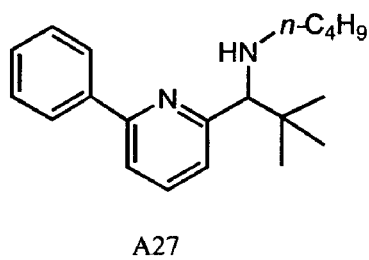
A27
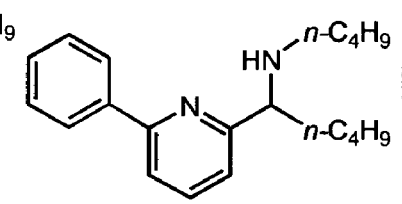
A28
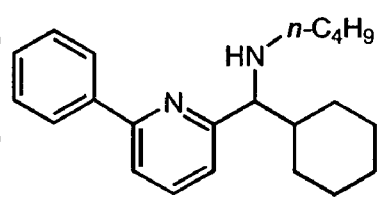
A29
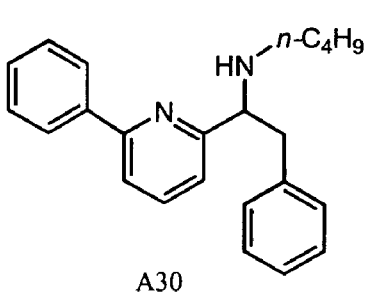
A30
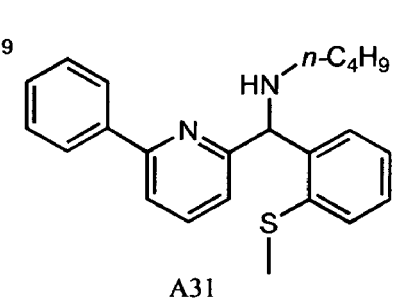
A31
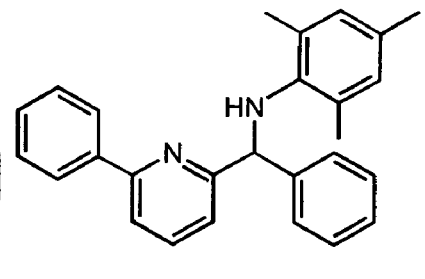
A32

Fig. 10
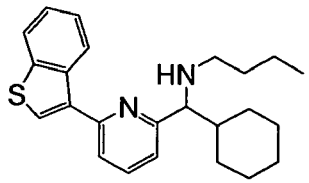 A42
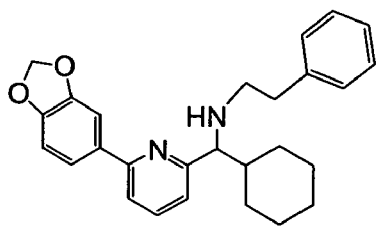 A43
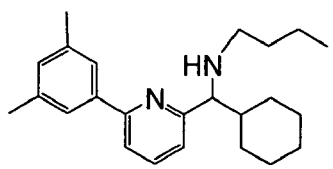 A44
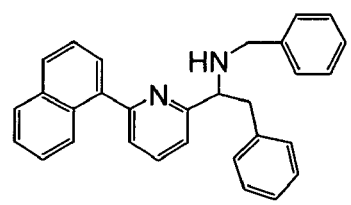 A45
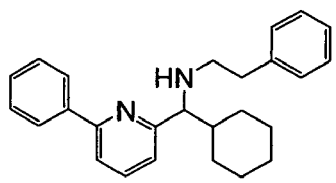 A46
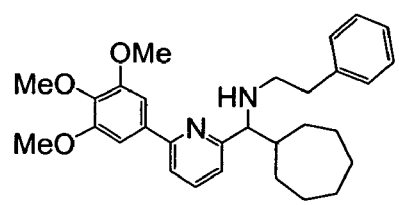 A47
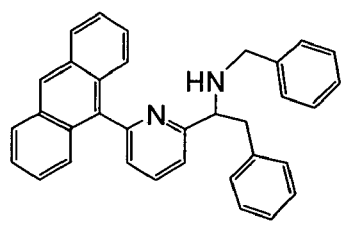 A48
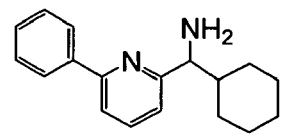 A49
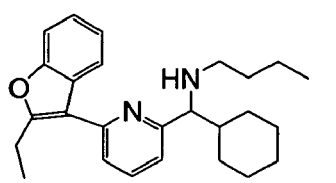 A50
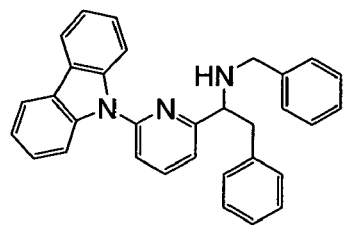 A51
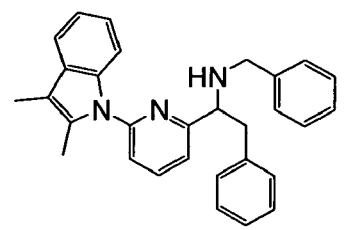 A52
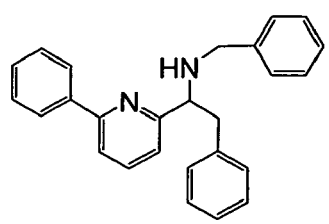 A72
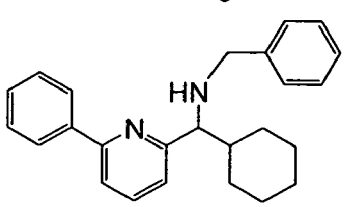 A73

Fig. 11
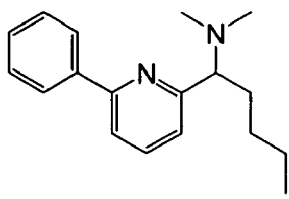 A53
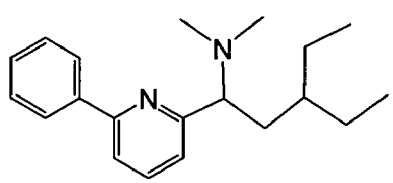 A54
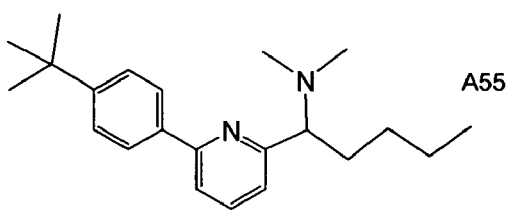 A55
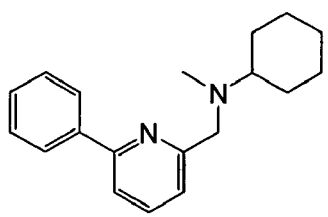 A56
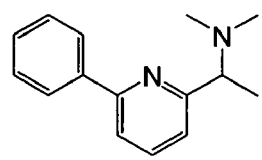 A57
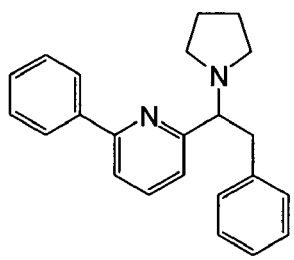 A58
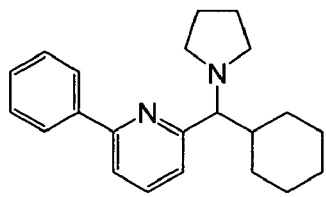 A59
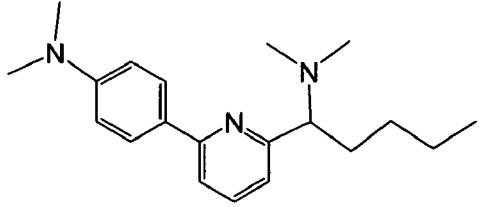 A60
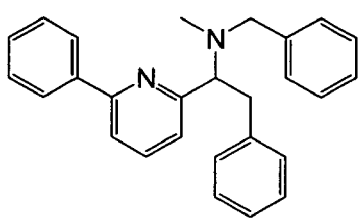 A61
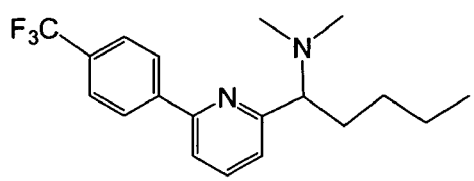 A62

Fig. 12
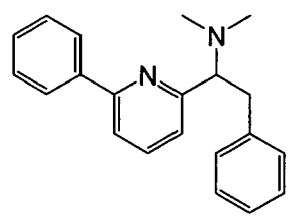 A63
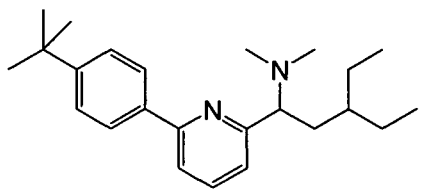 A64
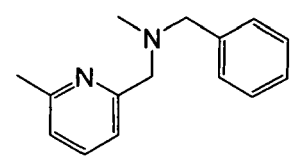 A65
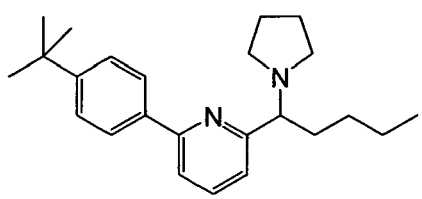 A66
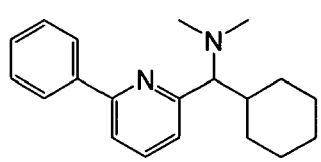 A67
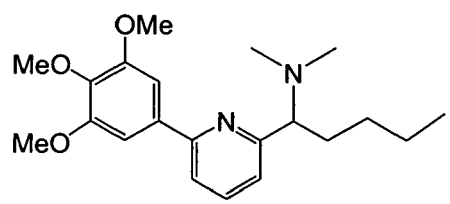 A68
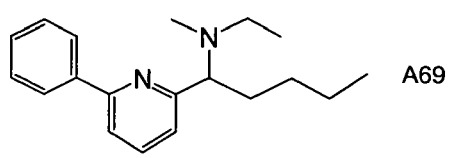 A69
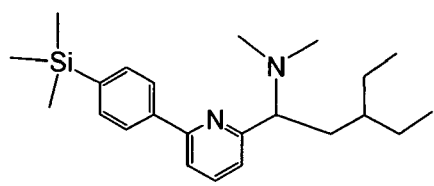 A70
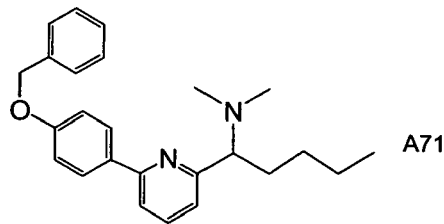 A71
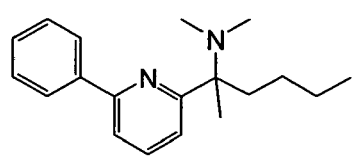 A74
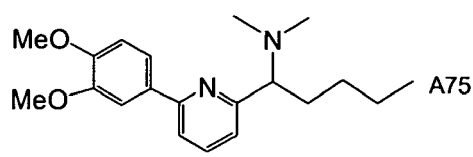 A75

Process Schematic for the Production of 1-Hexene with Isopentane as a Solvent

In-Line Process for Comonomer Generation

Fixed Bed Reactors for In-Line Comonomer Generation with Catalyst in Tubes with Coolant Fixed Bed Reactors for In-Line Comonomer Generation
with Cold Shot Cooling In-Line Process for Comonomer Generation

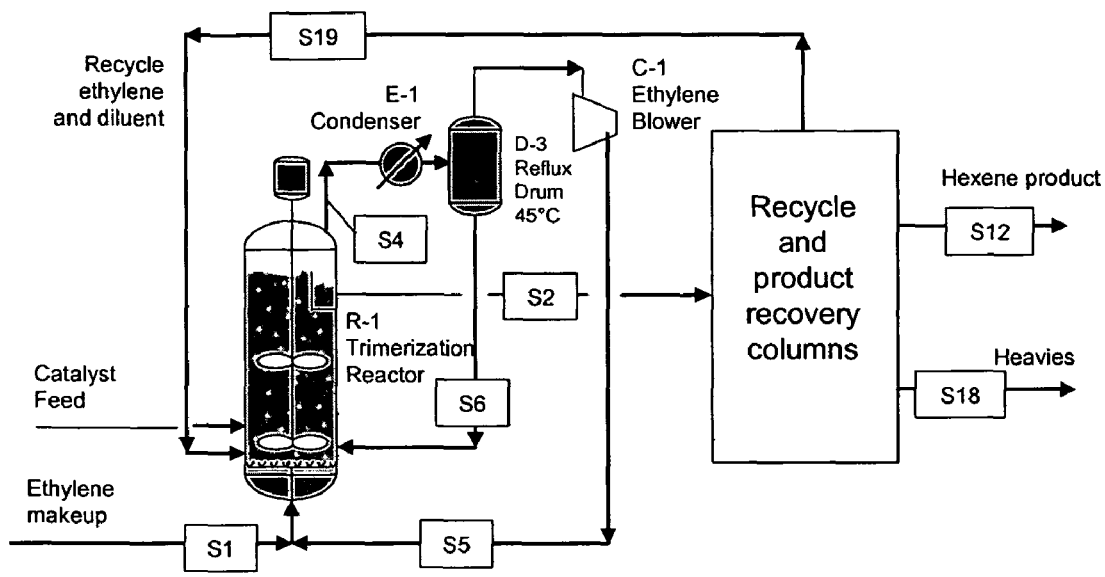
Figure 18. Flow diagram for the ethylene trimerization reactor system using evaporative cooling.

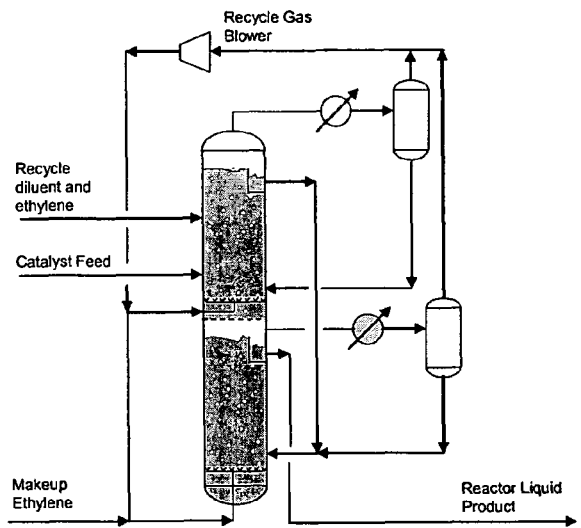

Figure 19A. Reactor embodiment with 2 stages in a single vessel, with partial condensers and recycle blower for uncondensed ethylene.

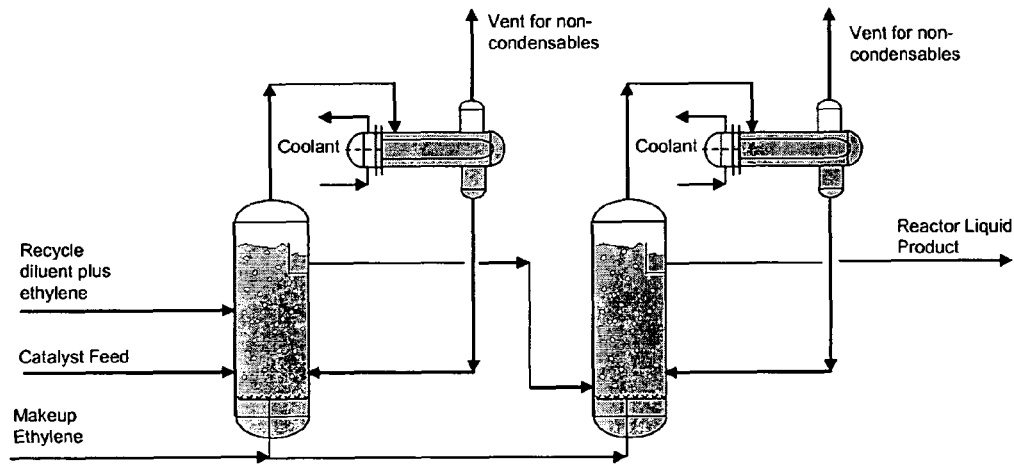

Figure 19B. Reactor embodiment with 2 stages with separate vessels. A "drumless condenser" arrangement is also shown for embodiments where the reactor vapors are substantially/totally condensed and returned to the reactor for cooling.

PROCESS FOR GENERATING ALPHA OLEFIN COMONOMERS

CROSS-REFERENCE TO RELATED APPLICATIONS

This application is a continuation-in-part of U.S. patent application Ser. Nos. 11/518,456 and 11/517,871, both filed Sep. 8, 2006, which are themselves continuations-in-part of U.S. patent application Ser. Nos. 11/346,651 and 11/346,652, both filed Feb. 3, 2006, the disclosures of all of which are incorporated herein by reference. This application also claims the benefit of U.S. Patent Application Ser. Nos. 60/873,162 and 60/873,221, both filed Dec. 6, 2006, and 60/841,226, filed Aug. 30, 2006, the disclosures of all of which are also incorporated herein by reference.

This application is also related to U.S. Patent Application Ser. Nos. 60/611,943, 60/660,018, 11/232,982, 11/233,227, 11/371,614, and 11/371,983, the disclosures of all of which are incorporated herein by reference.

FIELD OF THE INVENTION

The present invention relates to the field of chemical reaction and separation processes. It further relates to an improved process for generating alpha olefin comonomers from monomer using specific catalysts and/or catalyst systems. In particular, the present invention involves the use of one or more traps, such as filters and/or adsorbents, used in processes for generating alpha olefin comonomers using specific catalysts and/or catalyst systems.

BACKGROUND

Olefin polymerization, especially ethylene polymerization, can benefit from the addition of longer-chain comonomers, such as 1-butene, 1-hexene, and 1-octene, to produce linear low density polyethylene (LLDPE). LLDPE produced from 1-butene, 1-hexene and 1-octene accounts for a large percentage of the polyethylene resin market. In general, polyethylene plants buy butene, hexene and octene, which are produced in separate plants that typically produce a range of even-numbered alpha olefins from ethylene. It can be expensive to purchase these materials, and they add to the complexity of transport, storage and handling. An attractive alternative is to make the comonomer directly from the ethylene at the site where they will be used, if this can be done cleanly and economically.

The review article "Advances in selective ethylene trimerisation—a critical review" by Dixon et al. (*J. Organometallic Chemistry* 689 (2004) 3641-3668), herein incorporated by reference in its entirety, describes many different catalysts for trimerization. These catalyst systems contain chromium, and with particular ligands, such as aromatic species (e.g., pyrrolyl) or multidentate heteroatomic species. The chromium catalysts are typically activated by alkylaluminum and/or alkylaluminoxane activators. The article also describes group 4 and 5 early transition metals, such as Zr, V, Ta and Ti, and group 8 late transition metals, such as Ni, for showing some activity in trimerization.

Phillips has developed chromium-based catalysts that are selective towards making 1-hexene from ethylene. The major byproduct appears to be 1-decene. SRI Consulting PEP Review 95-1-8 entitled "1-Hexene From Ethylene By the Phillips Trimerization Technology," available on-line at http://www.sriconsulting.com/PEP/Reports/Phase_95/RW95-1-8/RW95-1-8.html, herein incorporated by reference in its entirety, describes the Phillips standalone process for making 1-hexene based on Phillips trimerization technology. In this process, ethylene and a homogeneous catalyst in a solvent are fed to a reactor. The reactor is a stirred tank with heat removal coils. This reactor operates at 115° C. and 49 kg/cm$^2$ (~700 psia), and converts about 75% of the ethylene fed. This reactor is 42,300 gal (5655 ft$^3$). A spare reactor is provided, since waxy buildup on the cooling coils may necessitate lengthy shutdowns for cleaning. The feed is approximately 29,000 lb/hr cyclohexane solvent (with catalyst) plus 36,000 lb/hr ethylene (27,000 fresh feed and 9,000 recycle). It is estimated that the resident time in the reactor is on average 4 to 5 hours. Selectivity in the SRI process by weight is about 93% to 1-hexene, 1% to other $C_6$'s, 1% to octenes, and 5% to decenes. The effluent from the reactor is contacted with octanol to kill the catalyst from further reaction. The effluent then goes to an ethylene column where unconverted ethylene is taken overhead and recycled to the reactor. Because ethylene is so volatile, an expensive cryogenic column must be used. Four more distillation columns follow to remove hexene, cyclohexane solvent, octene, and decene. Some of these are run under vacuum, which again makes for expensive hardware and operations. The bottoms from the decene tower is a small stream containing mainly octanol and deactivated catalyst. This stream is treated with caustic and then with acid to remove the catalyst by precipitation and by solution in an aqueous phase, which is separated from the organic phase containing the octanol. Octanol may then be recycled.

U.S. Pat. No. 5,382,738 to Reagen et al., herein incorporated by reference in its entirety, discloses catalyst systems comprising inorganic oxides, modified with a metal alkyl and an unsaturated hydrocarbon, which can be used to support a metal source, such as, for example, chromium, and a pyrrole-containing compound. The resultant catalyst systems can be used to oligomerize and/or trimerize olefins via a slurry process.

U.S. Pat. No. 5,523,507 to Reagen et al., herein incorporated by reference in its entirety, discloses novel chromium-containing compounds prepared by forming a mixture of the chromium salt, a metal amide, and an ether either supported or unsupported. These novel chromium-containing compounds are activated by non-hydrolyzed alkyl aluminum compound and a Lewis acid.

U.S. Pat. No. 5,451,645 to Reagen et al., herein incorporated by reference in its entirety, discloses novel chromium-containing compounds prepared by forming a mixture of a chromium salt, a metal amide, and an ether. These novel chromium-containing, or chromium pyrrolide compounds, with a metal alkyl and an unsaturated hydrocarbon, can be used as a co-catalyst system in the presence of an olefin polymerization catalyst system to produce a comonomer in-situ with trimerization.

U.S. Pat. No. 5,543,375 to Lashier et al., herein incorporated by reference in its entirety, discloses a process to stabilize and/or reactivate an olefin production catalyst system, which comprises contacting an olefin production catalyst system, either before or after use, with an aromatic compound.

European Publication No. 0 668 106 to Freeman et al., herein incorporated by reference in its entirety, discloses a process which will effectively deactivate, inhibit, and/or "kill" an olefin production catalyst, and halt polymer production in an olefin production process. It further provides for a process which can remove an olefin production catalyst from the product stream, and recover catalyst by-products for recycle, and/or recovery.

International Publication No. WO 99/19280 A1 to Woodard et al., herein incorporated by reference in its entirety, discloses a process in which olefins are trimerized in the presence of a catalyst system comprising a chromium source, a pyrrole containing compound and a metal alkyl. The process is preformed in a reactor and provides for a separator for collection of the desired products.

International Publication Nos. WO 2004/056478 and WO 2004/056479, both to Blann et al., both hereby incorporated by reference in their entirety, disclose processes and catalysts to prepare an olefinic stream with more than 30% of 1-octene. The catalysts for this system are those that contain chromium or a chromium salt and a heteroatomic ligand.

A need exists for an improved process to generate alpha olefin comonomers. More particularly, a need exists for a reaction and separation process to generate 1-butene, 1-hexene, and/or 1-octene from ethylene for subsequent isolation or storage prior to being used in a polymerization reactor or other chemical process requiring such comonomer.

With regard to specific oligomerization catalyst systems, particularly ethylene trimerization systems, the following references are of interest: U.S. Pat. Nos. 3,333,016, 4,668,838, 5,137,994, 5,198,563, 5,382,738, 5,438,027, 5,439,862, 5,491,272, 5,523,507, 5,543,375, 5,744,677, 5,750,816, 5,750,817, 5,856,257, 5,856,612, 5,910,619, 5,968,866, 6,133,495, and 6,344,594; U.S. Patent Application Publication No. 2002/0035029 A1; International Publication Nos. WO 01/68572, WO 02/04119 (and related U.S. Pat. No. 6,800,702, as well as related U.S. Patent Application Publication Nos. 2003/166456 and 2005/020788), WO 02/066404, WO 02/083306, WO 03/004158, WO 03/053890, WO 04/056477, WO 04/056478, WO 04/056479, and WO 04/056480; European Publication Nos. EP 0 416 304 B1, EP 0 537 609, EP 0 608 447 B1, EP 0 614 865 B1, EP 0699648 B1, EP 0780353 B1, and EP 1110930 A1; Canadian Patent Nos. CA 2,087,578 and CA 2,115,639; Japanese Patent Publication Nos. JP 2001187345 A2 and JP 2001187345 A2; *J. Am. Chem. Soc.* 123, 7423-7424 (2001); McGuinness et al., *J. Am. Chem. Soc.* 125, 5272-5273, (2003); and Carter et al., *Chem. Commun.,* 2002, pp. 858-859.

Likewise additional references regarding ethylene trimerization catalysts include: U.S. Pat. Nos. 3,333,016, 3,300,458, 4,472,525, 4,668,838, 4,689,437, 4,777,315, 4,853,356, 5,376,612, 5,382,738, 5,439,862, 5,523,507, 5,550,305, 5,557,026, 5,563,312, 5,668,249, 5,731,487, 5,744,677, 5,750,816, 5,750,817, 5,763,723, 5,811,618, 5,814,575, 5,856,257, 5,856,610, 5,856,612, 5,859,303, 5,910,619, 5,919,996, 5,968,866, 6,031,145, 6,133,495, 6,337,297, 6,344,594, 6,455,648, 6,521,806, 6,610,805, and 6,828,269; U.S. Patent Application Publication Nos. 2002/0035029, 2002/183574, 2003/130551, 2003/149198, 2004/122271, and 2004/228775; Chinese Publication No. CN 1256968; European Publication Nos. EP 622 347, EP 608 447, EP 706 983, and EP 1 110 930; British Patent No. GB 2298864; Japanese Publication Nos. JP 06-515873, JP 07-215896, JP 07-267881, JP 09-020692, JP 09-020693, JP 09-268133, JP 09-268134, JP 09-268135, JP 10-007593, JP 10-007594, JP 10-007595, JP 10-036431, JP 10-036432, JP 10-045638, JP 10-087518, JP 11-092407, JP 11-092408, JP 11-222445, JP 2000-176291, JP 2000-202299, JP 2000-212212, JP 2001-009290, JP 2002-045703, JP 2002-066329, JP 2002-102710, JP 2002-172327, JP 2002-200429, JP 2002-205960, JP 2002-233765, JP 2003-071294, JP 3351068 B2, JP 3540827 B2, JP 3540828 B2, and JP 3577786 B2; International Publication Nos. WO 97/37765, WO 01/10876, WO 01/47839, WO 01/83447, WO 02/83306, WO 03/004158, WO 03/053890, WO 03/053891, WO 04/056479, WO 04/056478, and WO 04/083263; *Journal of Organometallic Chemistry* 579 (1999) 45-52, *Organometallics* 1992, 11 3588-3600, *Organometallics* 1995, 14, 5652-5656, *J. Chem. Soc., Perkin Trans.* 1, 1999, 3177-3189, *Organometallics* 1994, 13, 2713-2720, *Journal of Organometallic Chemistry*, Volume 585, Issue 2, 15 Aug. 1999, pgs 225-233, *Acta Cryst.* (1991). C47, 23-26, *Journal of Organometallic Chemistry*, Vol 495, No. 1, 14 Jun. 1995, pgs 113-125, *Inorg. Chim. ACTA* (2000), 307(1-2), 47-56. *Chem. Commun.* 2005, 620-621, *Chem. Commun.* 2005, 622-624, *Chem. Commun.* 2005, 1865-1867, *J. Am. Chem. Soc.* 2004, 126, 14712-14713, *J. Am. Chem. Soc.* 2004, 126, 1304-1305, *Macromolecules,* 2004, 37, 9314-9320, *Journal of Organometallic Chemistry,* 2004, 689, 3641-3668, *Heteroatom Chemistry,* 1993, 4, 475-486; *Synthesis*, 1983, 1, 71-73; U.S. Pat. No. 6,800,702; *Chem. Commun.,* 2002, 8, 858-859; *PERP Report*, Nexant/Chem Systems, 2004, 57-60; *Dangadi Shiyou Shihu,* 2002, 10, 25-29; *ACS Symposium Series,* 2002, 818, 147-160; *Journal of Organometallic Chemistry,* 2004689, 3641-3668; *Journal of Catalysis,* 1977, 47, 197-209; *J. Am. Chem. Soc.,* 1989, 11, 674-675; *Applied Catalysis, A* (General) 2000, 193, 29-38; *Hecheng Shuzhi Ji Suliao,* 2001, 18, 23-25, 43; *Organometallic Catalysts and Olefin Polymerization,* 2001, 147-155; *J. Mol. Catalysis A: Chemical* (2002), 187, 135-141; *J. Am. Chem. Soc.,* 2002, 125, 5272-5273; *Chem. Commun.* 2003, 3, 334-335; *Beijing Huagong Daxue Xuebao, Ziran Kexueban,* 2003, 30, 80-82; *Adv. Synth. & Catalysis,* 2003, 345, 939-942; *Applied Catalysis, A: General,* 2003, 255, 355-359; *J. Am. Chem. Soc.* 2004, 126, 1304-1305; *ACS Symposium Series,* 2003, 857 (Beyond Metallocenes), 88-100; and *J. Am. Chem. Soc.,* 2004, 126, 14712-14713. Although the catalyst compositions in each of the above described references may be useful for the trimerization of ethylene, there remains a desire to improve the performance of olefin oligomerization catalysts from the standpoint of productivity and selectivity for oligomers such as 1-hexene or 1-octene, particularly where use in a commercial process, particularly an in-line process, is concerned.

Several pyridyl amine catalyst complexes have been disclosed for the polymerization or copolymerization of ethylene, propylene, isobutylene, octene, and styrene by Symyx Technologies, Inc. in U.S. Pat. Nos. 6,713,577, 6,750,345, 6,706,829, 6,727,361, and 6,828,397. Pyridyl amines were also disclosed in U.S. Pat. Nos. 6,103,657 and 6,320,005, assigned to Union Carbide Chemical and Plastics Technology Corporation, in which zirconium was used as the metal center, and the catalyst complex was used to polymerize alpha-olefins, and in U.S. Pat. No. 5,637,660, assigned to Lyondell Petrochemical Company, which also describes Group 4 complexes of pyridyl amine ligands. Robertson et al., *Inorg. Chem.* 42, pp 6875-6885 (2003), discloses chromium complexes of tris(2-pyridylmethyl)amine for ethylene polymerization.

SUMMARY OF THE INVENTION

This invention relates to the oligomerization, and more specifically the trimerization and/or tetramerization of $C_2$ to $C_{12}$ olefins, preferably alpha-olefins, preferably ethylene, using the ligand-metal-precursor combinations, metal-ligand complexes, and/or catalyst systems described herein in the unique processes for generating comonomer described herein. Specifically, this invention relates to the trimerizing and/or tetramerizing of ethylene to form 1-hexene and/or 1-octene using the ligand-metal-precursor combinations, metal-ligand complexes, and/or catalyst systems described herein in the unique processes for generating comonomer described herein.

It has been discovered that it is possible to selectively make 1-butene, 1-hexene, and other alpha olefin comonomers from ethylene via a simpler and less expensive process. It has also been discovered that it is possible to generate 1-hexene and other desired comonomers from olefins such as ethylene immediately before the polyethylene polymerization reactor, optionally with no isolation or storage of the hexene or other desired comonomer produced.

According to the present disclosure, an advantageous method for preparing alpha olefin comonomers from an olefin such as ethylene comprises the following steps: providing one or more comonomer synthesis reactors configured in series, and one or more downstream gas/liquid phase separators configured in series; feeding olefin (e.g., ethylene) and a catalyst in a solvent and/or diluent to the one or more comonomer synthesis reactors; reacting in the one or more comonomer synthesis reactors the ethylene and the catalyst in said solvent and/or diluent under reaction conditions sufficient to produce an effluent stream comprising one or more desired comonomers; passing the effluent stream to the one or more downstream gas/liquid phase separators to form a gas stream comprising the unreacted olefin (e.g., ethylene), and a liquid stream comprising the comonomer(s); optionally recycling to the one or more comonomer synthesis reactors the unreacted olefin (e.g., ethylene) and optionally a portion of the liquid stream; storing at least a portion of the liquid stream for subsequent processing of the comonomer(s); and purifying at least a portion of said liquid stream by removing at least one of solid polymer, catalyst, catalyst activator(s), catalytic decomposition products, and undesirable olefins therefrom, wherein the comonomer(s) is(are) selected from the group consisting of 1-butene, 1-hexene, 1-octene, 1-decene, and mixtures thereof, and is(are) similar in composition to the solvent and/or diluent.

A further aspect of the present disclosure relates to an advantageous method for preparing alpha olefin comonomers from an olefin such as ethylene, which comprises the following steps: providing one or more comonomer synthesis reactors configured in series, one or more downstream gas/liquid phase separators configured in series, and one or more distillation columns configured in series; feeding olefin (e.g., ethylene) and a catalyst in a solvent and/or diluent to the one or more comonomer synthesis reactors; reacting in the one or more comonomer synthesis reactors the olefin (e.g., ethylene) and the catalyst in the solvent and/or diluent under reaction conditions sufficient to produce an effluent stream comprising one or more desired comonomers; passing the effluent stream to the one or more downstream gas/liquid phase separators to form a gas stream comprising the unreacted olefin (e.g., ethylene), and a liquid stream comprising the comonomer(s); purifying at least a portion of the liquid stream by removing at least one of solid polymer, catalyst, catalyst activator(s), catalytic decomposition products, and undesirable olefins therefrom; passing at least a portion of the liquid stream to the one or more distillation columns to separate the comonomer product; optionally recycling to the one or more comonomer synthesis reactors the unreacted olefin (e.g., ethylene) and optionally the catalyst and the solvent and/or diluent; and storing the comonomer product for subsequent processing, wherein the comonomer(s) is(are) selected from the group consisting of 1-butene, 1-hexene, 1-octene, 1-decene, and mixtures thereof.

Another aspect of the present disclosure relates to an advantageous method for preparing alpha olefin comonomers from an olefin such as ethylene, which comprises the following steps: providing a combination comonomer synthesis reactor and gas/liquid phase separator into a single vessel; feeding olefin (e.g., ethylene) and a catalyst in a solvent and/or diluent to the combination comonomer synthesis reactor and gas/liquid phase separator; reacting in the combination comonomer synthesis reactor and gas/liquid phase separator the olefin (e.g., ethylene) and the catalyst in the solvent and/or diluent under reaction conditions sufficient to produce an effluent stream comprising a gas stream comprising unreacted olefin (e.g., ethylene) and a liquid stream comprising one or more desired comonomers; optionally recycling to the combination comonomer synthesis reactor and gas/liquid phase separator the gas stream and optionally at least a portion of the liquid stream; purifying at least a portion of said liquid stream by removing at least one of solid polymer, catalyst, catalyst activator(s), catalytic decomposition products, and undesirable olefins therefrom; and storing at least a portion of the liquid stream for subsequent processing of the comonomer(s), wherein the comonomer(s) is(are) selected from the group consisting of 1-butene, 1-hexene, 1-octene, 1-decene, and mixtures thereof.

Another aspect of the present disclosure relates to a method for generating 1-hexene and other desired comonomers immediately before a polyethylene polymerization reactor can include the steps of: providing an in-line comonomer synthesis reactor and a downstream gas/liquid phase separator prior to a polyethylene polymerization reactor; feeding ethylene monomer and a catalyst in a solvent and/or diluent to said comonomer synthesis reactor; reacting said ethylene and said catalyst in solvent and/or diluent under reaction conditions sufficient to produce an effluent stream comprising one or more desired comonomer(s), e.g., selected from the group consisting of 1-hexene, 1-octene, 1-decene, and mixtures thereof; passing said effluent stream from said comonomer synthesis reactor to said downstream gas/liquid phase separator to separate a gas stream from a bottoms stream, wherein said gas stream comprises said one or more comonomers and optionally also ethylene; purifying said bottom stream by removing at least one of solid polymer, catalyst, catalyst activator(s), catalytic decomposition products, purge heavies, and undesirable olefins therefrom; recycling said solvent and/or diluent to said comonomer synthesis reactor; and passing said gas stream to said polyethylene polymerization reactor to provide a comonomer source.

Another aspect of the present disclosure relates to a method for generating 1-hexene, and optionally other desired comonomers, immediately before a polyethylene polymerization reactor, which includes the steps of: providing an in-line comonomer synthesis reactor prior to a polyethylene polymerization reactor, wherein the reactor is a fixed bed type with a catalyst in a fixed position; feeding ethylene to said comonomer synthesis reactor; reacting said ethylene and said catalyst under reaction conditions sufficient to produce an effluent stream comprising one or more comonomers, e.g., selected from the group consisting of 1-hexene, 1-octene, 1-decene, and mixtures thereof; purifying said effluent stream by removing at least one of solid polymer, catalyst, catalyst activator(s), catalytic decomposition products, purge heavies, and undesirable olefins therefrom; and directing said effluent stream to said polyethylene polymerization reactor to provide a comonomer source.

Another aspect of the present disclosure relates to a method for generating 1-hexene and other desired comonomers immediately before a polyethylene polymerization reactor, which includes the steps of: providing an in-line comonomer synthesis reactor and a downstream gas/liquid phase separator prior to a polyethylene polymerization reactor; feeding ethylene and a catalyst in a solvent and/or diluent to said comonomer synthesis reactor; reacting said ethylene and said catalyst in said solvent and/or diluent under reaction conditions sufficient to produce an effluent stream comprising ethylene and one or more comonomers, e.g., selected from the group consisting of 1-hexene, 1-octene, 1-decene, and mixtures thereof; passing said effluent stream from said comonomer synthesis reactor to said downstream gas/liquid phase separator to separate a gas stream from a bottom stream, wherein said gas stream comprises a mixture of ethylene and said one or more comonomers; purifying said effluent stream by removing at least one of solid polymer, catalyst, catalyst activator(s), catalytic decomposition products, purge heavies, and undesirable olefins therefrom; and transporting, optionally without isolation or storage, said gas stream to said polyethylene polymerization reactor to provide a comonomer source.

Numerous advantages can result from the advantageous methods of preparing comonomer disclosed herein and from the uses/applications therefor.

For example, in exemplary embodiments of the present disclosure, the disclosed methods for preparing olefin comonomers, optionally immediately before the polymerization reactor, can provide for substantial capital and operational cost savings over a conventional standalone process for manufacturing comonomer.

In a further exemplary embodiment of the present disclosure, the disclosed methods for preparing olefin comonomers, optionally immediately before the polymerization reactor, can provide for a simpler process through the elimination of one or more separation columns.

In a further exemplary embodiment of the present disclosure, the disclosed methods for preparing olefin comonomers, optionally immediately before the polymerization reactor, can provide for flexibility in use of catalysts for the oligomerization reaction.

In a further exemplary embodiment of the present disclosure, the disclosed methods for preparing alpha olefin comonomers, optionally immediately before the polymerization reactor, can provide for the capability to produce at least two of 1-butene, 1-hexene, and 1-octene through catalyst selection.

In a further exemplary embodiment of the present disclosure, the disclosed methods for preparing olefin comonomers, optionally immediately before the polymerization reactor, can provide for high selectivity and activity through trimerization catalyst selection.

In a further exemplary embodiment of the present disclosure, the disclosed methods for preparing olefin comonomers, optionally immediately before the polymerization reactor, can eliminate the need to recover unreacted ethylene in high purity.

In a further exemplary embodiment of the present disclosure, the disclosed methods for preparing olefin comonomers, optionally immediately before the polymerization reactor, can permit the discharge of deactivated catalyst with comonomer product.

In a further exemplary embodiment of the present disclosure, the disclosed methods for preparing olefin comonomers, optionally immediately before the polymerization reactor, can eliminate the need to store or isolate the comonomer produced.

In a further exemplary embodiment of the present disclosure, the disclosed methods for preparing olefin comonomers, optionally immediately before the polymerization reactor, can provide for flexibility in use of catalysts for the oligomerization reaction.

In a further exemplary embodiment of the present disclosure, the disclosed methods for preparing olefin comonomers, optionally immediately before the polymerization reactor, can provide for process simplification, and the associated benefits thereof.

In a further exemplary embodiment of the present disclosure, the disclosed methods for preparing olefin comonomers, optionally immediately before the polymerization reactor, can provide for continual removal of hexene from the comonomer synthesis reactor zone, which can advantageously reduce the formation of decene byproduct.

These and other advantages, features and attributes of the disclosed methods for preparing olefin comonomers of the present disclosure and their advantageous applications and/or uses will be apparent from the detailed description which follows, particularly when read in conjunction with the figures appended hereto.

BRIEF DESCRIPTION OF THE DRAWINGS

To assist those of ordinary skill in the relevant art in making and using the subject matter hereof, reference is made to the appended drawings, wherein:

FIG. 8 illustrates pyridyl-amine ligands A23-A32.
FIG. 10 illustrates pyridyl-amine ligands A42-A52.
FIG. 11 illustrates pyridyl-amine ligands A53-A62.
FIG. 12 illustrates pyridyl-amine ligands A63-A75.

FIG. 18 depicts an exemplary process schematic of the process of the present invention for generating 1-hexene utilizing evaporative cooling for the reactor.

FIGS. 19A-B depict process schematics for alternate configurations of the process of the present invention for generating 1-hexene where multiple reactor stages are desired.

DETAILED DESCRIPTION OF THE INVENTION

Figure 1:
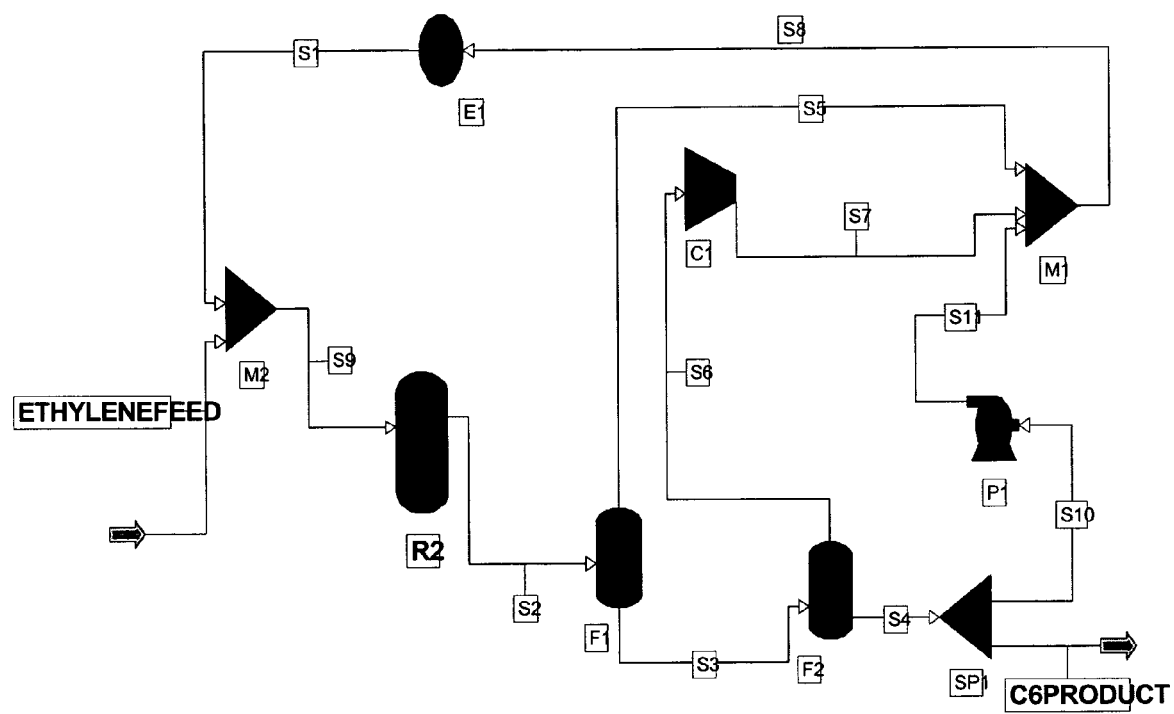
FIG. 1 depicts an exemplary process schematic of the process of the present invention for generating 1-hexene with 1-hexene as a solvent and/or diluent.

For the purposes of this invention and the claims thereto, when an oligomeric material (such as a dimer, trimer, tetramer, and/or pentamer) is referred to as comprising an olefin, the olefin present in the material is the reacted form of the olefin. Likewise, the active species in a catalytic cycle may comprise the neutral or ionic forms of the catalyst. In addition, a reactor is any container(s) in which a chemical reaction occurs.

As used herein, the new numbering scheme for the Periodic Table Groups is used as set out in CHEMICAL AND ENGINEERING NEWS, 63(5), 27 (1985).

As used herein, the term "about," whether in reference to a single value or a range of values, is defined according to the scope of the value(s) given the significant figures expressed. For instance, "about 99%" means from 98.50% to 99.49%; "about 99.0%" means from 98.950% to 99.049%; and "about 99.00% means from 98.9950% to 99.0049%.

For purposes of this invention, a catalyst system is defined to be the combination of an activator and a metal ligand complex or the combination of an activator, a ligand, and a metal precursor. A metal ligand complex is defined to be the product of the combination of a metal precursor and a ligand.

The phrase "optionally substituted" means that a moiety (such as a hydrocarbyl) may or may not be substituted. The term "substituted" means that at least one hydrogen atom bound to a carbon atom is replaced with a heteroatom containing group or a hydrocarbyl group. Further, when the term "substituted" or "optionally substituted" introduces a list of possible substituted groups, it is intended that the term apply to every member of that group. That is, the phrase "substituted alkyl, alkenyl, and alkynyl" is to be interpreted as "substituted alkyl, substituted alkenyl, and substituted alkynyl." Similarly, "optionally substituted alkyl, alkenyl, and alkynyl" is to be interpreted as "optionally substituted alkyl, optionally substituted alkenyl, and optionally substituted alkynyl."

The term "hydrocarbyl" as used herein refers to hydrocarbyl radicals containing 1 to 50 carbon atoms. Preferred hydrocarbyls contain 1 to 24 carbon atoms, more specifically 1 to 16 carbon atoms, including branched or unbranched, cyclic or acyclic, saturated or unsaturated species, such as alkyl groups, alkenyl groups, aryl groups, and the like.

The term "olefin selectivity," as used herein with reference to a metal-ligand complex, to a catalyst system, and/or to a reaction process, refers to the percentage (herein mole percentage, unless otherwise specified) content of one or more specific olefins (olefin comonomers) in relation to the total olefin content of the non-polymeric reaction product (i.e., excluding any olefin reactants, excluding any olefin solvents and/or diluents, and excluding any polymeric product, as defined below, having a double bond, but including any oligomeric olefin product, as defined below). Similarly, the term "olefinic purity," as used herein with reference to a composition such as a desired olefin product, refers to the percentage (herein mole percentage, unless otherwise specified) content of the desired olefin product in relation to the total olefin content of the non-polymeric reaction product (i.e., excluding any olefin reactants, excluding any olefin solvents and/or diluents, and excluding any polymeric product, as defined below, having a double bond, but including any oligomeric olefin product, as defined below).

Throughout this specification, the presence of one solid line and one dashed line between any pair of atoms is intended to indicate that the bond in question may be a single bond or a double bond, or a bond with bond order intermediate between single and double, such as the delocalized bonding in an aromatic ring.

Certain abbreviations used herein are as follows: "i-Pr" to refer to isopropyl; "t-Bu" to refer to tertiary-butyl; "i-Bu" to refer to isobutyl; "Me" to refer to methyl; "Et" to refer to ethyl; "Ph" to refer to phenyl; "Mes" to refer to mesityl (2,4,6-trimethyl phenyl); "TFA" to refer to trifluoroacetate; "THF" to refer to tetrahydrofuran; "TMA" to refer to $AlMe_3$; "TIBA" to refer to Al $(i-Bu)_3$; and "acac" to refer to acetylacetonate.

The present invention relates to an improved process for generating $C_{2+}$-pendant alpha olefin comonomers (e.g., 1-butene, 1-hexene, 1-octene, 1-decene, etc.) from alpha olefins, such as ethylene, using specific catalysts and/or catalyst systems as described below. The disclosed method of preparing 1-hexene, 1-octene, and other alpha olefin comonomers from ethylene prior to the polymerization reactor or other chemical process where it will be used greatly simplifies the comonomer synthesis process. A novel feature of the disclosed method of preparing 1-hexene, 1-octene, and other alpha olefin comonomers from ethylene is that ethylene is not recovered in high purity, which eliminates the need for a cryogenic distillation column and the associated capital and operating costs. Unconverted ethylene may then be recycled to the comonomer synthesis reactor, or sent on to another process, for example, a subsequent polyethylene polymerization process.

In a preferred embodiment of the present invention, the improved process for generating $C_{2+}$-pendant alpha olefin comonomers from olefins, such as ethylene, utilizes catalysts and/or catalyst systems that provide a product having an olefin product distribution that is neither a Schultz-Flory distribution (i.e., such as the distribution created by the Gulf/Chevron Phillips Chemical catalyst/reaction process) nor a pseudo-Poisson distribution (i.e., such as the distribution created by the Ethyl/Ineos/British Petroleum catalyst/reaction process). The phrase "neither a Schultz-Flory distribution nor a pseudo-Poisson distribution," as used herein with reference to a reaction product distribution, should be understood by one of ordinary skill in the art to mean that the reaction product distribution differs in a statistically significant way from the Schultz-Flory distribution and/or the pseudo-Poisson distribution. For instance, in one embodiment, the reaction product distribution has a $M_w/M_n$ ratio (analogous to a polydispersity index for polymer products; the ratio of the weight average distribution by the molecular weight of each reaction product molecule to the number average distribution by the number of carbons in each reaction product molecule) of less than 1.5, which reflects more than a 25% difference from the Schultz-Flory distribution $M_w/M_n$ ratio of 2. In preferred embodiments, the reaction product distribution has a $M_w/M_n$ ratio less than 1.4, less than 1.3, less than 1.2, less than 1.1, less than 1.07, less than 1.05, less than 1.03, or less than 1.01.

In another embodiment of the present invention, the improved process may be implemented immediately before the polymerization reactor with no isolation or storage of the 1-hexene produced. 1-Hexene can be swept out of the reaction zone or loop, optionally along with unconverted ethylene, leaving behind catalyst, by-products, and heavy solvent and/or diluent. Specific hardware implementations of this concept can include, but are not limited to, a "bubbling pot" and a reactor/knockout pot pumparound.

In another embodiment, the 1-hexene may be produced and isolated or stored for use as a comonomer later in a polymerization reactor on the same site, without being transferred to a remote site. In this embodiment, transferring of the comonomer to a remote site should be understood not to include merely sending the comonomer product through a conduit such as a pipe; in other words, a "site" should be understood to include anywhere that material can be reasonably transported through a conduit such as a pipe.

In an alternative embodiment of the present invention, 1-octene can be produced from ethylene. The improved process of the instant invention is also adaptable to catalysts which produce both 1-hexene and 1-octene.

Another advantage of the methods of the instant invention of preparing 1-hexene, 1-octene, and other alpha olefin comonomers from ethylene is that an elaborate on-site catalyst separation and disposal may not be needed. Additionally or alternately, on-site solids (catalyst, polymer, etc.) separation and disposal that are not elaborate may be advantageously used to prepare 1-hexene, 1-octene, and other alpha olefin comonomers, e.g., for use in (co)polymerization to form polyolefins. A further advantage of the method of the instant invention of preparing 1-hexene, 1-octene, and other alpha olefin comonomers from ethylene is that a small amount of a soluble or slurry catalyst that is sufficiently active may be utilized, such that it can be added in only small amounts. After deactivation, the catalyst can then be discharged with the comonomer product and, in some embodiments, incorporated into the final polymeric product.

In one exemplary embodiment, the comonomer synthesis reactor can be separate from the gas/liquid phase separator, which can permit independent control of reaction and separation conditions. In this particular embodiment, ethylene and catalyst in a solvent and/or diluent can be fed separately to a comonomer synthesis reactor. The purity of the ethylene feed may vary, but is preferably greater than 80% ethylene, more preferably greater than 99% ethylene, and in some cases greater than 99.8% pure. The reactor temperature and pressure can be controlled to provide for acceptable reaction rates and selectivities, as well as to provide for phase separation.

This invention further relates to processes for selectively oligomerizing (e.g., trimerizing and/or tetramerizing) $C_2$ to $C_{12}$ olefins, specifically ethylene, comprising reacting a catalytic composition or compound(s), optionally with one or more activators, with the olefin in the process described herein. As referred to herein, selective oligomerization refers to producing the desired oligomer with a selectivity of the reaction being at least 70%, more specifically at least 80%, by mole of oligomer, with the possibility that an acceptable amount of polymer is present, but with the preference that no polymer is present in the product. In other embodiments, less than 20 wt % of polymer is present, specifically less than 5 wt %, more specifically less than 2 wt %, based upon the total weight of monomer converted to oligomers and polymers, where a polymer is defined to mean a molecule comprising more than 100 mers (repeat units). An "oligomer" as used herein is defined to mean a molecule comprising from 2 to 100 mers (repeat units); however, desired oligomers are defined as described herein, but preferably do not contain more than 20 total carbons and/or preferably do not contain more than 10 repeat units. In other embodiments, selective oligomerization refers to producing one or two desired oligomers, with the selectivity of the one or two desired oligomers summing to at least 80% by sum of total moles of oligomers. Particularly preferred oligomeric olefins are molecules consisting of 2 to 100 mers with the olefinic unsaturation at the end of the oligomer (i.e., alpha-olefin oligomers).

In another embodiment, this invention relates to a process to trimerize or tetramerize a $C_2$ to $C_{12}$ olefin (preferably ethylene) wherein the process produces at least 70% selectivity for the desired oligomer(s) (specifically at least 80%, at least 85%, at least 90%, at least 95%, at least 98%, at least 99%, or at least 99.9%), calculated based upon the amount of the desired oligomer produced relative to the total yield; and at least 70% (specifically at least 80%, at least 85%, at least 90%, at least 95%, at least 98%, at least 99%, or at least 99.9%) of the olefin reacts to form a desired oligomer product.

One problem that may occur in/near the reactor in the systems/methods of the invention is fouling, or deposition of reactor contents/components onto cooling surfaces, which could ultimately plug up the reactor and/or conduits leading thereto/therefrom and/or which could require periodic (even frequent) shutdown of the reactor system for de-fouling. One way to reduce, inhibit, and/or prevent fouling can be to utilize/facilitate evaporative cooling of reactor components in/near the reactor, e.g., so that the condensing of the reactor components (e.g., olefin feed, solvent/diluent, desired product(s), reaction by-products, etc.) on the cooling surfaces can lessen the impact of fouling.

In another embodiment, any one or more of the methods according to the invention can advantageously utilize a metal-ligand complex, a catalyst, a catalyst system, reaction conditions, and/or a reaction system to provide an olefin selectivity to the desired olefin product relative to the total olefinic, non-polymeric product of at least 80 mol %, preferably at least 85 mol %, more preferably at least 90 mol %, at least 95 mol %, at least 96 mol %, at least 97 mol %, or at least 97.5 mol %, at least 98 mol %, at least 98.5 mol %, or at least 99 mol %. In certain preferred embodiments, the desired olefin product can be selected from the group consisting of 1-butene, 1-hexene, 1-octene, 1-decene, and mixtures thereof. In some embodiments, the desired olefin product can be a combination of all four of 1-butene, 1-hexene, 1-octene, 1-decene. In other embodiments, the desired olefin product can be any three selected from the group consisting of 1-butene, 1-hexene, 1-octene, and 1-decene. In some preferred embodiments, the desired olefin product can be any two selected from the group consisting of 1-butene, 1-hexene, 1-octene, and 1-decene. In other preferred embodiments, the desired olefin product can be selected from the group consisting of 1-butene, 1-hexene, 1-octene, and 1-decene.

A particularly useful catalyst system for selective oligomerization in the process described herein is formed from the combination of:

1) a ligand characterized by the following general formula:

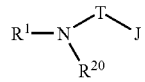

wherein:

$R^1$ and $R^{20}$ are each independently selected from the group consisting of consisting of hydrogen and optionally substituted hydrocarbyl, heteroatom containing hydrocarbyl and silyl (alternately $R^1$ and $R^{20}$ are each independently selected from the group consisting of: hydrogen and optionally substituted alkyl, heteroalkyl, cycloalkyl, heterocycloalkyl, aryl, heteroaryl, silyl and combinations thereof), provided that $R^1$ or $R^{20}$ do not equal T-J (alternately $R^1$ and $R^{20}$ are each independently a ring having from 4 to 8 atoms in the ring selected from the group consisting of substituted cycloalkyl, heterocycloalkyl, aryl and heteroaryl);

T is a bridging group, preferably represented by the formula -(T'R$^2$R$^3$)—, where T' is carbon or silicon, R$^2$ and R$^3$ are each independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, provided that two or more R$^2$ and/or R$^3$ groups may be joined together to form one or more optionally substituted ring systems having from 3 to 50 non-hydrogen atoms (for example, T is cyclopropyl, where T'=C, and R$^2$ and R$^3$ together form —CH$_2$—CH$_2$—; or T is cyclohexyl, where T'=C and the two R$^2$ groups together form —CH$_2$—CH$_2$—CH$_2$—CH$_2$—); and J is an optionally substituted six-membered heterocycle, containing at least one nitrogen atom as part of the ring, or J is an optionally substituted five-membered heterocycle, containing at least one nitrogen atom as part of the ring;

2) a metal precursor compound characterized by the general formula Cr(L)$_n$ where each L is independently selected from the group consisting of halide, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, wherein two or more L groups may be combined in a ring structure having from 3 to 50 non-hydrogen atoms; and n is 1, 2, 3, 4, 5, or 6; and 3) optionally, one or more activators.

In one embodiment, the ligand, as shown above, can be characterized by the following general formula, where J is a pyridyl or substituted pyridyl group:

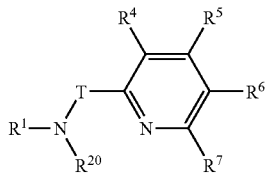

where R$^1$, R$^{20}$, and T are as described above; and R$^4$, R$^5$, R$^6$ and R$^7$ are independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, and optionally two or more R$^1$, R$^{20}$, R$^2$, R$^3$, R$^4$, R$^5$, R$^6$ and R$^7$ groups may be joined to form one or more optionally substituted ring systems.

In another embodiment, the ligand can be characterized by the following general formula:

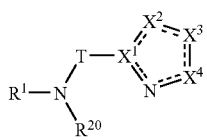

where R$^1$, R$^{20}$, and T are as described above; and X$^1$ is nitrogen or —C(R$^8$)$_{n''}$—, X$^2$, X$^3$, and X$^4$ are selected from the group consisting of oxygen, sulfur, —C(R$^8$)$_{n'}$—, —N(R$^8$)$_{n''}$—, and provided that at least one of X$^1$, X$^2$, X$^3$, or X$^4$ is carbon or —C(R$^8$)$_{n'}$—; each n' can be 1 or 2 and each n" can be 0 or 1; and, each R$^8$ can be independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, and optionally two or more R$^1$, R$^{20}$, R$^2$, R$^3$, and R$^8$ groups may be joined to form one or more optionally substituted ring systems.

In one embodiment, R$^1$ and R$^{20}$ are each independently selected from the group consisting of hydrogen and optionally substituted alkyl, heteroalkyl, aryl, heteroaryl, silyl and combinations thereof. In another embodiment, R$^1$ and R$^{20}$ are each independently a ring having from 4 to 8 atoms in the ring generally selected from the group consisting of substituted cycloalkyl, heterocycloalkyl, aryl, and heteroaryl.

In another embodiment (including all those described above), R$^{20}$ is hydrogen and R$^1$ is selected from the group consisting of alkyl, substituted alkyl, aryl, and substituted aryl.

In still another embodiment (including all those described above), R$^1$ and R$^{20}$ can each be independently selected from hydrogen and optionally substituted alkyl groups.

In yet another embodiment (including all those described above), R$^1$ and R$^{20}$ are joined in a ring structure having from 3 to 50 non-hydrogen atoms. In one variation of the immediately prior embodiment, the ring structure formed by the joining of R$^1$ and R$^{20}$ preferably does not include an optionally substituted heteroaryl ring having from 5 to 8 ring carbons, and more preferably does not include an optionally substituted pyrrolyl ring.

In another embodiment (including all those described above), R$^1$ is not hydrogen when R$^{20}$ is a cyclic group.

In still another embodiment (including all those described above), R$^{20}$ is not a hydrogen when R$^1$ is a cyclic group.

In another embodiment (including all those described above), R$^7$ is selected from the group consisting of optionally substituted aryl and heteroaryl.

In another embodiment (including all those described above), R$^2$ is hydrogen, and R$^3$ is selected from the group consisting of aryl, substituted aryl, heteroaryl, substituted heteroaryl, alkyl, and substituted alkyl groups, and —PY$_2$ where Y is selected from the group consisting of aryl, substituted aryl, heteroaryl, and substituted heteroaryl.

In some embodiments (including all those described above), R$^1$ is hydrogen and R$^{20}$ is selected from the group consisting of methyl, ethyl, propyl, butyl, pentyl, hexyl, octyl, decyl, docecyl, benzyl, and —CH$_2$CH$_2$Ph groups.

In some embodiments (including all those described above), R$^1$ and R$^{20}$ are each independently selected from the group consisting of methyl, ethyl, propyl, butyl, pentyl, hexyl, octyl, decyl, docecyl, benzyl, and —CH$_2$CH$_2$Ph groups.

In some embodiments (including all those described above), R$^5$ is selected from the group consisting of —CF$_3$, —H, —F, —Cl, —N(Me)$_2$ and —OR, wherein R is an optionally substituted alkyl group, an optionally substituted benzyl group, or an optionally substituted aryl group.

In some embodiments (including all those described above), R$^3$ is selected from the group consisting of hydrogen and optionally substituted alkyl, heteroalkyl, cycloalkyl, heterocycloalkyl, silyl, and combinations thereof.

The heterocycle-amine ligands, such as pyridyl-amine ligands, described herein can be prepared according to the procedures known to those of ordinary skill in the art, for example, as described in U.S. Pat. Nos. 6,750,345 and 6,713, 577, and as described in U.S. patent application Ser. Nos. 11/371,614 and 11/371,983, the disclosures of all of which are incorporated by reference herein.
Preferred ligands for use herein include pyridyl-amine ligands A1-A75 as seen in the attached figures, especially ligands A4, A5, A23, A28, A29, A30, and A38.
Preferred ligands useful herein also include those represented by the following formulae:
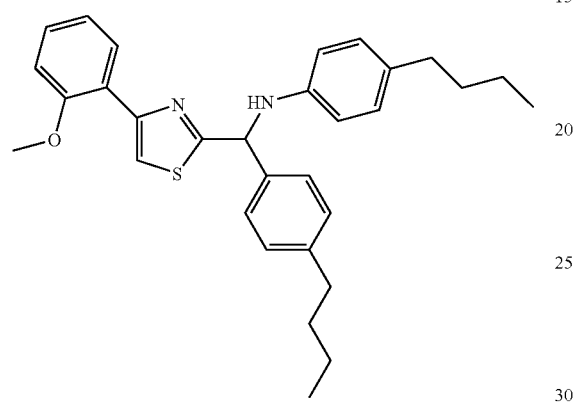
B1
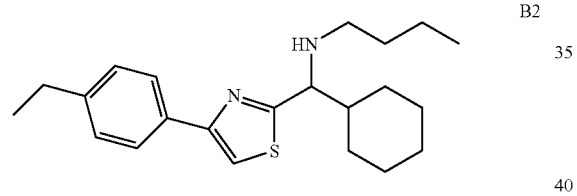
B2
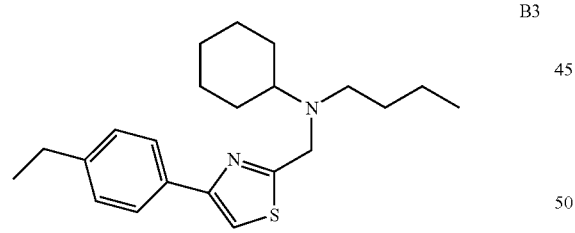
B3
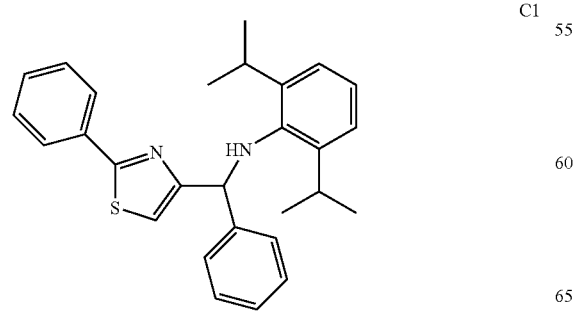
C1
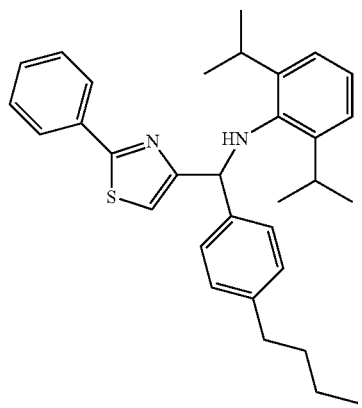
C2
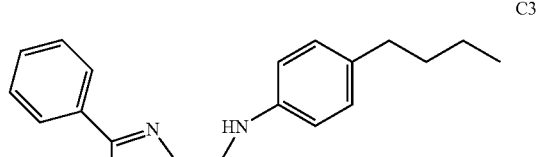
C3
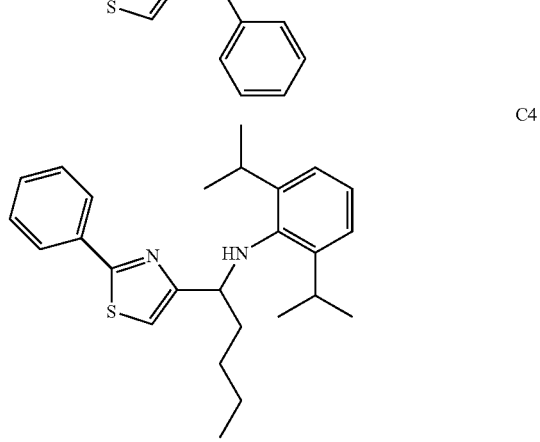
C4
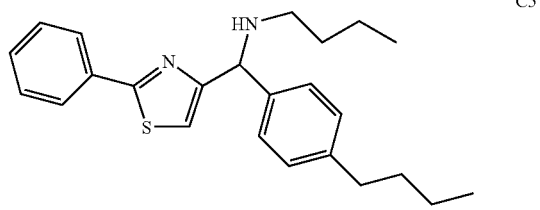
C5
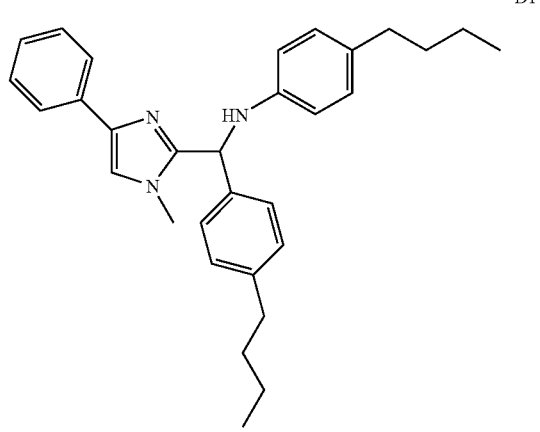
D1

-continued
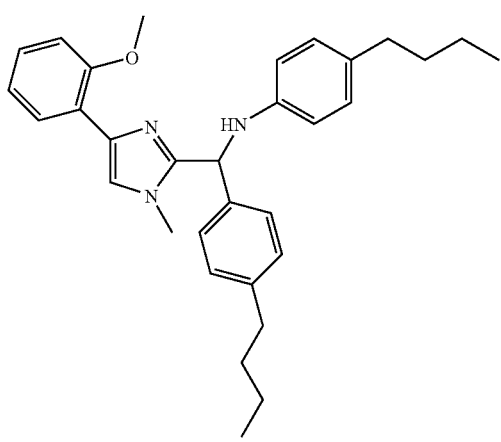
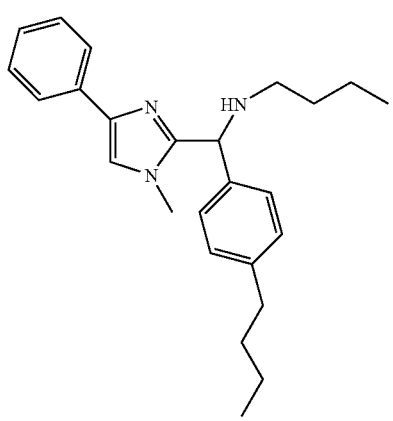
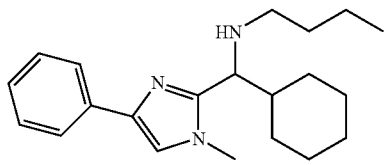
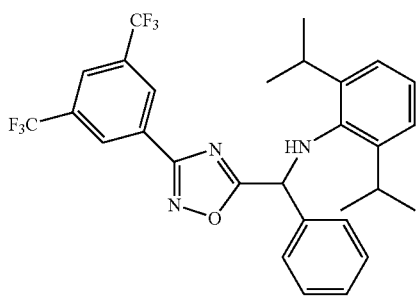
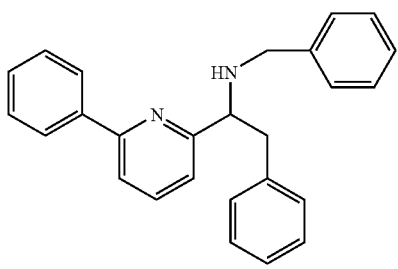
-continued
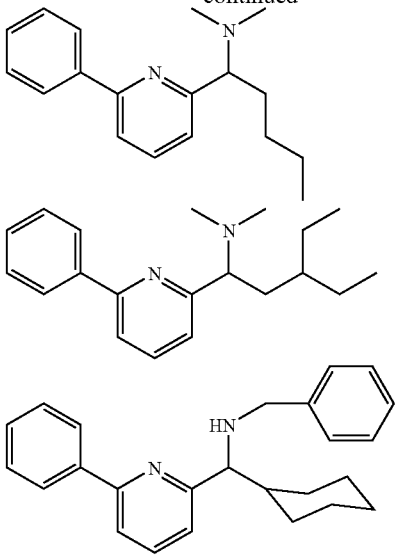
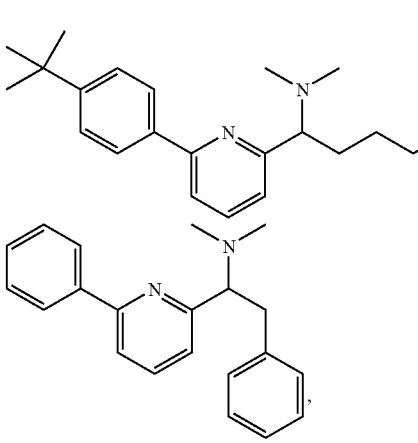
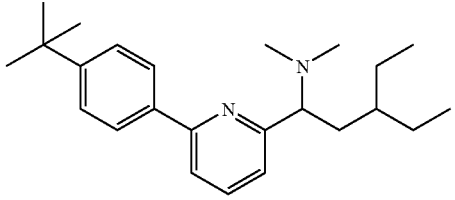
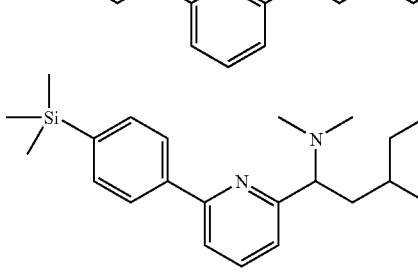
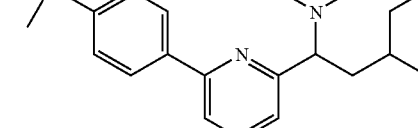
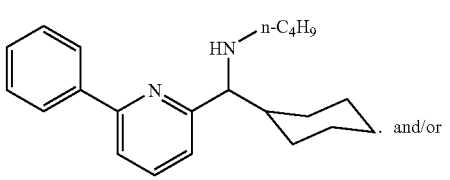
, and/or Particularly useful trimerization ligands useful herein include:

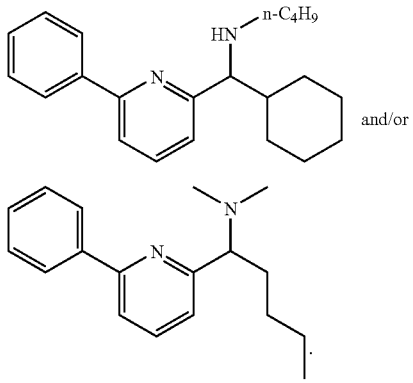

DIPAMP

Another useful catalyst and/or catalyst system for oligomerization of olefins (preferably the trimerization or tetramerization of $C_2$ to $C_{12}$ olefins, such as ethylene) useful herein is formed from the combination of:

1) at least one ligand represented by the formula:

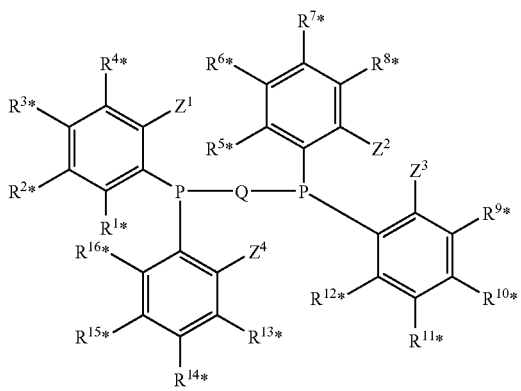

wherein

P is phosphorus;

each of $R^{1*}$, $R^{2*}$, $R^{3*}$, $R^{4*}$, $R^{5*}$, $R^{6*}$, $R^{7*}$, $R^{8*}$, $R^{9*}$, $R^{10*}$, $R^{11*}$, $R^{12*}$, $R^{13*}$, $R^{14*}$, $R^{15*}$, and $R^{16*}$ is, independently, selected from the group consisting of hydrogen, halogen, optionally substituted hydrocarbyl, and optionally substituted heteroatom containing hydrocarbyl;

each of $Z^1$, $Z^2$, $Z^3$ or $Z^4$ is, independently, selected from a first group consisting of hydrogen, a hydrocarbyl, alkoxy, aryloxy, alkylthio, arylthio, hydroxyl, mercapto, and amino, (preferably at least two and less than all four of $Z^1$, $Z^2$, $Z^3$, and $Z^4$ are selected from a second group consisting of alkoxy, aryloxy, alkylthio, arylthio, hydroxyl, mercapto, and amino; in alternate embodiments, $Z^1$, $Z^2$, $Z^3$ and $Z^4$ may not all be methoxy; in still further embodiments, either of the pairs of $Z^1$ and $Z^2$ or $Z^3$ and $Z^4$ are not both selected from the second group); and Q is a bridging group selected from the group consisting of optionally substituted hydrocarbyl having from 2 to 20 carbon atoms;

2) a metal precursor characterized by the general formula $Cr(L)_n$ where each L is independently selected from the group consisting of halide, alkyl, substituted alkyl, cycloalkyl, substituted cycloalkyl, heteroalkyl, substituted heteroalkyl heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, wherein two or more L groups may be combined in a ring structure having from 3 to 50 non-hydrogen atoms, and wherein n is 1, 2, 3, 4, 5, or 6; and 3) optionally, one or more activators.

In alternate embodiments, Q can be a hydrocarbyl bridge formed by an aryl or cycloalkyl group. For example, such aryl or cycloalkyl bridging groups include phenyl, naphthyl, biphenyl, and cyclohexyl. In certain embodiments, the phosphorus atoms are connected apart from each other by two, three, four, five, or six carbon bonds. For example, when a phenyl or cyclohexyl group is Q, the phosphorus atoms can be attached 1,2 or 1,3 or 1,4 relative to each other (i.e., ortho, meta, or para, respectively).

In some embodiments, when $Z^1$, $Z^2$, $Z^3$, and $Z^4$ are each methoxy and Q is an ethylene or methylene bridge, the metal precursor is not $CrCl_3(THF)_3$;

In another alternate embodiment, three of $Z^1$, $Z^2$, $Z^3$, and $Z^4$ are, independently, selected from the group consisting alkoxy, aryloxy, alkylthio, arylthio, hydroxyl, mercapto, and amino, and one of $Z^1$, $Z^2$, $Z^3$, and $Z^4$ is, independently, selected from the group consisting of hydrogen and hydrocarbyl.

In another alternate embodiment, each of $Z^1$, $Z^2$, $Z^3$, and $Z^4$ is, independently, selected from the group consisting alkoxy, aryloxy, alkylthio, arylthio, hydroxyl, mercapto, and amino, further provided that $Z^1$, $Z^2$, $Z^3$, and $Z^4$ may not all be methoxy.

In some embodiments, $Z^1$, $Z^2$, $Z^3$, and $Z^4$ are, independently selected from the group consisting of methoxy, ethoxy, propoxy, isopropoxy, butoxy, isobutoxy, tert-butoxy, pentoxy, phenoxy, methylthio, ethylthio, propylthio, isopropylthiio, butylthio, isobutylthio, tert-butylthio, phenylthio, dimethylamino, diethylamino, dipropylamino, diisopropylamino, dibutylamino, diisobutylamino, hydroxyl, and mercapto.

In some embodiments, Q has from 2 to 16 carbon atoms, and is preferably selected from the group consisting of ethyl, propyl, butyl, pentyl, hexyl, cyclohexyl, heptyl, tolyl, octyl, nonyl, decyl, phenyl, naphthyl, and dodecyl.

In some embodiments, each of $R^{1*}$, $R^{2*}$, $R^{3*}$, $R^{4*}$, $R^{5*}$, $R^{6*}$, $R^{7*}$, $R^{8*}$, $R^{9*}$, $R^{10*}$, $R^{11*}$, $R^{12*}$, $R^{13*}$, $R^{15*}$, $R^{15*}$, and $R^{16*}$ is, independently, selected from the group consisting of hydrogen, a hydrocarbyl group having 1 to 20 carbon atoms, a substituted hydrocarbyl group having 1 to 20 carbon atoms, and a halogen.

In some embodiments, each of $Z^1$, $Z^2$, $Z^3$, and $Z^4$ is, independently, hydrogen, alkoxy, aryloxy, alkylthio, arylthio, hydroxyl, mercapto, or amino, where the alkyl substituent(s), if present, is(are) a $C_1$ to $C_{20}$ hydrocarbyl group, and the aryl substituent(s), if present, is(are) a $C_5$ to $C_{20}$ hydrocarbyl group, and wherein each hydrocarbyl group is preferably selected from the group consisting of methyl, ethyl, propyl, butyl, pentyl, hexyl, cyclohexyl, heptyl, tolyl, octyl, nonyl, decyl, phenyl, napthyl, benzyl, tolyl, and dodecyl.

In a preferred embodiment, one, two, three, or all four of $Z^1$, $Z^2$, $Z^3$, and $Z^4$ are selected from the group consisting of alkoxy, aryloxy, alkylthio, arylthio, hydroxyl, mercapto, and amino. In another preferred embodiment, one, two, three, or all four of $Z^1$, $Z^2$, $Z^3$, and $Z^4$ are an alkoxy, preferably methoxy.

A specific group of ligands useful in this invention include those represented by the formulae:

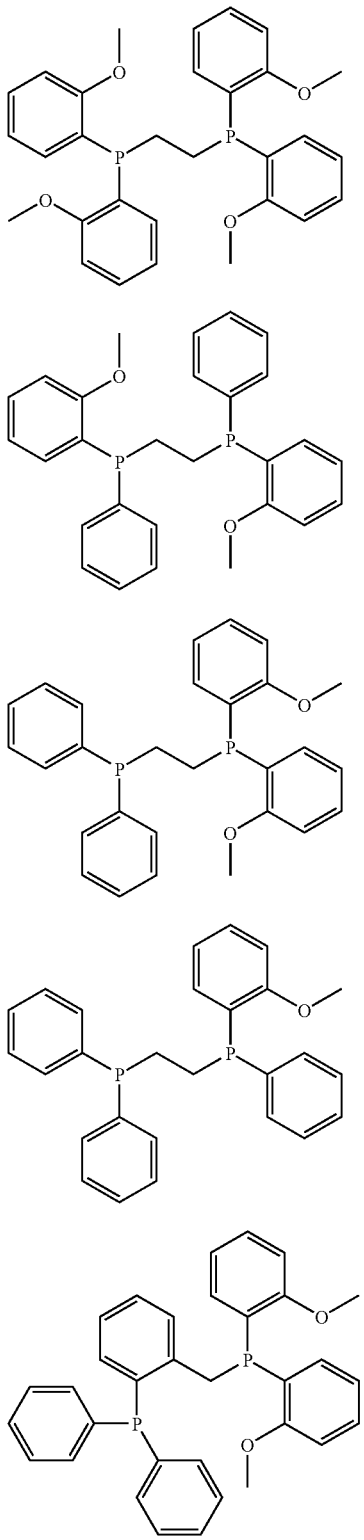

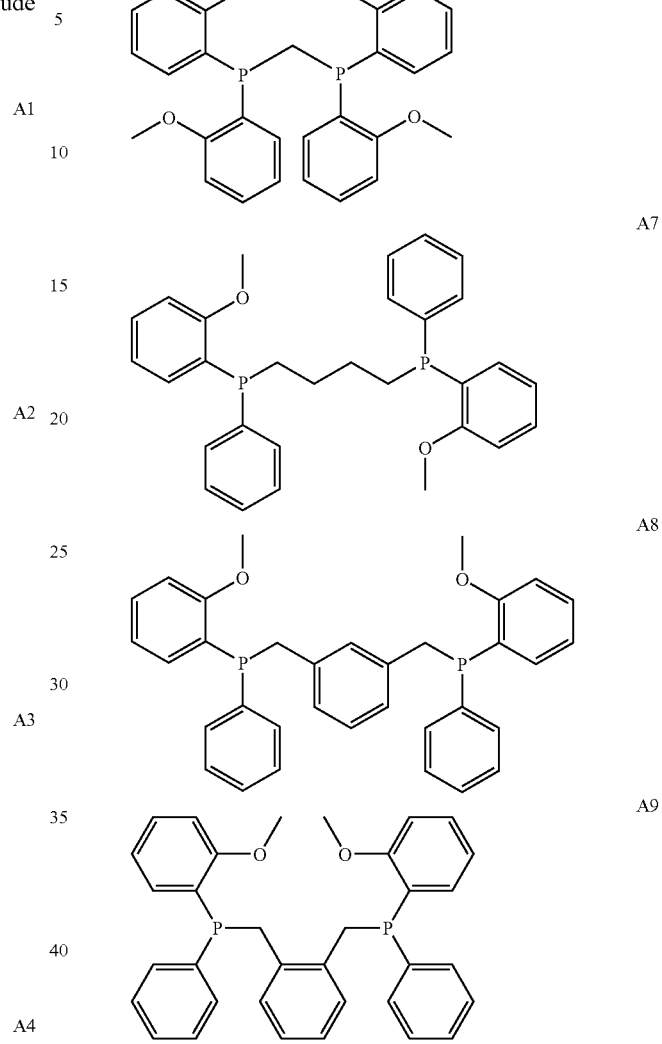

A particularly preferred ligand is $Ar_2PCH_2CH_2P(2\text{-}MeOPh)_2$, wherein Ar is arene, Me is methyl, and Ph is phenyl. Another preferred ligand is (ortho-methoxyphenyl)$_2$P—$CH_2$—$CH_2$—P(ortho-methoxyphenyl)$_2$.

Methods to prepare such ligands are discussed, for example, in U.S. Patent Application Ser. No. 60/841,226, filed Aug. 30, 2006, assigned to ExxonMobil Chemical Patents Inc., the contents of which are incorporated herein by reference.

In certain embodiments when the catalyst precursor is $CrCl_3(THF)_3$, the ligand is not A1 or A6. Alternately in some embodiments, when the catalyst precursor is $CrCl_3(THF)_3$, the ligand is A1 or A6, and then the activator is modified methylalumoxane ("MMAO") and/or methylalumoxane ("MAO").

More specific ligands useful in the invention include: $Ar_2PCH_2CH_2P(2\text{-}MeOPh)_2$, where Ar is arene (in particular Ar is Ph, 2-MePh, 2,6-Me2Ph, 2,4,6-Me3Ph, 1-Naphthyl, or 2-Naphthyl), Me is methyl, and Ph is phenyl.

Where asymmetric substitution at the phosphine leads a chiral center, pure enantiomers, pure diastereomers, or mixtures thereof may be used.

Metal Precursor

Once the desired ligand is formed, it can be combined with a Cr atom, ion, compound, or other Cr precursor compound, and, in some embodiments, the present invention encompasses compositions that include any of the above-mentioned ligands, in combination with an appropriate Cr precursor and an optional activator.

Particularly useful Cr metal precursor compounds are represented by the formula $Cr(L)_n$, where L is an organic group, an inorganic group, or an anionic atom, and where n is an integer of 1 to 6, and, when n is not less than 2, each L may be the same or different from each other. Each L is a ligand independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulfate, and combinations thereof. Optionally, two or more L groups can be joined into a ring structure. One or more of the ligands L may be ionically bonded to Cr and, for example, L may be a non-coordinated, loosely-coordinated, or weakly-coordinated anion (e.g., L may be selected from the group consisting of those anions described below in the conjunction with the activators). See Marks et al., *Chem. Rev.* 100, pp 1391-1434 (2000) for a detailed discussion of these weak interactions. The chromium precursors may be monomeric, dimeric, or higher orders thereof.

In a preferred embodiment, each L is independently a hydrocarbyl, halide, alkoxy, carboxylate, diaonate, amino, ether, or amine. In an alternate embodiment, each L is independently chloride, mesityl, tetrahydrofuran, methyl, ethyl, butyl, pentyl, hexyl, octyl, phenyl, $Et_2O$, $NH_3$, $NMe_3$, acetylacetonate, 2-ethylhexanoate, neopentyl, $SMe_2$, $CH_2-C_6H_4$-o-$NMe_2$, trifluoroacetate, $CH(SiMe_3)_2$, p-tolyl, diisopropylamide, picolinate, or $NO_3$, where Et is ethyl and Me is methyl.

Specific examples of suitable chromium precursors include, but are not limited to, $(THF)_3CrMeCl_2$, $(Mes)_3Cr(THF)$, $[\{TFA\}_2Cr(OEt_2)]_2$, $(THF)_3CrPh_3$, $CrCl_3(THF)_3$, $CrCl_4(NH_3)_2$, $Cr(NMe_3)_2Cl_3$, $CrCl_3$, $Cr(acac)_3$, $Cr(2\text{-ethyl-hexanoate})_3$, $Cr(neopentyl)_4$, $Cr(CH_2-C_6H_4\text{-o-}NMe_2)_3$, $Cr(TFA)_3$, $Cr(CH(SiMe_3)_2)_3$, $Cr(Mes)_2(THF)_3$, $Cr(Mes)_2(THF)$, $Cr(Mes)Cl(THF)_2$, $Cr(Mes)Cl(THF)_{0.5}$, $Cr(p\text{-tolyl})Cl_2(THF)_3$, $Cr(diisopropylamide)_3$, $Cr(picolinate)_3$, $[Cr_2Me_8][Li(THF)]_4$, $CrCl_2(THF)$, $Cr(NO_3)_3$, $[CrMe_6][Li(Et_2O)]_3$, $[CrPh_6][Li(THF)]_3$, $[CrPh6][Li(n\text{-}Bu_2O)]_3$, $[Cr(C_4H_8)_3][Li(THF)]_3$, and other well known chromium compounds commonly used as precursors in the formation of Cr complexes and catalysts.

Preferred metal precursors used herein can be selected from the group consisting of $(THF)_3CrMeCl_2$, $(THF)_3CrCl_3$, $(Mes)_3Cr(THF)$, $[\{TFA\}_2Cr(OEt_2)]_2$, $(THF)_3CrPh_3$, and mixtures thereof.

The ligand may be mixed with a metal precursor compound prior to, or simultaneously with, allowing the mixture to be contacted with the reactants (e.g., monomers). The ligand to metal precursor compound ratio can be in the range of about 0.01:1 to about 100:1, more specifically in the range of about 0.1:1 to about 10:1.

Cr-ligand complexes can take a number of different coordination modes. General examples of possible coordination modes include those characterized by the following general formulas:

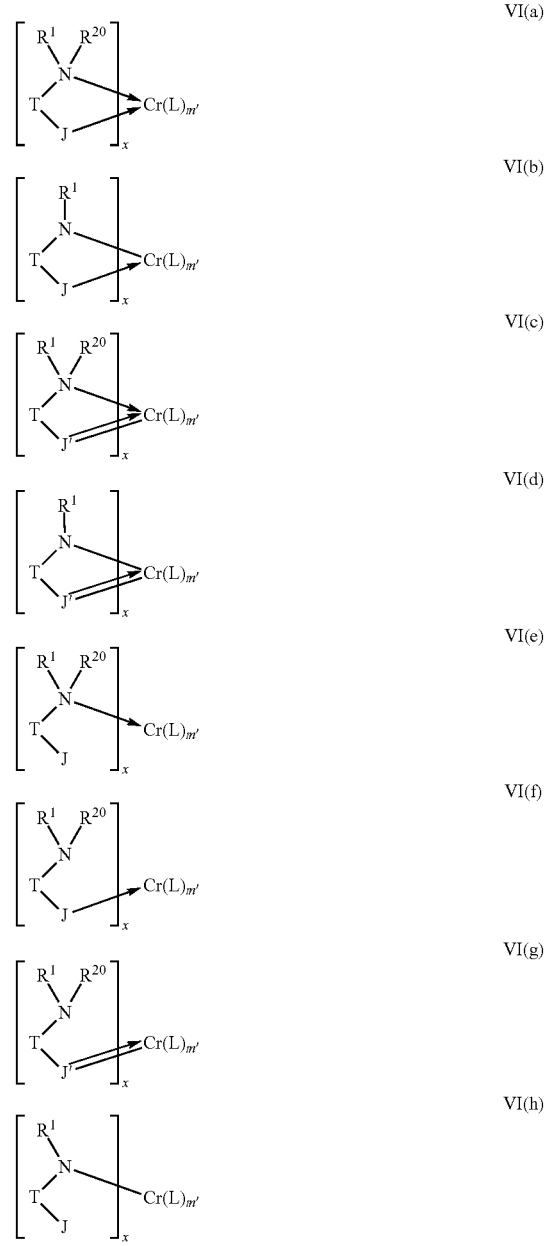

wherein $R^1$, $R^{20}$, L, J, and T are described above; wherein x is 1 or 2; and wherein m' is 1, 2, 3, 4, or 5. J' is defined the same as J is defined above, provided that J' includes 2 atoms bonded to the Cr, one of the which is in the ring position adjacent to the atom bonded to T, which is bonded to Cr through a dative bond, and the other of which is bonded to the Cr through a covalent bond. Numerous other coordination modes are possible, for example the ligands may bind to two chromium metal centers in a bridging fashion (see, for example, Cotton and Walton, *Multiple Bonds Between Metal Atoms* 1993, Oxford University Press).

In some embodiments, the ligand may be mixed with a suitable metal precursor prior to, or simultaneous with, allowing the mixture to be contacted to the reactants. When the ligand is mixed with the metal precursor, a metal-ligand complex can be formed. In connection with the metal-ligand complex and depending on the ligand(s) chosen, the metal-ligand complex may take the form of dimers, trimers, or higher orders thereof, or there may be two or more metal atoms that are bridged by one or more ligands. Furthermore, two or more ligands may coordinate with a single metal atom. The exact nature of the metal-ligand complex(es) formed can depend on the chemistry of the ligand and on the method of combining the metal precursor and ligand, such that a distribution of metal-ligand complexes may form, with the number of ligands bound to the metal being greater than, equal to, or less than the number of equivalents of ligands added relative to an equivalent of metal precursor.

In one embodiment, metal ligand complexes (such as the Cr-ligand complex described above) can advantageously coordinate such that the metal (e.g., Cr) is associated with (e.g., covalently and/or datively bonded to) the nitrogen atom (N), one or more atoms of the J or J' moiety, or both. Additionally or alternately, when $R^1$ and $R^{20}$ are joined in a ring structure having from 3 to 50 non-hydrogen atoms, the metal (e.g., Cr) of the metal ligand complex (e.g., the Cr-ligand complex) is preferably not associated with (e.g., covalently and/or datively bonded to) any atom(s) other than the nitrogen atom (N) on the ring formed by N, $R^1$, and $R^{20}$.

In one embodiment, the metal complex is represented by the formula:

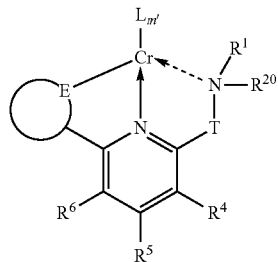

wherein $R^1$, $R^4$, $R^5$, $R^6$, $R^{20}$, T, L, and m' are as described above; and E is a carbon atom that is part of an optionally substituted aryl or heteroaryl ring. In one aspect, the aryl or heteroaryl ring may be polycyclic.

Listed below are some non-limiting examples of Cr-Ligand complex embodiments useful herein:

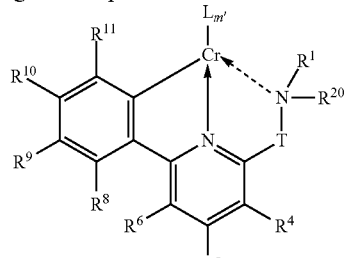

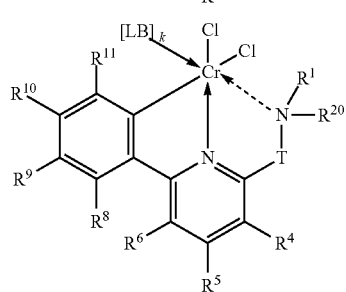

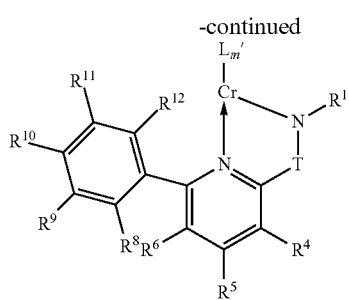

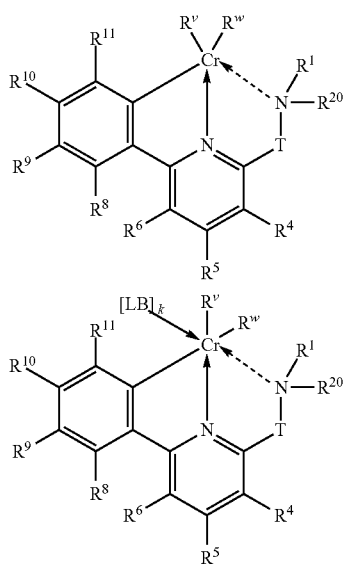

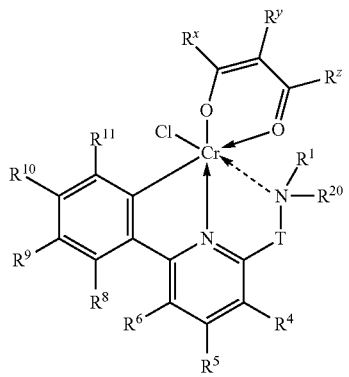

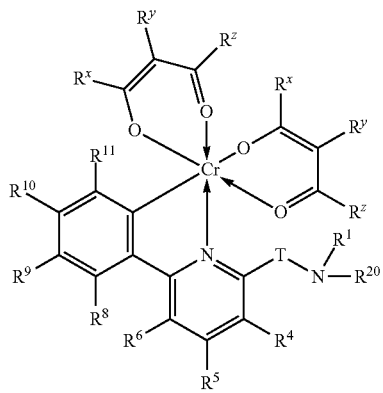

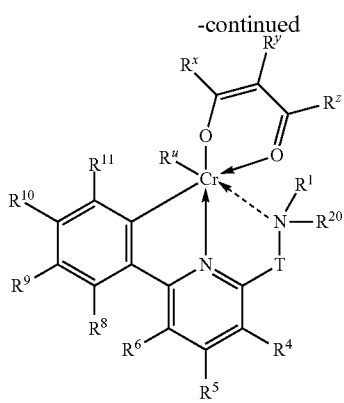

wherein
R$^1$, R$^2$, R$^3$, R$^4$, R$^5$, R$^6$, R$^{20}$, T, L, and m' are as defined above;

R$^8$ R$^9$, R$^{10}$, R$^{11}$, and R$^{12}$ are independently selected from the group consisting of hydrogen, halogen, nitro, optionally substituted alkyl, heteroalkyl, aryl, heteroaryl, alkoxy, aryloxy, silyl, boryl, phosphino, amino, alkylthio, and arylthio, and combinations thereof; and optionally two or more R$^8$ R$^9$, R$^{10}$, R$^{11}$, and R$^{12}$ groups may be joined to form one or more optionally substituted ring systems;

R$^u$, R$^v$, R$^w$, R$^x$, R$^y$, and R$^z$ are optionally substituted alkyl, heteroalkyl, aryl, and/or heteroaryl moieties;

a dashed arrow indicates that the dative bond is an optional bond, which may or may not be present; and LB is a Lewis base; and k=0 or 1.

Some specific embodiments of Cr-Ligand complexes useful herein are shown below:

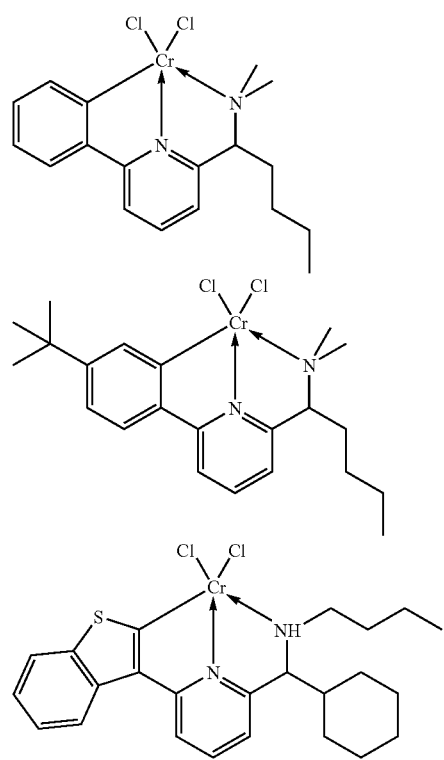

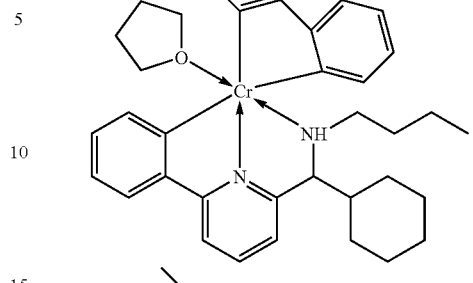

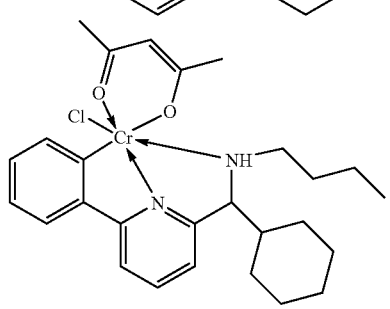

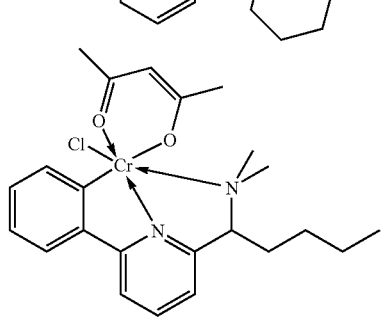

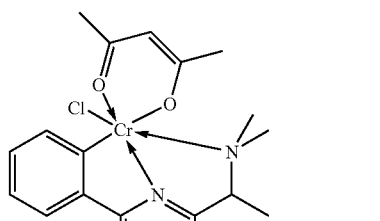

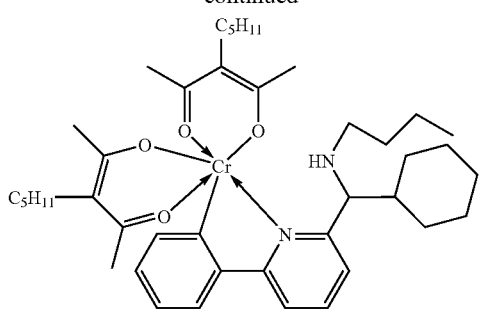

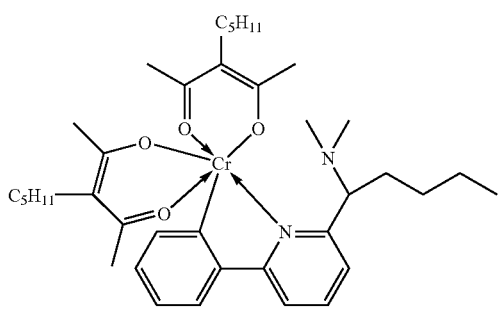

In still further embodiments, Cr-ligand complexes can take a number of different coordination modes. General examples of possible coordination modes include those represented by the formulae:

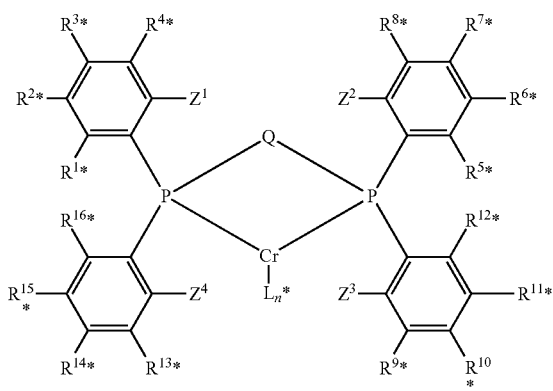

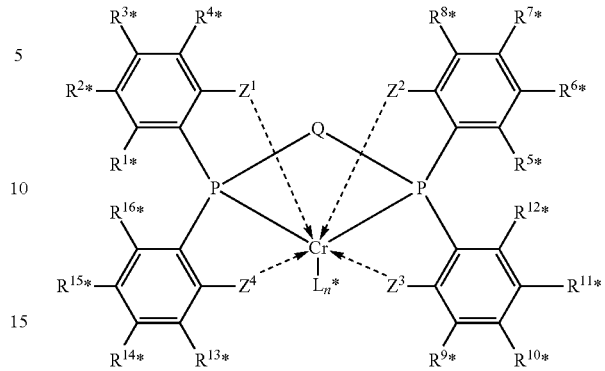

wherein n*=0, 1, 2, 3, or 4, and wherein $R^{1*}$ to $R^{16*}$, Q, L, and $Z^1$ to $Z^4$ are as defined above. In a preferred embodiment of formula 2, any one or more of $Z^1$, $Z^2$, $Z^3$, and $Z^4$ may form a dative bond to the chromium. In certain circumstances, for instance, during catalysis, the formation of the dative bonds may be reversible.

Further specific examples of Cr-ligand complexes useful in the invention are shown below:

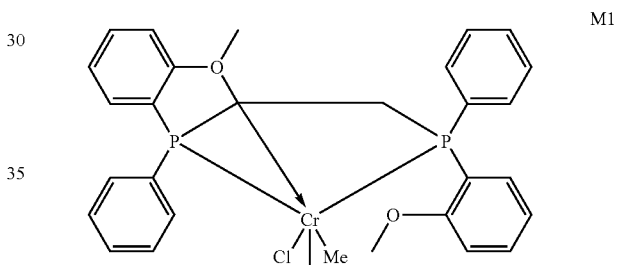

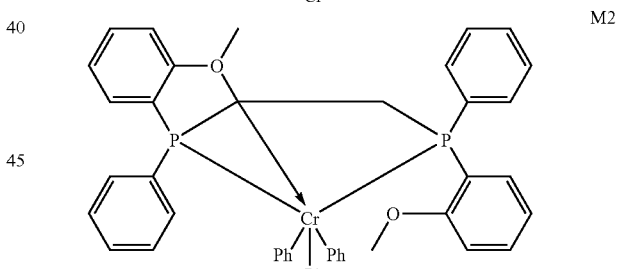

Further description of such complexes and how to prepare them is disclosed in U.S. Patent Application Ser. No. 60/841,226, filed Aug. 30, 2006, assigned to ExxonMobil Chemical Patents Inc., the entire contents of which are hereby incorporated by reference.

Activators

The ligand-metal-precursor combinations and the metal ligand complexes, described above, are optionally activated in various ways to yield compositions active for selective oligomerization (preferably ethylene oligomerization). For the purposes of this patent specification and appended claims, the terms "cocatalyst" and "activator" are used herein interchangeably and are defined to be any compound which can activate any one of the ligands-metal-precursor-combinations and the metal ligand complexes described above by converting the combination, complex, or composition into a catalytically active species. Non-limiting activators, for example, include alumoxanes, aluminum alkyls, other metal or main group alkyl or aryl compounds, ionizing activators, which may be neutral or ionic, Lewis acids, reducing agents, oxidizing agents, and combinations thereof.

In one embodiment, alumoxane activators are utilized as an activator in the compositions useful in the invention. Alumoxanes are generally oligomeric compounds containing —Al(R*)—O— sub-units, where R* is an alkyl group. Examples of alumoxanes include methylalumoxane (MAO), ethylalumoxane, isobutylalumoxane, and modified methylalumoxanes (MMAO), which include alkyl groups other than methyl such as ethyl, isobutyl, and n-octyl, such as MMAO-3A, PMAO-IP (referring to polymethylalumoxane, improved process, manufactured by Akzo-Nobel and meaning an MAO prepared from a non-hydrolytic process). Alkylalumoxanes and modified alkylalumoxanes are suitable as catalyst activators, particularly when the abstractable ligand of the catalyst is a halide, alkoxide, or amide. Mixtures of different alumoxanes and modified alumoxanes may also be used. For further descriptions on production and use of alumoxanes, see U.S. Pat. Nos. 4,665,208, 4,874,734, 4,908,463, 4,924,018, 4,952,540, 4,968,827, 5,041,584, 5,091,352, 5,103,031, 5,157,137, 5,204,419, 5,206,199, 5,235,081, 5,248,801, and 5,329,032; see also European Publication Nos. EP 0 561 476 A1, EP 0 279 586 B1, EP 0 516 476 A1, and EP 0 594 218 A1; see also International Publication No. WO 94/10180.

When the activator is an alumoxane (modified or unmodified), some embodiments select the maximum amount of activator at a 5000-fold molar excess Al/Cr over the catalyst precursor. The minimum preferred activator-to-catalyst-precursor is a 1:1 molar ratio. More specifically, the Al/Cr ratio can be from 1000:1 to 100:1.

It may be preferable to use a visually clear methylalumoxane. A cloudy or gelled alumoxane can be filtered to produce a clear solution, or clear alumoxane can be decanted from the cloudy solution. Another particularly useful alumoxane is a modified methyl alumoxane (MMAO) cocatalyst type 3A (commercially available from Akzo Chemicals, Inc., under the trade name Modified Methylalumoxane type 3A, and disclosed in U.S. Pat. No. 5,041,584).

Aluminum alkyl or organoaluminum compounds which may be utilized as activators (or scavengers) include, but are not limited to, trimethylaluminum, triethylaluminum, triisobutylaluminum, tri-n-hexylaluminum, tri-n-octylaluminum, diisobutylaluminum hydride, ethylaluminum dichloride, diethylaluminum chloride, diethylaluminum ethoxide, and the like.

Ionizing Activators

In some embodiments, the activator includes compounds that may abstract a ligand making the metal complex cationic and providing a charge-balancing non-coordinating or weakly-coordinating anion. The term "non-coordinating anion" (NCA) means an anion which either does not coordinate to said cation or which is only weakly coordinated to said cation, thereby remaining sufficiently labile to be displaced by a neutral Lewis base.

It is within the scope of this invention to use an ionizing or stoichiometric activator, neutral or ionic, such as tri-(n-butyl)-ammonium tetrakis(pentafluorophenyl)boron, a tris(perfluorophenyl)boron metalloid precursor, or a tris(perfluoronaphthyl)boron metalloid precursor, polyhalogenated heteroborane anions (International Publication No. WO 98/43983), boric acid (U.S. Pat. No. 5,942,459), or a combination thereof. It is also within the scope of this invention to use neutral or ionic activators alone or in combination with alumoxane or modified alumoxane activators.

Examples of neutral stoichiometric activators include, but are not limited to, tri-substituted boron, tellurium, aluminum, gallium, and indium, or mixtures thereof. The three substituent groups of the tri-substituted metal can each be independently selected from alkyls, alkenyls, halogens, substituted alkyls, aryls, arylhalides, alkoxyls, and halides. In some embodiments, the three substituent groups can be independently selected from halogen, mono or multicyclic (including halosubstituted) aryls, alkyls, and alkenyl compounds, and mixtures thereof; preferred include alkenyl groups having 1 to 20 carbon atoms, alkyl groups having 1 to 20 carbon atoms, alkoxy groups having 1 to 20 carbon atoms, and aryl groups having 3 to 20 carbon atoms (including heteroaryls and substituted aryls). In other embodiments, one or more of the three substituent groups can be alkyls having 1 to 4 carbon groups, phenyls, naphthyls, or mixtures thereof. In further embodiments, one or more of the three substituent groups can be halogenated, specifically fluorinated, aryl groups. In even further embodiments, the neutral stoichiometric activator can be tris(perfluorophenyl)boron or tris(perfluoronaphthyl)boron.

Ionic stoichiometric activator compounds may contain an active proton, or some other cation associated with, but not coordinated to, or only loosely coordinated to, the remaining ion of the ionizing compound. Such compounds and the like are described in European Publication Nos. EP 0 277 003 A1, EP 0 277 004 A1, EP 0 495 375 A1, EP 0 500 944 B1, EP 0 520 732 A1, and EP 0 570 982 A1; in U.S. Pat. Nos. 5,066,741, 5,153,157, 5,198,401, 5,206,197, 5,241,025, 5,384,299, and 5,502,124; and in U.S. patent application Ser. No. 08/285,380, filed Aug. 3, 1994, the entire disclosure of each of which is herein fully incorporated by reference.

Ionic catalysts can be prepared by reacting a metal (e.g., Cr) compound with some neutral Lewis acids, such as $B(C_6F_6)_3$, which, upon reaction with the abstractable ligand (X) of the metal (e.g., Cr) compound, can form an anion, such as $([B(C_6F_5)_3(X)]^-)$, which can stabilize the cationic metal (e.g., Cr) species generated by the reaction. The catalysts can be prepared with activator components which are ionic compounds or compositions.

In some embodiments, compounds useful as an activator component in the preparation of the ionic catalyst systems used in the process of this invention can comprise a cation, which is optionally a Brönsted acid capable of donating a proton, and a compatible non-coordinating anion, which is capable of stabilizing the active catalyst species, and which can be formed when the two compounds are combined, and said anion will typically be sufficiently labile to be displaced by olefinic substrates or other neutral Lewis bases, such as ethers, nitrites, and the like. Two classes of compatible non-coordinating anions useful herein have been disclosed in European Publication Nos. EP 0 277 003 A1 and EP 0 277 004 A1, both published in 1988 (anionic coordination complexes comprising a plurality of lipophilic radicals covalently coordinated to and shielding a central charge-bearing metal or metalloid core, and anions comprising a plurality of boron atoms such as carboranes, metallacarboranes, and boranes).

In one preferred embodiment, the stoichiometric activators include a cation and an anion component, and may be represented by the following formula:

$$(L-H)_d^+(A^{d-})$$

wherein: L is a neutral Lewis base; H is hydrogen; $(L-H)_d^+$ is a Brönsted acid; $A^{d-}$ is a non-coordinating anion having the charge d−; and d is an integer from 1 to 3.

The cation component $(L-H)_d^+$ may include Brönsted acids such as protons, protonated Lewis bases, or reducible Lewis acids capable of protonating or abstracting a moiety, such as an alkyl or aryl, from the bulky ligand chromium catalyst precursor, resulting in a cationic transition metal species.

The activating cation $(L–H)_d^+$ may be a Brönsted acid, capable of donating a proton to the transition metal catalytic precursor resulting in a transition metal cation, can include, but is not limited to, ammoniums, oxoniums, phosphoniums, silyliums, and mixtures thereof, specifically ammoniums of methylamine, aniline, dimethylamine, diethylamine, N-methylaniline, diphenylamine, trimethylamine, triethylamine, N,N-dimethylaniline, methyldiphenylamine, pyridine, p-bromo-N,N-dimethylaniline, and/or p-nitro-N,N-dimethylaniline, phosphoniums from triethylphosphine, triphenylphosphine, and/or diphenylphosphine, oxoniums from ethers such as dimethyl ether, diethyl ether, tetrahydrofuran, and/or dioxane, sulfoniums from thioethers such as diethyl thioethers and/or tetrahydrothiophene, and mixtures thereof. The activating cation $(L–H)_d^+$ may also be a moiety such as silver, tropylium, a carbenium, a carbonium, a ferrocenium, and a mixture thereof, specifically a carbonium and/or a ferrocenium. In one embodiment $(L–H)_d^+$ can be triphenyl carbonium.

The anion component $A^{d−}$ can include those having the formula $[M^{k+}Q_n]^{d−}$ wherein k is an integer from 1 to 3; n is an integer from 2-6; n−k=d; M is an element selected from Group 13 of the Periodic Table of the Elements, specifically boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms, with the proviso that in not more than 1 occurrence is Q a halide. Specifically, each Q can be a fluorinated hydrocarbyl group having 1 to 20 carbon atoms, more specifically a fluorinated aryl group, and most specifically a pentafluoryl aryl group. Additionally or alternately, non-limiting examples of suitable $A^{d−}$ also include diboron compounds, as disclosed in U.S. Pat. No. 5,447,895, which is fully incorporated herein by reference.

Illustrative, but not limiting, examples of boron compounds that may be used as an activating cocatalyst herein include tri-substituted ammonium salts such as: trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium)tetraphenylborate, tropillium tetraphenylborate, triphenylcarbenium tetraphenylborate, triphenylphosphonium tetraphenylborate, triethylsilylium tetraphenylborate, benzene(diazonium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis(pentafluorophenyl)borate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium)tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl) borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium)tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium)tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium)tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium)tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(t-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl)phenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene (diazonium) tetrakis(3,5-bis(trifluoromethyl)phenyl)borate, dialkyl ammonium salts such as di-(i-propyl)ammonium tetrakis(pentafluorophenyl)borate and dicyclohexylammonium tetrakis(pentafluorophenyl)borate, additional tri-substituted phosphonium salts such as tri(o-tolyl)phosphonium tetrakis(pentafluorophenyl)borate and tri(2,6-dimethylphenyl)phosphonium tetrakis(pentafluorophenyl)borate, and mixtures thereof.

Specifically useful ionic stoichiometric activators can include, but are not limited to N,N-dimethylanilinium tetra (perfluorophenyl)borate, N,N-dimethylanilinium tetrakis (perfluoronaphthyl)borate, N,N-dimethylanilinium tetrakis (perfluorobiphenyl)borate, N,N-dimethylanilinium tetrakis (3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis (3,5-bis(trifluoromethyl)phenyl)borate, triphenylcarbenium tetrakis(perfluorophenyl)borate, and mixtures thereof.

Other examples of preferred ionizing activators can include, but are not limited to, $HNMe(C_{18}H_{37})_2{}^+B(C_6F_5)_4{}^-$, $HNPh(C_{18}H_{37})_2{}^+B(C_6F_5)_4{}^-$, $((4\text{-n-Bu-}C_6H_4)NH(\text{n-hexyl})_2)^+B(C_6F_5)_4{}^-$, and $((4\text{-n-Bu-}CH_4)NH(\text{n-decyl})_2)^+B(C_6F_5)_4{}^-$. Specific preferred $(L^*\text{-H})^+$ cations include N,N-dialkylanilinium cations such as $HNMe_2Ph^+$, substituted N,N-dialkylanilinium cations such as $(4\text{-n-Bu-}C_6H_4)NH(\text{n-}C_6H_{13})_2{}^+$ and $(4\text{-n-Bu-}C_6H_4)NH(\text{n-}C_{10}H_{21})_2{}^+$, and $HNMe(C_{18}H_{37})_2{}^+$. Specific examples of anions include tetrakis(3,5-bis(trifluoromethyl)phenyl)borate and tetrakis (pentafluorophenyl)borate.

In one embodiment, activation methods using ionizing ionic compounds not containing an active proton but capable of producing an active oligomerization catalyst are also contemplated. Such methods are described in relation to metallocene catalyst compounds, e.g., as disclosed in European Publication Nos. EP 0 426 637 A1 and EP 0 573 403 A1, as well as in U.S. Pat. No. 5,387,568, the disclosures of all of which are incorporated herein by reference.

The process can also employ cocatalyst compounds or activator compounds that are initially neutral Lewis acids but form a cationic metal complex and a noncoordinating anion, or a zwitterionic complex, upon reaction with the compounds of this invention. For example, tris(pentafluorophenyl)boron or aluminum may act to abstract a hydrocarbyl or hydride ligand to yield a cationic metal complex and stabilizing noncoordinating anion.

In some embodiments, ionizing activators may be employed as described in Köhn et al. (*J. Organomet. Chem.*, 683, pp 200-208, (2003)) to, for example, improve solubility.

In another embodiment, the aforementioned cocatalyst compounds can also react with the compounds to produce a neutral, uncharged catalyst capable of selective ethylene oligomerization. For example, Lewis acidic reagents such as, for example, alkyl or aryl aluminum or boron compounds, can abstract a Lewis basic ligand such as, for example, THF or $Et_2O$, from a compound yielding a coordinatively unsaturated catalyst capable of selective ethylene oligomerization.

When the cations of noncoordinating anion precursors are Brönsted acids such as protons or protonated Lewis bases (excluding water), or reducible Lewis acids such as ferrocenium or silver cations, or alkali or alkaline earth metal cations such as those of sodium, magnesium, or lithium, the activator-to-catalyst-precursor molar ratio may be any ratio; however, useful ratios can include, but are not limited to, those from 1000:1 to 1:1.

Combinations of two or more activators may also be used in the practice of this invention.

Another suitable ion forming, activating cocatalyst comprises a salt of a cationic oxidizing agent and a noncoordinating, compatible anion characterized by the general formula:

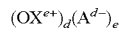

where $OX^{e+}$ is a cationic oxidizing agent having a charge of e+; e is an integer from 1 to 3; d is an integer from 1 to 3, and $A^{d-}$ is as previously defined. Examples of cationic oxidizing agents include, but are not limited to, ferrocenium, hydrocarbyl-substituted ferrocenium, $Ag^+$, $Pb^{+2}$, and combinations thereof. Preferred embodiments of $A^{d-}$ are those anions previously defined with respect to the Brönsted acid containing activators, especially tetrakis(pentafluorophenyl)borate.

Group 13 Reagents, Divalent Metal Reagents, and Alkali Metal Reagents

Other general activators or compounds useful in an oligomerization reaction may be used. These compounds may be activators in some contexts, but may also serve other functions in the reaction system, such as alkylating a metal center or scavenging impurities. These compounds are within the general definition of "activator," but are not considered herein to be ion-forming activators. These compounds can include a group 13 reagent that may be characterized by the formula $G^{13}R^{50}{}_{3-p}D_p$, where $G^{13}$ is selected from the group consisting of B, Al, Ga, In, and combinations thereof, where p is 0, 1, or 2, each $R^{50}$ is independently selected from the group consisting of hydrogen, halogen, optionally substituted alkyl, alkenyl, alkynyl, heteroalkyl, heteroalkenyl, heteroalkynyl, aryl, or heteroaryl, and combinations thereof, and where each D is independently selected from the group consisting of halogen, hydrogen, alkoxy, aryloxy, amino, mercapto, alkylthio, arylthio, phosphino, and combinations thereof.

In other embodiments, a divalent metal reagent may be used that is characterized by the general formula $M'R^{50}{}_{2-p'}D_{p'}$, where p' can be 0 or 1 and where $R^{50}$ and D are as defined above. M' is the metal and can be selected from the group consisting of Mg, Ca, Sr, Ba, Zn, Cd, Cu, and combinations thereof.

In still other embodiments, an alkali metal reagent may be used that is defined by the general formula $M^{iv}R^{50}$, where $R^{50}$ is as defined above, and where $M^{iv}$ is the alkali metal and can be selected from the group consisting of Li, Na, K, Rb, Cs, and combinations thereof. Additionally, hydrogen and/or silanes may be used in the catalytic composition and/or added to the polymerization system. Silanes may be characterized by the formula $SiR^{50}{}_{4-q}D_q$, where $R^{50}$ and D are defined as above, with the proviso that at least one D is hydrogen in this embodiment, and where q is 1, 2, 3, or 4.

Non-limiting examples of Group 13 reagents, divalent metal reagents, and alkali metal reagents useful as activators for the catalyst compounds described above can include: methyl lithium, butyl lithium, phenyl lithium, dihexylmercury, butylmagnesium, diethylcadmium, benzylpotassium, diethyl zinc, tri-n-butyl aluminum, diisobutyl ethylboron, diethylcadmium, di-n-butyl zinc, tri-n-amyl boron, in particular the aluminum alkyls such as trihexyl-aluminum, triethylaluminum, trimethylaluminum, and triisobutyl aluminum, diisobutyl aluminum bromide, diethylaluminum chloride, ethylaluminum dichloride, isobutyl boron dichloride, methyl magnesium chloride, ethyl beryllium chloride, ethyl calcium bromide, diisobutyl aluminum hydride, methyl cadmium hydride, diethyl boron hydride, hexylberyllium hydride, dipropylboron hydride, octylmagnesium hydride, butyl zinc hydride, dichloroboron hydride, di-bromo-aluminum hydride, and bromocadmium hydride. Additionally or alternately, other Group 13 reagents, divalent metal reagents, and alkali metal reagents useful as activators for the catalyst compounds described above are known to those in the art, and a more complete discussion of these compounds may be found, e.g., in U.S. Pat. Nos. 3,221,002 and 5,093,415, both of which are herein fully incorporated by reference.

Other activators include those described in International Publication No. WO 98/07515, incorporated herein by reference, such as tris(2,2',2''-nonafluorobiphenyl)fluoroaluminate, which publication is fully incorporated herein by reference. Combinations of activators also contemplated by the invention can include, for example, alumoxanes and ionizing activators in combinations; see, for example, European Publication No. EP 0 573 120 B1, International Publication Nos. WO 94/07928 and WO 95/14044, and U.S. Pat. Nos. 5,153, 157 and 5,453,410, the disclosures of all of which are herein fully incorporated by reference.

Other suitable activators are disclosed in International Publication No. WO 98/09996, incorporated herein by reference, which describes activating bulky ligand metallocene catalyst compounds with perchlorates, periodates, and iodates, including their hydrates. International Publication Nos. WO 98/30602 and WO 98/30603, incorporated herein by reference, describe the use of lithium (2,2'-bisphenyl-ditrimethylsilicate).4THF as an activator for a bulky ligand metallocene catalyst compound. International Publication No. WO 99/18135, incorporated herein by reference, describes the use of organoboron-aluminum activators. European Publication No. EP 0 781 299 B1 describes using a silylium salt in combination with a non-coordinating compatible anion. Also, methods of activation, such as using radiation (see European Publication No. EP 0 615 981 B1, incorporated herein by reference), electro-chemical oxidation, and the like, are also contemplated as activating methods for the purposes of rendering the chromium complexes or compositions active for the selective oligomerization of olefins. Other activators or methods are described, for example, in U.S. Pat. Nos. 5,849,852, 5,859,653, and 5,869,723, and in International Publication Nos. WO 98/32775 and WO 99/42467 (dioctadecylmethylammonium-bis(tris(pentafluorophenyl)borane)benzimidazolide), all of which are incorporated herein by reference.

Additional optional activators include metal salts of non-coordinating or weakly-coordinating anions, for example where the metal can be selected from Li, Na, K, Ag, Ti, Zn, Mg, Cs, and Ba.

It is within the scope of this invention that metal-ligand complexes and/or ligand-metal-precursor-combinations can be combined with one or more activators or activation methods described above. For example, a combination of activators has been described in U.S. Pat. Nos. 5,153,157 and 5,453,410, in European Publication No. EP 0 573 120 B1, and in International Publication Nos. WO 94/07928 and WO 95/14044. These documents all discuss the use of an alumoxane in combination with an ionizing activator.

Preferred activators used in the method of the present invention can be selected from the group consisting of modified methylalumoxane (MMAO), methylalumoxane (MAO), trimethylaluminum (TMA), triisobutyl aluminum (TIBA), polymethylalumoxane-IP (PMAO), N,N-di(n-decyl)-4-n-butyl-anilinium tetrakis(perfluorophenyl)borate, and mixtures thereof.

Typically, the molar ratio of metal (from the metal-ligand complex or the ligand-metal-precursor combination) to activator (specifically Cr:activator, or alternately Cr:Al or Cr:B) can range from 1:1 to 1:5000. In another embodiment, the molar ratio of metal to activator employed can range from 1:1 to 1:500. In another embodiment, the molar ratio of metal to activator employed can range from 1:1 to 1:50. In another embodiment, the molar ratio of chromium to activator employed can range from 1:1 to 1:500. In another embodiment, the molar ratio of chromium to activator employed can range from 1:1 to 1:50.

In embodiments where more than one activator is used, the order in which the activators are combined with the metal-ligand complex or the ligand-metal-precursor combination may be varied.

Very generally, the oligomerization can be carried out in the Ziegler-Natta or Kaminsky-Sinn methodology, including temperatures from −100° C. to 300° C. and pressures from atmospheric to 3000 atmospheres (303,900 kPa). Suspension, solution, slurry, gas phase, or high-pressure oligomerization processes may be employed with the processes of this invention. Such processes can be run in a batch, semi-batch, or continuous mode.

Suitable solvents and/or diluents for oligomerization are non-coordinating, inert liquids. Examples include, but are not limited to, mineral oil; straight and branched-chain hydrocarbons, such as propane, isobutane, butane, pentane, isopentane, hexane, isohexane, heptane, octane, dodecane, and mixtures thereof; cyclic and alicyclic hydrocarbons, such as cyclohexane, cycloheptane, methylcyclohexane, methylcycloheptane, and mixtures thereof; perhalogenated hydrocarbons such as perfluorinated $C_{4-10}$ alkanes; chlorobenzenes; and aromatic and alkylsubstituted aromatic compounds, such as benzene, toluene, mesitylene, and xylene. Suitable solvents and/or diluents may additionally or alternately include liquid olefins, which may act as monomers or comonomers, including, but not limited to, ethylene, propylene, 1-butene, 1-hexene, 1-pentene, 3-methyl-1-pentene, 4-methyl-1-pentene, 1-octene, 1-decene, and mixtures thereof. With regard to catalyst solvent and/or diluent, there is flexibility as far as what catalyst solvent and/or diluent may be used. Particularly preferred solvents and/or diluents can include, but are not limited to, the comonomer product (e.g., 1-butene, 1-hexene, 1-octene, combinations thereof, etc.), propane, $C_{4+}$ paraffins (e.g., isopentane, isobutane, butane, pentane, etc.), cycloparaffins, and aromatics (e.g., toluene). If the catalyst is in the form of an immobilized or fixed bed, it may not require additional solvent and/or diluent. In another exemplary embodiment, the catalyst to the comonomer synthesis reactor may be provided in the form of an immobilized or fixed bed, hence reducing and/or eliminating the need for a solvent and/or diluent altogether.

Other additives that are useful in an oligomerization reaction may be employed, such as scavengers, promoters, modifiers, reducing agents, oxidizing agents, dihydrogen, aluminum alkyls, and/or silanes. For example, Jolly et al. (*Organometallics*, 16, pp 1511-1513 (1997)) has reported the use of magnesium as a reducing agent for Cr compounds that were synthesized as models for intermediates in selective ethylene oligomerization reactions.

In some useful embodiments, the activator (such as methylalumoxane or modified methylalumoxane-3A) can be combined with the metal-ligand-complex or the ligand-metal-precursor-combination immediately prior to introduction into the reactor. Such mixing may be achieved by mixing in a separate tank, followed by swift injection into the reactor, by mixing in-line just prior to injection into the reactor, or the like. It has been observed that in some instances, a short activation time can be very useful. Likewise, in situ activation, where the catalyst system components are injected separately into the reactor, with or without monomer, and allowed to combine within the reactor directly, can also be useful in the practice of this invention. In some embodiments, the catalyst system components are allowed to contact each other for 30 minutes or less, prior to contact with monomer, alternately for 5 minutes or less, alternately for 3 minutes or less, alternately for 1 minute or less.

The comonomer synthesis reactor may take various forms, including but not limited to, a stirred tank, a (longer, thinner) tube-like contactor, or a bubble column. In an alternative embodiment, two or more comonomer synthesis reactors can be configured in series. An advantage of series reactors can be more thorough utilization of the catalyst, i.e., less nearly-fresh catalyst will get discharged with the product. Heat exchange capacity can also be incorporated in the reactor or in a pumparound loop, to limit the exotherm. For instance, heat exchange can be incorporated into the reactor by cooling and condensing vapors generated by the reaction and by returning the condensed liquid to the reactor, e.g., as reflux; this heat exchange in the reactor can advantageously make cooling surfaces in the reactor less susceptible to fouling, e.g., by polymer, catalyst residue, oligomers, etc. Where waxy buildup is an issue, spare heat exchangers may also be provided. Depending on the operating pressure of the reactor, the amount of the ethylene dissolved in the catalyst solvent and/or diluent may also be controlled, which can add flexibility in the design of the reactor and the process as a whole.

Comonomer synthesis reaction conditions of the instant invention can be selected and controlled to yield from about 20% to about 99%, for example from about 40% to about 95% or from about 60% to about 90%, single pass conversion of feed olefin (e.g., ethylene). In some embodiments, particularly where a relatively low single pass conversion of feed olefin (e.g., ethylene) is desired, the comonomer synthesis reaction conditions can be selected and controlled to yield a single pass conversion of feed olefin (e.g., ethylene) from about 10% to about 60%, for example from about 10% to about 50%, from about 10% to about 40%, from about 20% to about 50%, from about 20% to about 40%, from about 30% to about 50%, from about 25% to about 55%, from about 35% to about 55%, from about 35% to about 45%, from about 25% to about 45%, from about 20% to about 35%, from about 10% to about 30%, from about 15% to about 45%, or from about 15% to about 55%. In other embodiments, particularly where a relatively medium single pass conversion of feed olefin (e.g., ethylene) is desired, the comonomer synthesis reaction conditions can be selected and controlled to yield a single pass conversion of feed olefin (e.g., ethylene) from about 30% to about 80%, for example from about 40% to about 70%, from about 30% to about 60%, from about 30% to about 50%, from about 30% to about 70%, from about 40% to about 60%, from about 35% to about 75%, from about 35% to about 65%, from about 35% to about 55%, from about 45% to about 75%, from about 45% to about 65%, from about 50% to about 80%, from about 40% to about 75%, or from about 50% to about 75%.

For some of the chromium catalysts disclosed in U.S. Pat. No. 5,543,375, a range of reaction conditions are disclosed, which are herein incorporated by reference. One exemplary, but non-limiting, set of reactor conditions includes a temperature from about 60-150° C. or from about 80-150° C., and a pressure from about 300-900 psi (~21.1-63.3 kg/cm$^2$) or from about 300-700 psi (~21.1-49.2 kg/cm$^2$). A preferred range of reactor temperatures with ethylene can be from about 60-110° C. Reaction conditions may be tuned to obtain desired phase separations, as well as reactivity. In addition, reactor residence time is flexible, and may be chosen to provide a desired level of ethylene conversion. The residence time is typically a function of the type and amount of the catalyst utilized. In one exemplary embodiment, when utilizing the chromium type catalysts disclosed in U.S. Pat. No. 5,543,375, the average residence time can range from about 30 minutes to about 4 hours for a backmixed or pumparound reactor where most of the catalyst in the reactor at a given time is not "fresh," but has been circulating around for some time, and has become partially deactivated.

The effluent from the comonomer synthesis reactor can then be directed to a gas/liquid phase separator, where most of the ethylene goes overhead for recycle to the reactor or to a separate process. A catalyst deactivator may be added to the effluent from the reactor to minimize further reactions in downstream equipment. Exemplary catalyst deactivators include, but are not limited to, water and alcohol. Additionally or alternately, catalyst and activator (if present) may be removed from the reactor (or closely or immediately following the reactor) by adsorption, e.g., using a solid adsorbent system such as described in the purification system disclosure, infra. Exemplary gas/liquid phase separator types include, but are not limited to, a simple knockout vessel, flash drum, or other single or multi-stage phase separators. The gas/liquid phase separator may also include some trays or packing in the zone where vapor is going up, with reflux. The ethylene stream exiting from the gas/liquid phase separator may be pressurized via a compressor or blower prior to being fed back to the comonomer synthesis reactor or to another separate process.

In an alternative embodiment, two or more gas/liquid phase separators can be configured in series to further refine the separation of ethylene for alpha olefin comonomer. In another alternative embodiment, some ethylene can be added to the gas/liquid phase separator below the feed entrance point to strip out 1-hexene from the down-flowing solvent and/or diluent. In another alternative embodiment, the ethylene recycle can be dissolved in the recycled solvent and/or diluent at low temperatures. This configuration allows for a simple pump to pressurize the feed mixture instead of a more expensive compressor or blower.

In one preferred embodiment, the liquid bottoms from the gas/liquid phase separator can be sent to a purification system, advantageously to remove from the liquid bottoms at least a portion of contaminants that are substantially insoluble in the solvent and/or diluent, e.g., prior to any distillation step.

In some embodiments, the purification system can include at least one filtration system (e.g., in the form of a drum; hereinafter "filtration drum" without any intent to limit). In a preferred embodiment, the at least one filtration drum can include at least two filtration drums in a parallel arrangement, at least one first filtration drum in fluid communication with both the liquid bottoms stream and the subsequent distillation column, and at least one second filtration drum not in fluid communication with the liquid bottoms stream, and which is typically out of service for the purpose, e.g., of purging, removing, deactivating, decomposing, and/or otherwise disposing of contaminant(s) trapped therein.

Filtration drums according to the invention can typically have a primary purpose of filtering/trapping any polymeric and/or oligomeric material that is relatively insoluble in the solvent and/or diluent of the comonomer formation reaction process, and an optional secondary purpose of filtering/trapping relatively insoluble catalyst, catalyst activator(s), catalytic decomposition products, and/or other undesirable (typically organic) materials having considerably lower solubility in the solvent/diluent (e.g., isopentane) than the desired alpha olefin comonomer product (e.g., 1-hexene). One advantage of using a filtration drum includes a reduction and/or elimination of the need for post-distillation removal of solid/insoluble contaminants. Filtration drums are believed to have increased utility in reaction processes where relatively insoluble polymers/oligomers form, as it can be difficult to filter components from a highly soluble (e.g., homogeneous) composition.

In one embodiment, it may be advantageous to use as a filtration medium a material that can withstand the temperatures and (chemical) conditions associated with decomposition of polymers/oligomers, with deactivation of active catalyst, with exposure to active catalyst, or with combinations thereof. For example, the filtration medium can be comprised of a ceramic and/or a metal, optionally having a coating comprising a metal oxide, metal nitride, metal oxynitride, or the like, or combination thereof. In one embodiment, the filtration system can include commercially available systems, such as the CPF® (polymeric) filtration system and/or the ZHF® (centrifugal discharge) filtration system, both sold by the Pall Corporation.

Where filtration systems are present in the purification system according to the invention, one or more of the following steps may advantageously be accomplished in order to optimize the trapping/destroying/removing/deactivating efficiency of the purification system:

shutting down flow to a filtration drum, e.g., by taking a filtration drum containing some level of trapped contaminant(s) out of service (i.e., out of fluid communication with the liquid bottoms stream from the gas/liquid phase separator upstream, and optionally with the distillation column downstream), and, typically simultaneously, placing another filtration drum into service (i.e., into fluid communication with both the liquid bottoms stream from the gas/liquid phase separator upstream and the distillation column downstream);

depressurization of the filtration drum, e.g., through a top vent connection, which can advantageously serve to (further) cool any components trapped in the drum, e.g., for reducing the activity of any catalyst or any reactive chemical species present;

purging any volatile materials/contaminants from the filtration drum, e.g., with an inert gas and optionally with additional heat;

deactivating any residual catalyst activity, if present, e.g., by contacting with a deactivating agent such as liquid water, steam, oxygen, air, or a combination thereof, optionally also including contacting with an inert gas, e.g., in order to control any exotherm that may be caused by deactivation;

removing any remaining, typically solid, contaminants from the filtration medium for either recycling, further unrelated use, or disposal; and purging and/or drying (e.g., using heat and/or an inert gas) the filtration drum and medium to remove as much residual deactivation agent (e.g., oxygen and/or water) as possible, e.g., before returning flow to the filtration drum or putting it back into service, in order to reduce, inhibit, and/or prevent (re)circulation of deactivation agent into the system, e.g., which would typically reduce the activity and/or selectivity of the catalyst.

In other embodiments, the purification system can include at least one solid (e.g., catalyst) adsorbent system (e.g., in the form of a drum; hereinafter "catalyst adsorbent drum" without any intent to limit). In a preferred embodiment, the at least one catalyst adsorbent drum can include at least two catalyst adsorbent drums in a parallel arrangement, at least one first catalyst adsorbent drum in fluid communication with both the liquid bottoms stream and the subsequent distillation column, and at least one second catalyst adsorbent drum not in fluid communication with the liquid bottoms stream, and which is typically out of service for the purpose, e.g., of purging, removing, deactivating, decomposing, and/or otherwise disposing of contaminant(s) trapped therein.

Catalyst adsorbent drums according to the invention can typically have a primary purpose of adsorbing/trapping any inorganic and/or relatively insoluble solids (i.e., having considerably lower solubility in the solvent/diluent, e.g., isopentane, than the desired alpha olefin comonomer product, e.g., 1-hexene). One advantage of using a catalyst adsorbent drum includes a reduction and/or elimination of the need for post-distillation removal of solid/insoluble contaminants. Catalyst adsorbent drums are believed to have increased utility in reaction processes where catalyst and/or fines are likely to be entrained in the liquid bottoms from the gas/liquid phase separator.

The catalyst adsorbent drum typically contains a catalyst adsorbent agent, which can typically be a microporous solid, preferably having a specific surface area of at least 25 $m^2/g$, more preferably at least 50 $m^2/g$, for example at least 100 $m^2/g$. Specific surface area can be measured, e.g., according to a standard nitrogen BET process, such as ASTM D3663-03 and/or D4567-03 for catalytic materials. Catalyst adsorbent agents can be characterized in at least two different categories—adsorbent agents for metals/metallic catalyst components, which can include (but are not limited to) Lewis bases; and adsorbent agents for heteroatom-containing catalyst ligand components (i.e., typically organic components, but always containing one or more heteroatoms selected from the group consisting of nitrogen, oxygen, sulfur, phosphorus, and combinations thereof), which can include (but are not limited to) Lewis acids. Examples of suitable catalyst adsorbent agents according to the invention include, but are not limited to, clay, alumina, silica, molecular sieve, cellulose and/or cellulosic materials, and the like, and combinations thereof.

In a preferred embodiment, when the liquid bottoms stream from the gas/liquid phase separator is fed into the purification system containing the catalyst adsorbent drum, the microporous solid can advantageously adsorb/trap at least 50 wt %, preferably at least 75 wt %, more preferably at least about 90 wt %, most preferably at least about 95 wt %, e.g., as much as 99 wt % or about 100 wt %, of the metal-containing solids, catalyst, and/or catalyst activator(s) from the stream entering the catalyst adsorbent drum.

In one embodiment, flash cooling of a solvent/diluent can be used to lower the temperature of the incoming stream before contacting the microporous solid in the catalyst adsorbent drum. Preferably, the incoming stream can contact the microporous solid at a temperature below 120° C., more preferably below 100° C., e.g., below 80° C., below 60° C., below 50° C., from 35° C. to 45° C., or at about 45° C. The pressure requirements of the reaction system, including the pressure drop, reaction temperature, etc., can greatly depend on the solvent/diluent used.

In some embodiments, it can be both economical and advantageous to optimize the efficiency of the catalyst adsorbent drum by minimizing the amount of microporous solid therein, while optimally controlling the level of the metal-containing solids, heteroatom-containing solids, catalyst, and/or catalyst activator(s) that pass through the purification system and that flow into the distillation column.

Where catalyst adsorbent systems are present in the purification system according to the invention, one or more of the following steps may advantageously be accomplished in order to optimize the trapping/destroying/removing/deactivating efficiency of the purification system:

shutting down flow to a filtration drum, e.g., by taking a catalyst adsorbent drum containing some level of trapped contaminant(s) out of service (i.e., out of fluid communication with the liquid bottoms stream from the gas/liquid phase separator upstream, and optionally with the distillation column downstream), and, typically simultaneously, placing another catalyst adsorbent drum into service (i.e., into fluid communication with both the liquid bottoms stream from the gas/liquid phase separator upstream and the distillation column downstream);

depressurization of the catalyst adsorbent drum, e.g., through a top vent connection, which can advantageously serve to (further) cool any components trapped in the drum, e.g., for reducing the activity of any catalyst or any reactive chemical species present;

purging any volatile materials/contaminants from the catalyst adsorbent drum, e.g., with an inert gas and optionally with additional heat;

deactivating any reactive metals present, if any, and/or any residual catalyst activity, if present, e.g., by contacting with a deactivating agent such as liquid water, steam, oxygen, air, or a combination thereof, optionally also including contacting with an inert gas and/or a diluent, e.g., in order to control any exotherm that may be caused by deactivation;

oxidizing any trapped/remaining organic materials, if present, e.g., by contacting with an oxidizing agent such as an oxygen-containing gas, optionally also including contacting with an inert gas and/or a diluent, e.g., in order to control any exotherm that may be caused by oxidation, while typically seeking to avoid, if possible, apparatus damage and/or over-oxidation of metal-containing components to toxic substances (e.g., formation of $Cr^{VI}$ species);

removing any remaining contaminants from the catalyst adsorbent agent for either recycling, further unrelated use, or disposal; and purging and/or drying (e.g., using heat and/or an inert gas) the catalyst adsorbent drum and remaining catalyst adsorbent agent to remove as much residual deactivation agent (e.g., oxygen and/or water) as possible, e.g., before returning flow to the filtration drum or putting it back into service, in order to reduce, inhibit, and/or prevent (re)circulation of deactivation agent into the system, e.g., which would typically reduce the activity and/or selectivity of the catalyst.

In another embodiment, particularly where the liquid bottoms stream from the gas/liquid phase separator is in a relatively heterogeneous form (e.g., as a slurry) but also where it is in a relatively homogeneous form (e.g., as a solution), the purification system can advantageously include at least one filtration drum connected in series with at least one catalyst adsorbent drum. In another embodiment, the purification system can include at least two filtration drums connected in parallel with each other (at least one of which, e.g., would typically be out of service at any time), which at least two filtration drums are connected in series with at least two catalyst adsorbent drums connected in parallel with each other (at least one of which, e.g., would typically be out of service at any time).

The liquid bottoms from the purification system and/or from the gas/liquid phase separator, containing 1-hexene, other comonomers (e.g., octene and/or decene), and catalyst solvent and/or diluent, may then be conveyed to a distillation column. In a preferred embodiment, the catalyst is so selective that the amounts of $C_8$-$C_{10}$ byproducts produced are negligible. If these conditions are satisfied, the distillation column may function to separate the remaining ethylene from 1-hexene. The ethylene may then be recycled to the comonomer synthesis reactor, and the 1-hexene is discharged as product from the bottom of the column. While in some embodiments the catalyst can be so active that it can be diluted and disposed of in the hexene product post-distillation, in other embodiments the purification system mentioned above is needed and/or desired to remove as much of the catalyst as possible from the gas/liquid phase separator liquid bottoms prior to distillation. Although, optimally, either the purification system or a post-distillation catalyst and/or solids removal is appropriate, in some embodiments it may be advantageous to utilize both a pre-distillation purification system for removing solid contaminants (e.g., catalyst, which may or may not be spent/deactivated) and/or contaminants having a significant solubility difference, based on the solvent/diluent, from the olefin comonomer product (e.g., polymers, oligomers, other low molecular weight functionalized compounds, etc.) and a post-distillation purification system for separating the desired alpha olefin comonomer product(s) from contaminants that are do not have a significant solubility difference, based on the solvent/diluent, and/or from any other contaminants not trapped/removed by the pre-distillation purification system.

In an exemplary embodiment where a very active and very selective catalyst is utilized to produce 1-hexene, a light catalyst solvent and/or diluent may be used such that 1-hexene is collected as the bottom of the distillation column in very high purity, while the catalyst solvent and/or diluent and the ethylene from the overhead are recycled back to the comonomer synthesis reactor.

In another exemplary embodiment where separation between 1-hexene and heavier products is required in addition to the ethylene/hexene separation, a single distillation column may be utilized by making it a divided-wall type column. A divided wall column, for purposes of counting the number of distillation columns in the reaction system, counts as two distillation columns. In this configuration, the catalyst may be discharged with the heavy products. In another embodiment, the number of distillation columns present in the reaction system can advantageously be not more than the sum of one plus the number of alpha-olefin oligomers desired to be separated in said desired comonomer product.

In another exemplary embodiment, a small post-distillation column or other separation process can be utilized to separate the catalyst from the heavy products, such that the catalyst may be mixed in with the 1-hexene for disposal. In addition, deactivation of the catalyst at that point may be utilized, for example, with the use of water.

In another alternative embodiment of the instant invention, the comonomer synthesis reactor and gas/liquid separator can be combined into a single vessel for a classic catalytic distillation column, if compatible temperature and pressure can be found, and if sufficient residence time can be provided for reaction. This can further simplify the process complexity and can reduce costs associated with capital equipment and operating costs.

The olefin comonomer liquid product stream (1-butene, 1-hexene, 1-octene, and/or 1-decene) resulting from the method of the instant invention can be stored in tanks or other type of storage vessel prior to being transported for further processing. The olefin comonomers produced via the process of the instant invention may be used as the comonomer input of a polyolefin polymerization process, and/or a variety of other applications.

A list of embodiments according to the invention includes, but is not limited to, the following:

Embodiment 1

A method for preparing comonomer product from an olefin feed comprising:

contacting said olefin and a preformed catalyst having an olefin selectivity of at least 90 mol % to a desired comonomer product in a reactor under reaction conditions sufficient to produce an effluent comprising said desired comonomer product, wherein said desired comonomer product is an alpha-olefin oligomer.

Embodiment 2

A method for preparing a desired comonomer product from an olefin feed comprising:
contacting said olefin and a catalyst having an olefin selectivity of at least 90 mol % to said desired comonomer product in a reactor under reaction conditions sufficient to produce an effluent comprising said desired comonomer product,
wherein said desired comonomer product is an alpha-olefin oligomer, and
wherein the catalyst comprises the combination of:
1) a ligand represented by the formula:

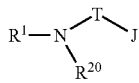

wherein:
N is nitrogen;
$R^1$ and $R^{20}$ are each independently selected from the group consisting of hydrogen, optionally substituted hydrocarbyl, heteroatom containing hydrocarbyl, and silyl, provided that $R^1$ or $R^{20}$ do not equal T-J, or alternately $R^1$ and $R^{20}$ are each independently a ring having from 4 to 8 atoms in the ring selected from the group consisting of substituted cycloalkyl, heterocycloalkyl, aryl, and heteroaryl;
T is a bridging group, preferably represented by the formula -(T'$R^2R^3$)—, where T' is carbon or silicon, $R^2$ and $R^3$ are each independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, provided that two or more $R^2$ and/or $R^3$ groups may be joined together to form one or more optionally substituted ring systems having from 3 to 50 non-hydrogen atoms; and
J is an optionally substituted six-membered heterocycle, containing at least one nitrogen atom as part of the ring, or J is an optionally substituted five-membered heterocycle, containing at least one nitrogen atom as part of the ring;
or a ligand represented by the formula:

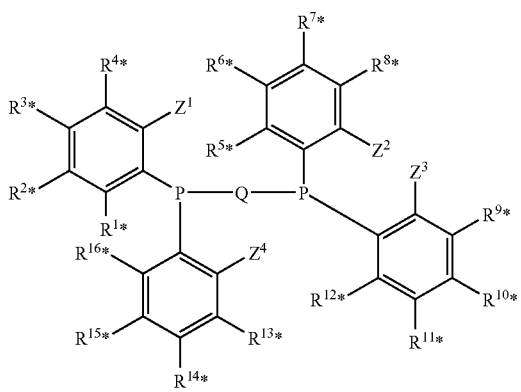

wherein:
P is phosphorus;
each of $R^{1*}$, $R^{2*}$, $R^{3*}$, $R^{4*}$, $R^{5*}$, $R^{6*}$, $R^{7*}$, $R^{8*}$, $R^{9*}$, $R^{10*}$, $R^{11*}$, $R^{12*}$, $R^{13*}$, $R^{14*}$, $R^{15*}$, and $R^{16*}$ is, independently, selected from the group consisting of hydrogen, halogen, optionally substituted hydrocarbyl, and optionally substituted heteroatom containing hydrocarbyl;
each of $Z^1$, $Z^2$, $Z^3$ or $Z^4$ is, independently, selected from the group consisting of hydrogen, a hydrocarbyl, alkoxy, aryloxy, alkylthio, arylthio, hydroxyl, mercapto, and amino; and
Q is a bridging group selected from the group consisting of optionally substituted hydrocarbyl having from 2 to 20 carbon atoms;
2) a metal precursor compound characterized by the general formula $Cr(L)_n$ where each L is independently selected from the group consisting of halide, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers, and combinations thereof, wherein two or more L groups may be combined in a ring structure having from 3 to 50 non-hydrogen atoms; and n is 1, 2, 3, 4, 5, or 6; and
3) optionally, one or more activators.

Embodiment 3

A method for preparing a desired comonomer product from an olefin feed comprising:
providing a reactor and a number of distillation columns;
feeding to said reactor said olefin feed and a catalyst having an olefin selectivity of at least 90 mol % to said desired comonomer product;
reacting in said reactor said olefin feed and said catalyst under reaction conditions sufficient to produce an effluent comprising said desired comonomer product, reaction byproducts, and unreacted olefin; and
separating said desired comonomer product from said effluent in said less than three gas/liquid phase separators to attain an olefinic purity of desired comonomer product of at least 98.5 mol %,
wherein said desired comonomer product is an alpha-olefin oligomer, and
wherein the number of distillation columns is not more than the sum of one plus a number of alpha-olefin oligomers desired to be separated in said desired comonomer product.

Embodiment 4

The method of embodiment 1 or embodiment 3, wherein the preformed catalyst comprises the combination of:
1) a ligand represented by the formula:

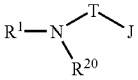

wherein:
N is nitrogen;
$R^1$ and $R^{20}$ are each independently selected from the group consisting of hydrogen, optionally substituted hydrocarbyl, heteroatom containing hydrocarbyl, and silyl, provided that $R^1$ or $R^{20}$ do not equal T-J, or alternately $R^1$ and $R^{20}$ are each independently a ring having from 4 to 8 atoms in the ring selected from the group consisting of substituted cycloalkyl, heterocycloalkyl, aryl, and heteroaryl;

T is a bridging group, preferably represented by the formula -(T'R$^2$R$^3$)—, where T' is carbon or silicon, R$^2$ and R$^3$ are each independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, provided that two or more R$^2$ and/or R$^3$ groups may be joined together to form one or more optionally substituted ring systems having from 3 to 50 non-hydrogen atoms; and J is an optionally substituted six-membered heterocycle, containing at least one nitrogen atom as part of the ring, or J is an optionally substituted five-membered heterocycle, containing at least one nitrogen atom as part of the ring;

or a ligand represented by the formula:

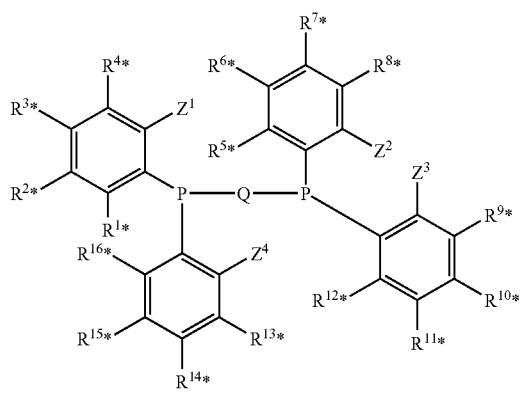

wherein:

P is phosphorus;

each of R$^{1*}$, R$^{2*}$, R$^{3*}$, R$^{4*}$, R$^{5*}$, R$^{6*}$, R$^{7*}$, R$^{8*}$, R$^{9*}$, R$^{10*}$, R$^{11*}$, R$^{12*}$, R$^{13*}$, R$^{14*}$, R$^{15*}$, and R$^{16*}$ is, independently, selected from the group consisting of hydrogen, halogen, optionally substituted hydrocarbyl, and optionally substituted heteroatom containing hydrocarbyl;

each of Z$^1$, Z$^2$, Z$^3$ or Z$^4$ is, independently, selected from the group consisting of hydrogen, a hydrocarbyl, alkoxy, aryloxy, alkylthio, arylthio, hydroxyl, mercapto, and amino; and Q is a bridging group selected from the group consisting of optionally substituted hydrocarbyl having from 2 to 20 carbon atoms;

2) a metal precursor compound characterized by the general formula Cr(L)$_n$ where each L is independently selected from the group consisting of halide, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers, and combinations thereof, wherein two or more L groups may be combined in a ring structure having from 3 to 50 non-hydrogen atoms; and n is 1, 2, 3, 4, 5, or 6; and 3) optionally, one or more activators.

Embodiment 5

A method for polymerizing a polyethylene copolymer comprising contacting ethylene and one or more of the comonomers made according to the method of any of the previous embodiments in a polymerization reactor under conditions sufficient to form a polyethylene copolymer.

Embodiment 6

The method of any of the previous embodiments, wherein said olefin feed is greater than about 99 wt % ethylene.

Embodiment 7

The method of any of embodiments 2 and 4-6, wherein the ligand of the catalyst is represented by at least one of the following formulas:

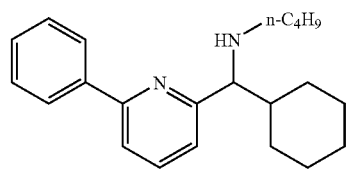

A29

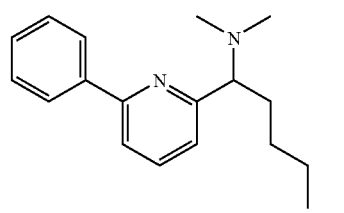

A53

Embodiment 8

The method of any of embodiments, wherein said catalyst comprises one or more activators.

Embodiment 9

The method of any of the previous embodiments, wherein the contacting is accomplished in the presence of a solvent and/or diluent.

Embodiment 10

The method of embodiment 9, wherein the solvent and/or diluent is selected from the group consisting of 1-butene, 1-hexene, 1-octene, toluene, propane, butane, isobutane, pentane, isopentane, and combinations thereof.

Embodiment 11

The method of embodiment 9, wherein said solvent and/or diluent is 1-hexene, isopentane, or the combination thereof.

Embodiment 12

The method of any of the previous embodiments, wherein said reaction conditions yield from about 20% to about 95% single pass conversion of said olefin.

Embodiment 13

The method of embodiment 12, wherein said reaction conditions comprise a reaction temperature from about 60° C. to about 150° C., a reaction pressure from about 300 psi (21.1 kg/cm$^2$) to about 900 psi (63.3 kg/cm$^2$), and a reaction residence time from about 30 minutes to about 4 hours.

Embodiment 14

The method of any of the previous embodiments, wherein the reactor comprises one or more bubble column reactors.

Embodiment 15

The method of embodiment 14, wherein at least one of the one or more bubble column reactors has more than one reaction stage.

Embodiment 16

The method of embodiment 14, wherein at least one of the one or more bubble column reactors comprises no mechanical agitation.

Embodiment 17

The method of embodiment 15, wherein at least one of the one or more bubble column reactors comprises no mechanical agitation.

Embodiment 18

The method of any of the previous embodiments, wherein a catalyst deactivator is added to said effluent stream exiting from said comonomer synthesis reactor.

Embodiment 19

The method of embodiment 18, wherein said catalyst deactivator comprises water, alcohol, or a combination thereof.

Embodiment 20

The method of any of the previous embodiments, further comprising providing at least one gas/liquid phase separator downstream from said reactor.

Embodiment 21

The method of embodiment 20, wherein said downstream gas/liquid phase separator further comprise trays or packing in the vapor zone.

Embodiment 22

The method of embodiment 20, further comprising the step of adding olefin that is the same as said olefin feed to said downstream gas/liquid phase separator to strip out said desired comonomer product from said effluent.

Embodiment 23

The method of any of the previous embodiments, further comprising purifying said effluent, which comprises filtering at least a portion of said effluent.

Embodiment 24

The method of any of the previous embodiments, further comprising purifying said effluent, which comprises adsorbing catalyst from at least a portion of said effluent.

Embodiment 25

The method of embodiment 24, where said purifying step further comprises filtering at least a portion of said effluent.

Embodiment 26

The method of any of the previous embodiments, wherein said effluent comprises a gas stream and a liquid stream.

Embodiment 27

The method of embodiment 26, wherein said gas stream comprises said desired comonomer product.

Embodiment 28

The method of embodiment 26, wherein said liquid stream comprises said desired comonomer product.

Embodiment 29

The method of any of the previous embodiments, wherein the reactor comprises a combination of a comonomer synthesis reactor and a gas/liquid phase separator.

Embodiment 30

The method of any of embodiments 1-2 and 4-29, further comprising providing a distillation column.

Embodiment 31

The method of embodiment 30, wherein one or more of the following: (i) said reactor comprises two or more reactors in series; (ii) said gas/liquid phase separator comprises two or more gas/liquid phase separators in series; and (iii) said distillation column comprises two or more distillation columns in series.

Embodiment 32

The method of any of the previous embodiments, wherein less than three distillation columns are provided.

Embodiment 33

The method of any of embodiments 3 or 30-32, wherein said distillation column(s) separate(s) unreacted olefin from the top and said desired comonomer product from the bottom.

Embodiment 34

The method of embodiment 33, wherein said distillation column further separates said solvent and/or diluent from the top.

Embodiment 35

The method of any of embodiments 30-31 or 33-34, wherein said distillation column comprises a divided wall type column.

Embodiment 36

The method of any of embodiments 3, 30-32, or 35, wherein said distillation column separates said desired comonomer product from the bottom and said solvent and/or diluent from the top.

Embodiment 37

The method of embodiment 36, wherein the distillation column further separates unreacted olefin from the top.

Embodiment 38

The method of any of embodiments 9-37, further comprising recycling to said reactor unreacted olefin and at least a portion of said solvent and/or diluent.

Embodiment 39

The method of embodiment 20, wherein the reactor comprises two or more reactors in series, wherein the gas/liquid phase separator comprises two or more gas/liquid phase separators in series, or both.

Embodiment 40

The method of any of the previous embodiments, wherein said desired comonomer product is selected from the group consisting of 1-butene, 1-hexene, 1-octene, and 1-decene.

Embodiment 41

The method of embodiment 40, wherein said catalyst has an olefin selectivity of at least 95 mol % to said desired comonomer product.

Embodiment 42

The method of embodiment 40, wherein said catalyst has an olefin selectivity of at least 97 mol % to said desired comonomer product.

Embodiment 43

The method of embodiment 40, wherein said catalyst has an olefin selectivity of at least 98.5 mol % to said desired comonomer product.

Embodiment 44

The method of any of the previous embodiments, wherein said catalyst has an olefin selectivity of at least 95 mol % to said desired comonomer product, and wherein said desired comonomer product is two olefins selected from the group consisting of 1-butene, 1-hexene, 1-octene, and 1-decene.

Embodiment 45

The method of embodiment 44, wherein said catalyst has an olefin selectivity of at least 98.5 mol % to said desired comonomer product.

Embodiment 46

The method of any of the previous embodiments, wherein said catalyst has an olefin selectivity of at least 98.5 mol % to said desired comonomer product, and wherein said desired comonomer product is three olefins selected from the group consisting of 1-butene, 1-hexene, 1-octene, and 1-decene.

Embodiment 47

The method of embodiment 46, wherein said catalyst has an olefin selectivity of at least 99 mol % to said desired comonomer product.

Embodiment 48

The method of any of the previous embodiments, wherein said catalyst has an olefin selectivity of at least 97.5 mol % to said desired comonomer product, and wherein the desired comonomer product is 1-hexene.

Embodiment 49

The method of any of the previous embodiments, wherein said catalyst has an olefin selectivity of at least 98.5 mol % to said desired comonomer product, and wherein the desired comonomer product is 1-hexene.

Embodiment 50

The method of any of the previous embodiments, further comprising storing the desired comonomer product prior to a subsequent use thereof.

Embodiment 51

The method of any of embodiments 1, 3, and 5-50, wherein the ligand of the catalyst is represented by the formula:

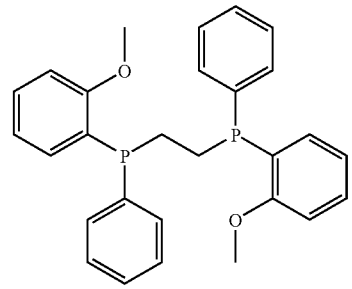

A2

Embodiment 52

The method of any of embodiments 1-39 and 50-52, wherein the desired comonomer product is selected from the group consisting of 1-butene, 1-hexene, 1-octene, 1-decene, and mixtures thereof.

Embodiment 53

The method of any of the previous embodiments, wherein the reactor utilizes evaporative cooling.

Applicants have attempted to disclose all embodiments and applications of the disclosed subject matter that could be reasonably foreseen. However, there may be unforeseeable, insubstantial modifications that remain as equivalents. While the present invention has been described in conjunction with specific, exemplary embodiments thereof, it is evident that many alterations, modifications, and variations will be apparent to those skilled in the art in light of the foregoing description without departing from the spirit or scope of the present disclosure. Accordingly, the present disclosure is intended to embrace all such alterations, modifications, and variations of the above detailed description.

The following simulated examples illustrate the present invention and the advantages thereto without limiting the scope thereof. The examples are based upon computer based simulations of the input streams and process conditions utilized for each of the exemplary process flow schematics illustrated.

EXAMPLES

For the purposes of the figures which follow in the simulated examples, "S" designates flow stream, "R" designates reactor, "F" designates gas/liquid phase separator, "C" designates compressor or blower, "M" designates mixing element, "P" designates pump, "SP" designates flow splitter, "E" designates heat exchanger, and "T" designates distillation column or tower. The number which follows each of the designations signifies the number of such element within the respective process schematic.

In examples 1-4, a 100% pure ethylene feed is utilized assuming 100% selectivity to produce an alpha-olefin product (either 1-butene or 1-hexene). These idealized conditions were selected for the purpose of determining equipment needs. In practice, the ethylene feed would be less than 100% pure (preferably 98.0-99.9% pure), and reaction selectivity would be less than 100% (e.g., 90-98%). In example 5, a polymer grade ethylene feed (99.9% ethylene and 0.1% ethane) is utilized with an olefin selectivity (olefinic product distribution) of about 98% 1-hexene, about 0.4% 1-octene, and about 1.6% $C_{10}$ (1-decene and internal decenes).

Simulation Example 1

1-Hexene Product as a Catalyst Solvent

An exemplary process schematic using the 1-hexene product as the solvent is shown in FIG. 1. The ethylene feed is 100% ethylene while the reaction selectivity to 1-hexene is 100%. The feed is mixed with a recycled ethylene and 1-hexene stream S1 and is fed to reactor $R^2$. The reactor $R^2$ is operated at 90° C. and 400 psia (~2.76 MPaa) and is sized to achieve 60% per pass conversion of ethylene. The product stream from the reactor S2 is separated from the unconverted ethylene using two flash drums F1, F2 operated at 400 and 14.96 psia (~2.76 and ~0.1 MPaa), respectively. The gas outlet S6 of the second flash drum F2 is then recompressed at 400 psia using a compressor C1 and recycled back to the reactor $R^2$. The liquid stream S4 from the second flash drum F2, which includes >99.5% 1-hexene, is split into two streams, S10 and C6PRODUCT, using a flow splitter SP1. The S10 hexene stream is recycled acting as the catalyst solvent in comonomer synthesis process. Homogeneous or slurry catalyst leaves with the C6PRODUCT stream. A summary listing of stream flow rates and compositions is shown in Table 1. If conversion is increased to 90%, the ethylene concentration in the reactor product stream S2 is sufficiently low such that S2 becomes a single phase (liquid). In this case the first flash drum F1 can be eliminated, which further simplifies the process.

TABLE 1

Flow Rates and Compositions

| | Rate (kg/hr) | Ethylene | 1-Hexene |
|---|---|---|---|
| Ethylene Feed | 15300 | 100% | |
| Reactor Outlet | 40500 | 23.30% | 76.70% |
| 1-Hexene Product | 15300 | 0.80% | 99.20% |
| Recycle | 25300 | 18% | 82% |

Simulation Example 2

1-Hexene Product with Toluene as a Catalyst Solvent

Figure 2:
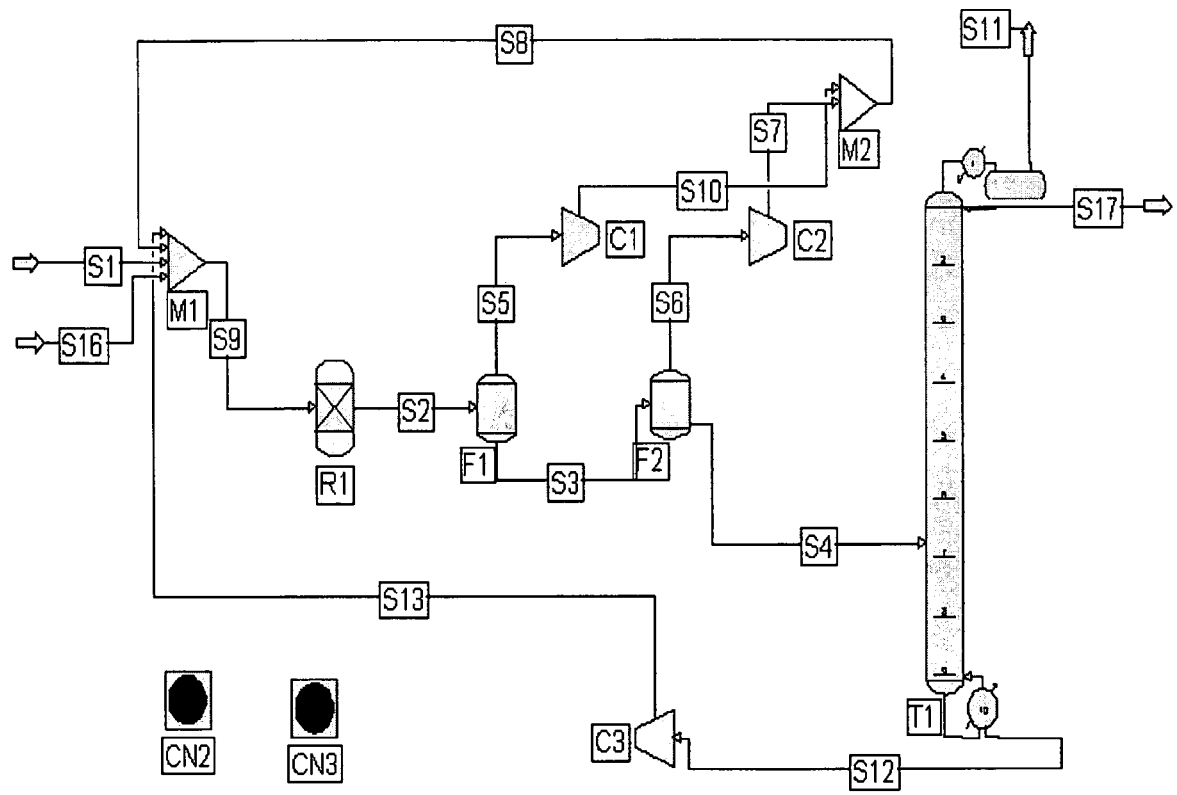
FIG. 2 depicts an exemplary process schematic of the process of the present invention for generating 1-hexene with toluene as a solvent and/or diluent.

Another exemplary process using toluene as the catalyst solvent is shown in FIG. 2. The ethylene feed S1 is again 100% ethylene while the reaction selectivity to 1-hexene is 100%. The ethylene feed S1 is mixed through M1 with recycle stream S8 containing ethylene, solvent, and 1-hexene and is fed to reactor R1. The reactor R1 is operated at 100° C. and 400 psia (~2.76 MPaa) and is sized to achieve 50% per pass conversion of ethylene. The product and the solvent are separated from the unconverted ethylene using two flash drums F1, F2 in series operated at 300 and 14.96 psia (~2.07 and ~0.1 MPaa), respectively. The gas outlets of the flash drums S5, S6 are recompressed to 400 psia (~2.76 MPaa), combined in one stream S8 and recycled back to the reactor R1. The liquid stream S4 from flash unit F2 is fed to a distillation column operation T1 at atmospheric pressure in order to separate 1-hexene S17 from the toluene solvent S12. The toluene solvent S12 collected at the bottom of the column is recycled via S13. Since the homogeneous or slurry catalyst leaves with the solvent, a portion of that recycled stream can be purged and fresh catalyst added to the system via S16 such that the activity of the catalyst in the reactor can be maintained constant. A summary listing of stream flow rates and compositions is shown in Table 2. An increase in the ethylene conversion would allow further simplification of the process similar to that of example 1.

TABLE 2

Flow Rates and Compositions

| | Rate (kg/hr) | Ethylene | Toluene | 1-Hexene |
|---|---|---|---|---|
| Ethylene Feed | 15300 | 100% | | |
| Solvent Feed | 45 | | 100.00% | |
| Recycle | 29800 | 76% | 4% | 20% |
| Solvent Recycle | 18000 | | 95% | 5% |
| Product | 14100 | 0.12% | 0.38% | 99.50% |

Simulation Example 3

1-Hexene Product with Isopentane as a Solvent—High Pressure

Figure 3:
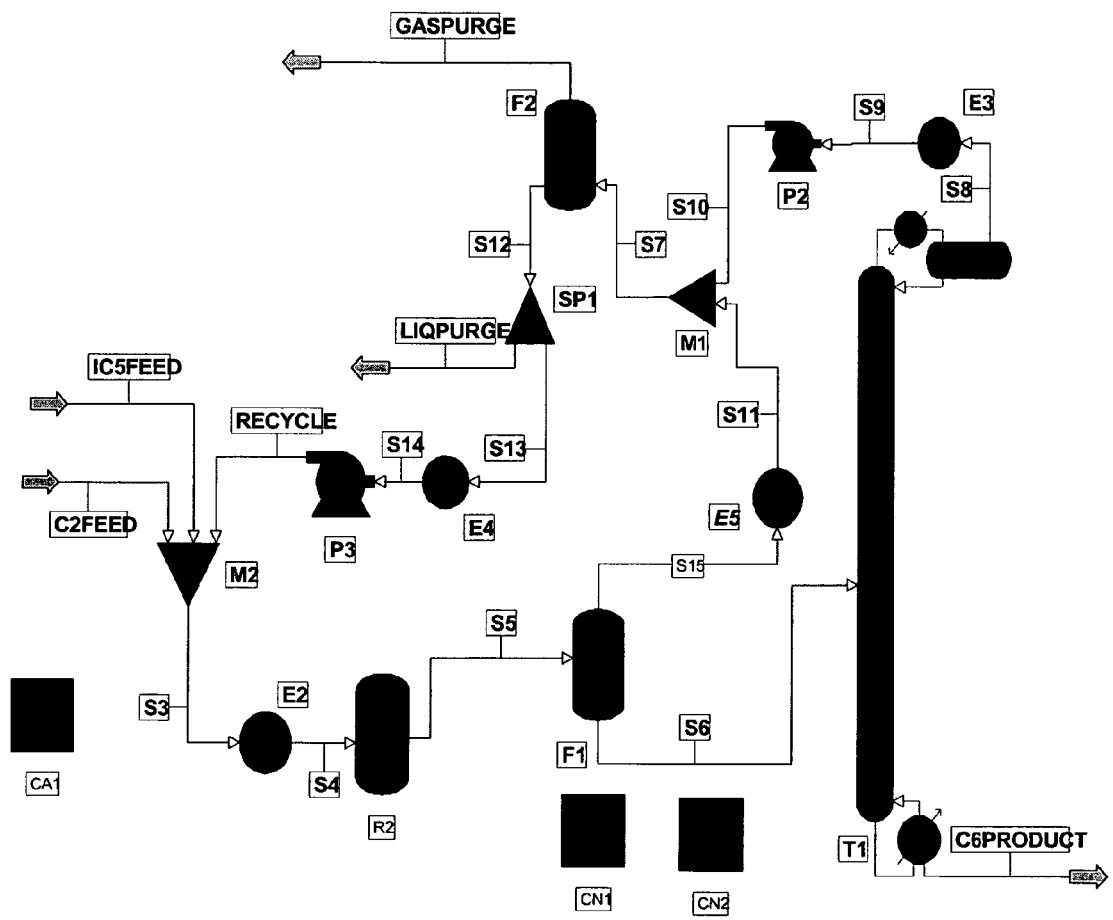
FIG. 3 depicts an exemplary process schematic of the process of the present invention for generating 1-hexene with isopentane as a solvent and/or diluent at high pressure.

Another exemplary process using isopentane as the catalyst solvent at high pressure is shown in FIG. 3. Increasing the process pressure allows for an operation with the recycle stream as a liquid, which permits the use of a pump instead of an expensive compressor to transport the recycle stream. In this exemplary process, ethylene feed (C2FEED) is oligomerized to 1-hexene at 90° C. and 800 psia (~5.52 MPaa) using isopentane, IC5FEED, as a catalyst solvent. The C2FEED is 100% ethylene while the reaction selectivity to 1-hexene is 100%. The feed is mixed with recycled ethylene, isopentane and 1-hexene (Recycle) and fed to the reactor $R^2$. The reactor $R^2$ is operated at 90° C. and 800 psia (~5.52 MPaa) and is sized to achieve 80% per pass conversion of ethylene. The reactor product stream S5 is then fed to a flash drum F1 where the 1-hexene stream S6 is separated from the unconverted ethylene and catalyst solvent stream S15 at 150 psia (~1.03 MPaa). The bottoms stream S6 from the flash drum F1 is then fed to a distillation column T1 operated at 60 psia to complete the separation of 1-hexene, C6PRODUCT, from unconverted ethylene and catalyst solvent S8. The C6PRODUCT, including the homogeneous/slurry catalyst, is collected at the bottom of the distillation column. The overhead vapors of unconverted ethylene and catalyst solvent S8 from the distillation column T1 are condensed to form a liquid stream S9 using a heat exchanger E3 and transported using a pump P2 operated at 150 psia (~1.03 MPaa). The condensed unconverted ethylene and catalyst solvent stream S10 and a condensed overhead vapor stream S11 from the from the flash drum F1 are mixed through a mixing element M1. The combined stream S7 is separated into a gas and liquid phase in second flash drum F2. The liquid stream S13 is then subcooled through a heat exchanger E4, pumped back to 800 psia (~5.52 MPaa) using a pump P3 and recycled back to the reactor $R^2$ as a recycle stream (RECYCLE). A summary listing of stream flow rates and compositions is shown in Table 3.

TABLE 3

Flow Rates and Compositions

|  | Rate (kg/hr) | Ethylene | Isopentane | 1-Hexene |
|---|---|---|---|---|
| Ethylene Feed | 15300 | 100% |  |  |
| Solvent Feed | 64.4 |  | 100.00% |  |
| Recycle | 22900 | 34% | 63% | 3% |
| Product | 15300 | 0.00% | 0.50% | 99.50% |

Simulated Example 4

1-Butene Product with Isopentane as a Solvent—High Pressure

Figure 4:
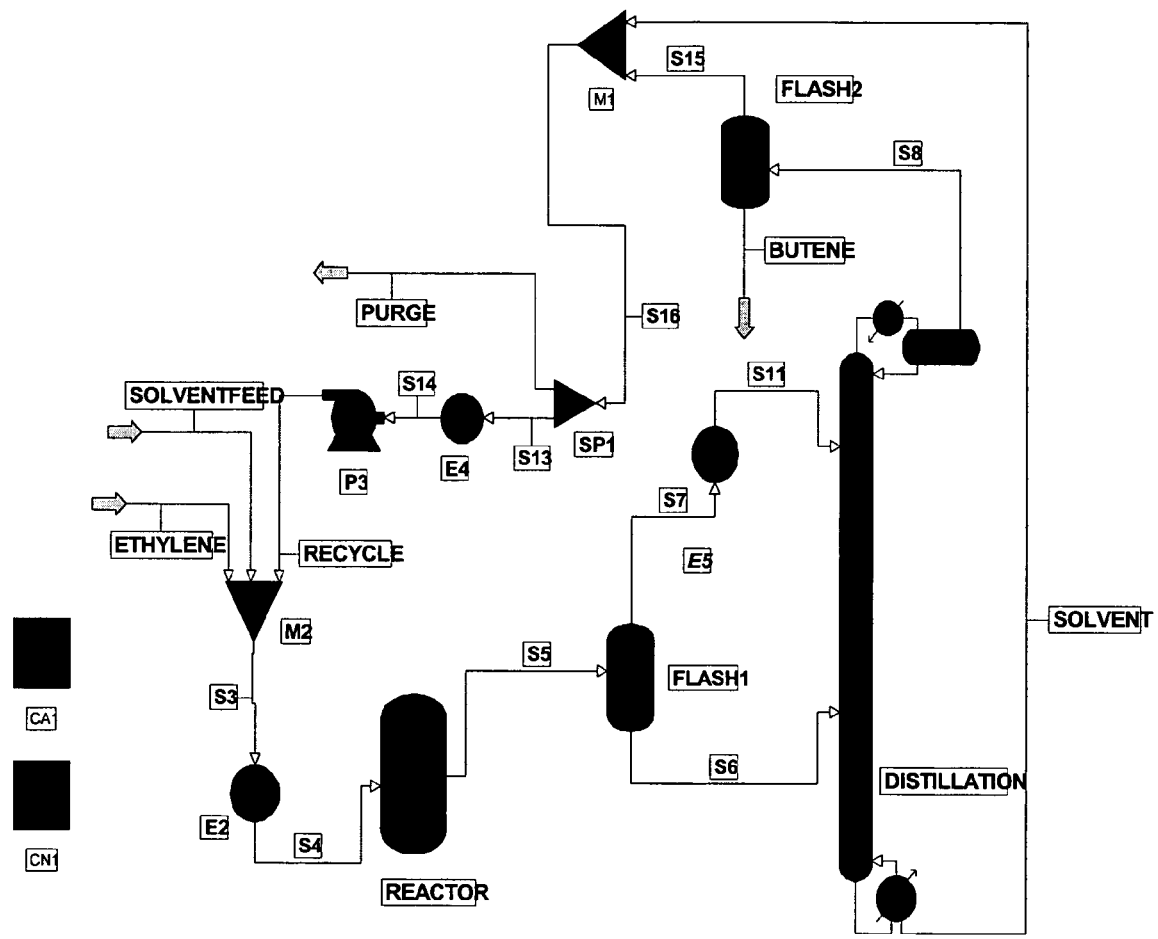
FIG. 4 depicts an exemplary process schematic of the process of the present invention for generating 1-butene with isopentane as a solvent and/or diluent at high pressure.

Another exemplary process to produce 1-butene using isopentane as the catalyst solvent at high pressure is shown in FIG. 4. In this example, the conditions and the process flow schematic are similar to Example 3. However, instead of a 1-hexene selective catalyst, a 1-butene selective catalyst is used. 1-butene is lighter than isopentane and is collected as the overhead vapor S8 from the distillation column operating at 60 psia (~0.4 MPaa). The vapors, which are a mixture of 1-butene and ethylene are then cooled to −20° C., and the liquid product is separated in a second flash drum, FLASH2, operating at 50 psia (~0.3 MPaa). The product stream, BUTENE, from the second flash drum, FLASH2, is 85.5% 1-butene. This product stream, BUTENE, can be directly fed to a polyethylene reactor (not shown). However if a higher purity is needed a second distillation column instead of the second flash drum, FLASH2, may be used. The overhead vapors from the second flash drum, FLASH2, are mixed through a mixing device M1 with the recycled isopentane stream from the distillation column, SOLVENT, condensed through a heat exchanger, E4, and pumped with a pump P3 to 800 psia (~5.52 MPaa), and then recycled as a recycle stream (RECYCLE) to the reactor. A summary listing of stream flow rates and compositions is shown in Table 4.

TABLE 4

Flow Rates and Compositions

|  | Rate (kg/hr) | Ethylene | Isopentane | 1-Butene |
|---|---|---|---|---|
| Ethylene Feed | 15300 | 100% |  |  |
| Solvent Feed | 140 |  | 100.00% |  |
| Recycle | 21400 | 24.20% | 70.90% | 4.90% |
| Product | 15400 | 14.50% | 0.00% | 85.50% |

Simulated Example 5

1-Hexene Product with Isopentane Solvent w/Polymer Grade Feed

Figure 5:
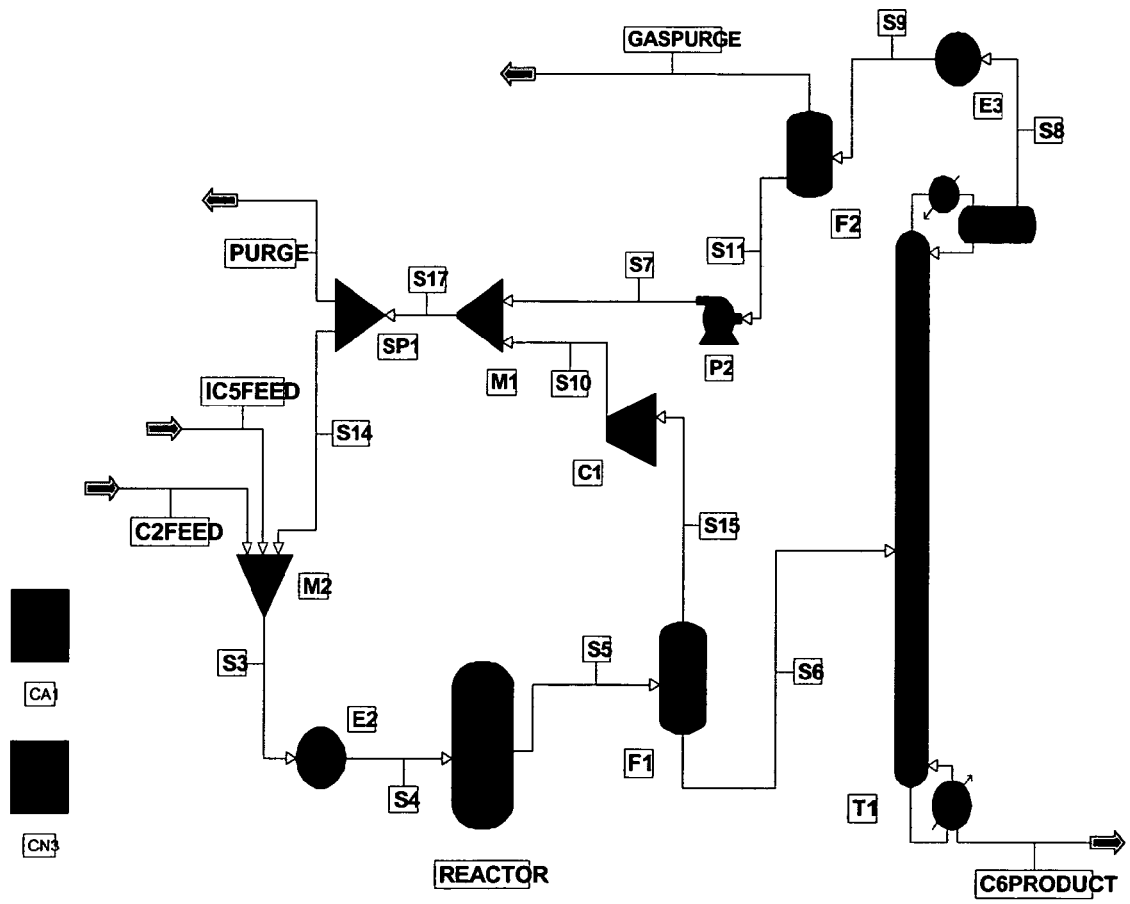
FIG. 5 depicts an exemplary process schematic of the process of the present invention for generating 1-hexene with isopentane as a solvent and/or diluent and using polymer grade feed.
Figure 6:
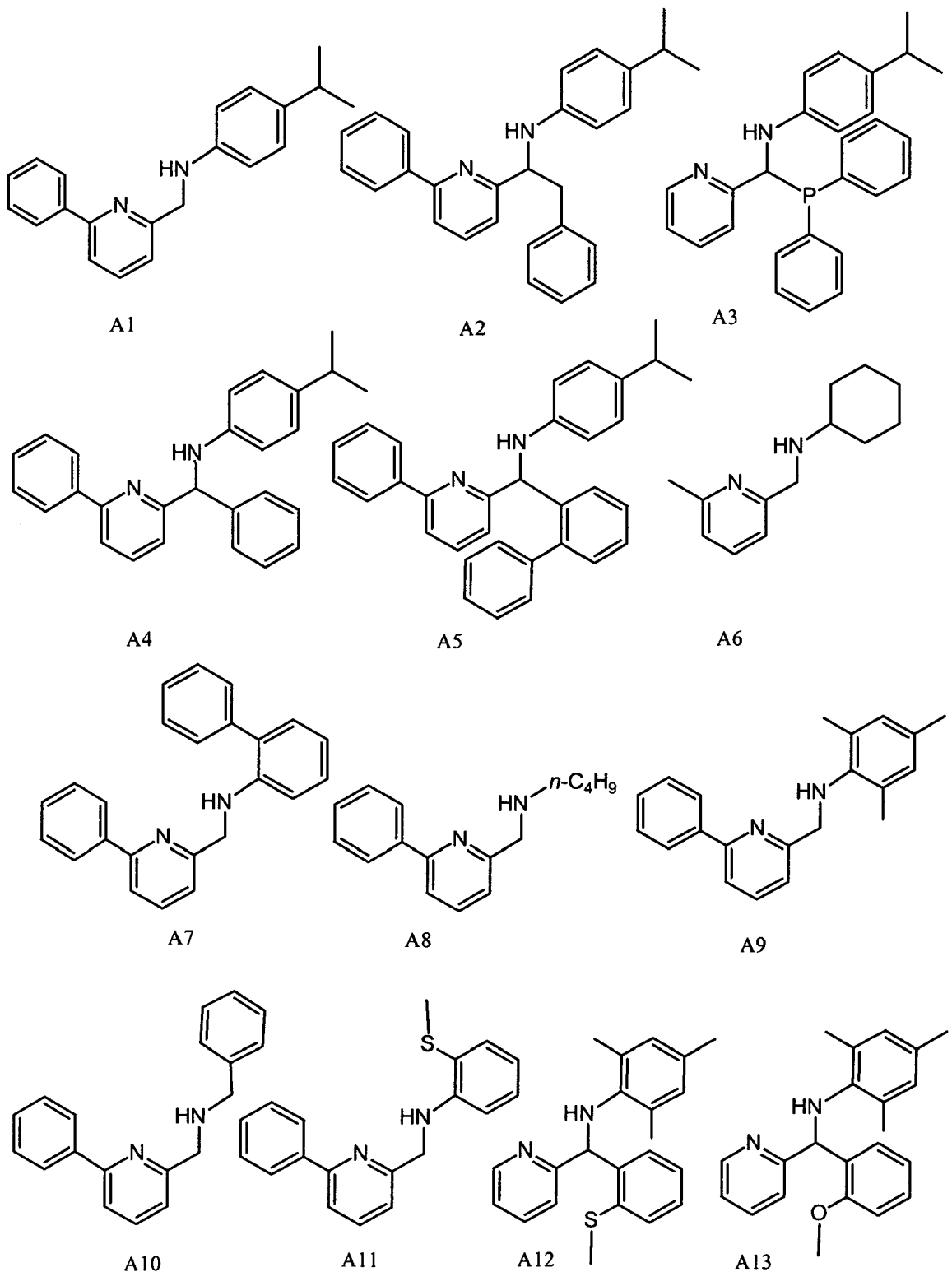
FIG. 6 illustrates pyridyl-amine ligands A1-A13.
Figure 7:
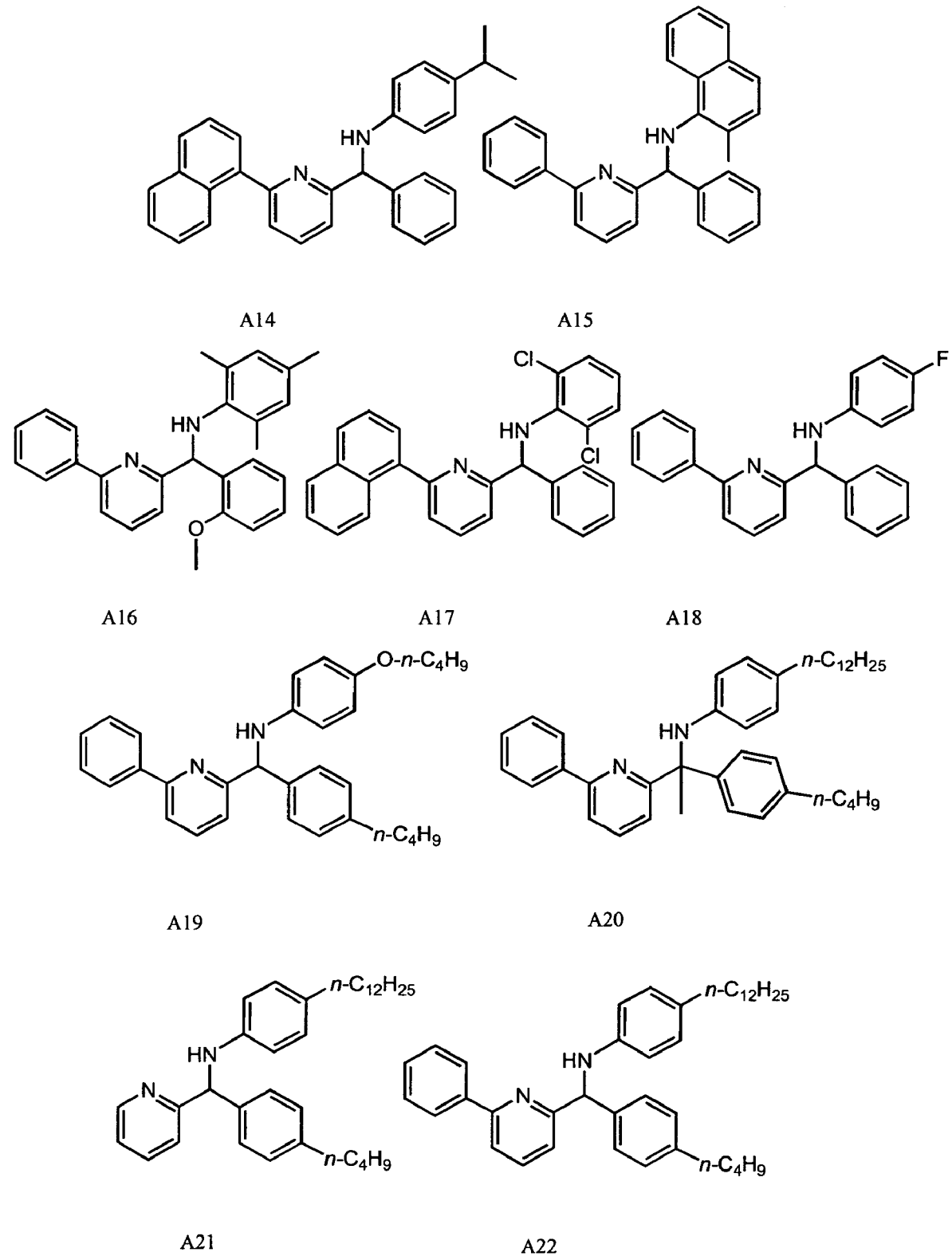
FIG. 7 illustrates pyridyl-amine ligands A14-A22.
Figure 9:
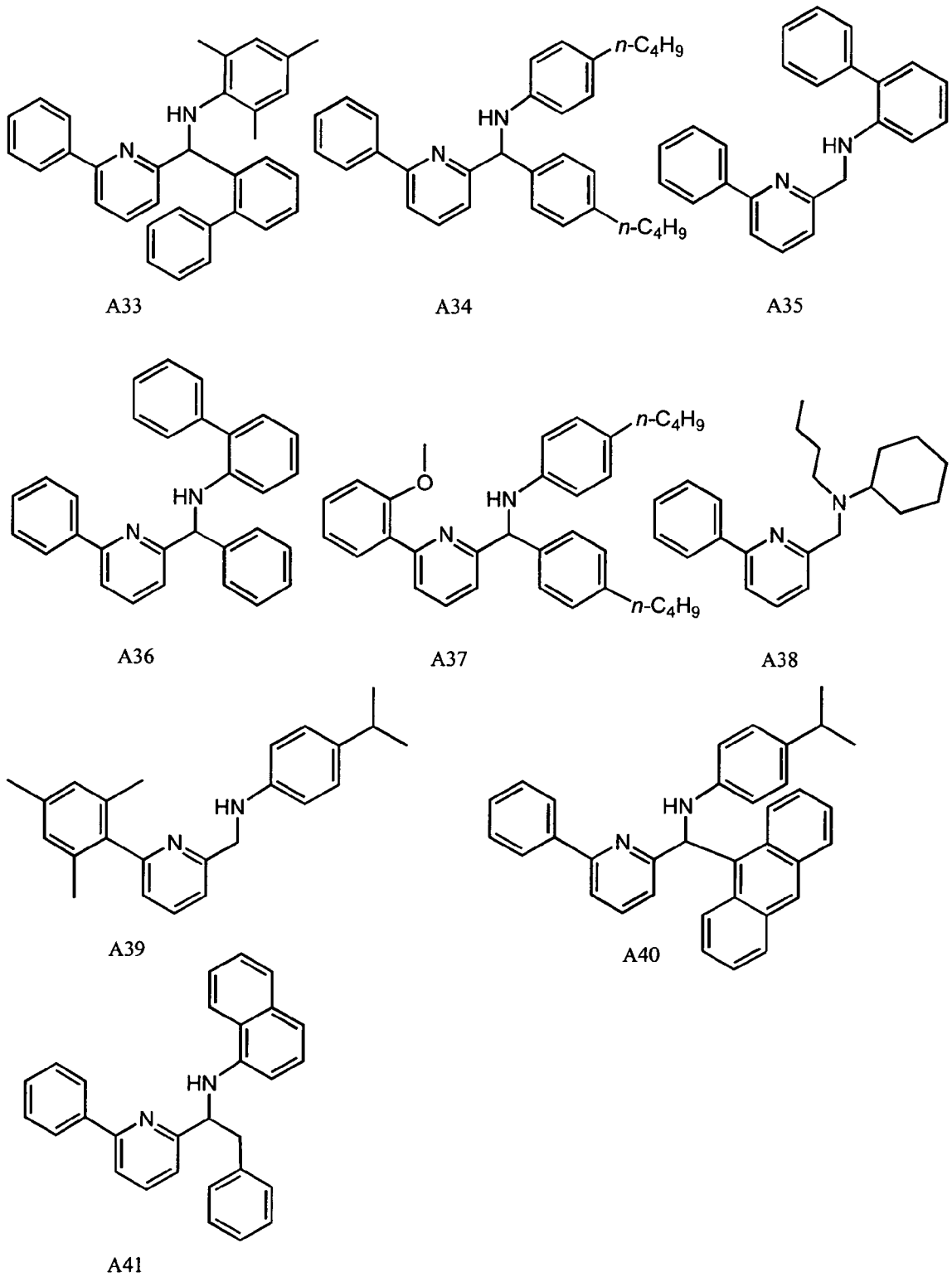
FIG. 9 illustrates pyridyl-amine ligands A33-A41.

Another exemplary process to produce 1-hexene using isopentane as the catalyst solvent with a polymer grade ethylene feed is shown in FIG. 5. The ethylene feed, C2 FEED, is 99.9% ethylene and 0.1% ethane (polymer grade feed) while the reaction selectivity to 1-hexene is 98% 1-hexene, 0.4% 1-octene and 1.6% decenes (both 1-decene and internals). The feed is mixed through a mixing device M2 with recycled ethylene S14 and isopentane IC5FEED and fed to the reactor. The reactor is operated at 90° C. and 400 psia (~2.76 MPaa) and is sized to achieve 80% per pass conversion of ethylene. The product stream from the reactor S5 is separated from unconverted ethylene using a flash drum F1 operated at 200 psia (~1.38 MPaa). The gas outlet S15 of the flash drum F1 is then recompressed through a compressor C1 at 400 psia (~2.76 MPaa) and recycled. The liquid stream S6 from the flash drum F1 is fed to a distillation column T1 operating at 60 psia (~0.4 MPaa). At the bottom of the distillation column 1-hexene and the heavier alpha-olefins are collected as the product stream from the column C6PRODUCT. The overhead vapors from the column S8 are then cooled at 0° C. using a heat exchanger E3 and conveyed to a second flash drum F2. The liquid phase S11 from the second flash drum F2 containing mostly ethylene is pumped using a pump P2 to 400 psia (~2.76 MPaa) and recycled back to the reactor. The gas phase, GASPURGE, is purged from the second flash drum F2. Homogeneous or slurry catalyst leaves with the 1-hexene product, C6PPRODUCT. A summary listing of stream flow rates and compositions is shown in Table 5.

TABLE 5

Flow Rates and Compositions

|  | Rate (kg/hr) | Ethylene | i-pentane | 1-hexene | 1-octene | Decenes | Ethane |
|---|---|---|---|---|---|---|---|
| Ethylene Feed | 15300 | 99.9% |  |  |  |  | 0.1% |
| Solvent Feed | 1000 |  | 100.00% |  |  |  |  |

TABLE 5-continued

Flow Rates and Compositions

|  | Rate (kg/hr) | Ethylene | i-pentane | 1-hexene | 1-octene | Decenes | Ethane |
|---|---|---|---|---|---|---|---|
| Recycle | 12800 | 41.14% | 53.57% | 4.55% |  |  | 0.74% |
| Product | 14300 | 0.00% | 0.29% | 98.41% | 0.30% | 1.00% |  |

Simulated Example 6

1-Hexene Product with Isopentane Solvent

Figure 13:
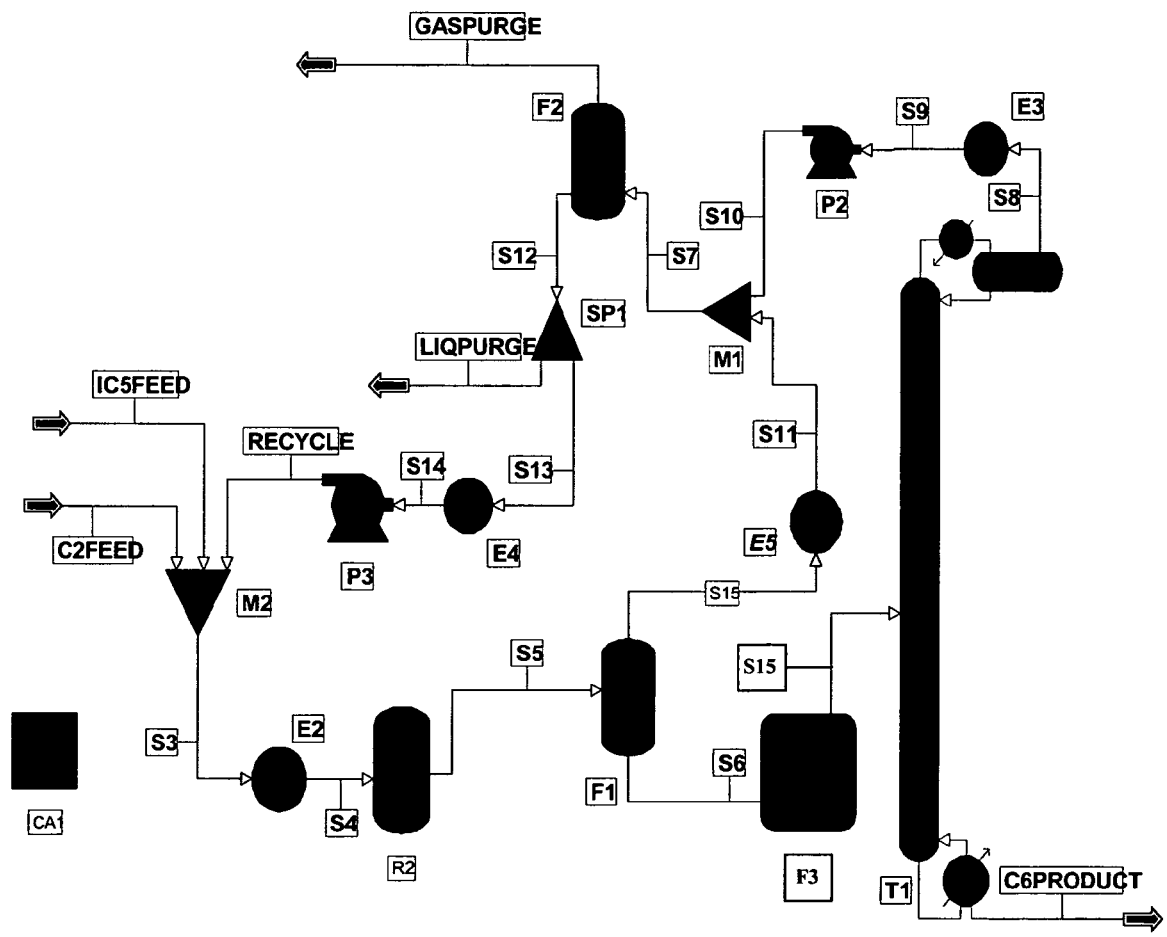
FIG. 13 depicts an exemplary process schematic of the process of the present invention for generating 1-hexene with isopentane as a solvent and/or diluent at high pressure.

Another exemplary process to produce 1-hexene using isopentane as the catalyst solvent with a polymer grade ethylene feed is shown in FIG. 13. Example 6 is similar to Example 3, except that Example 6 further includes a purification/filtration step between flash drum F1 and distillation column T1.

In this exemplary process, ethylene feed (C2FEED) is oligomerized to 1-hexene at 90° C. and 800 psia (~5.52 MPaa) using isopentane, IC5FEED, as a catalyst solvent. The C2FEED is 100% ethylene while the reaction selectivity to 1-hexene is 100%. The feed is mixed with recycled ethylene, isopentane and 1-hexene (Recycle) and fed to the reactor R2. The reactor R2 is operated at 90° C. and 800 psia (~5.52 MPaa) and is sized to achieve 80% per pass conversion of ethylene. The reactor product stream S5 is then fed to a flash drum F1 where the 1-hexene stream S6 is separated from the unconverted ethylene and catalyst solvent stream S15 at 150 psia (~1.03 MPaa). In cases where the bottoms stream S6 from the flash drum F1 contains oligomeric and/or polymeric contaminants, entrained catalyst, catalyst activator(s), catalytic decomposition products (e.g., metal-containing decomposition products, heteroatom-containing decomposition products, or a combination thereof), and/or other undesirable solid materials (or materials having considerably lower solubility in the solvent/diluent, e.g., isopentane, than the 1-hexene), the bottoms stream S6 may be fed into a purification section F3 before being fed to distillation column T1. The purification section F3 can advantageously contain at least a first filtration drum (and optionally a second filtration drum connected in parallel to the first filtration drum), at least a first catalyst adsorbent drum (and optionally a second catalyst adsorbent drum connected in parallel to the first catalyst adsorbent drum), or both.

Once through the purification system F3, the purified bottoms stream S15 can be sent to distillation column T1 for further treatment. The distillation column T1 can be operated at 60 psia (~0.4 MPaa) to complete the separation of 1-hexene, C6PRODUCT, from unconverted ethylene and catalyst solvent S8. The C6PRODUCT, including any homogeneous/slurry catalyst that was not removed by purification system F3, is collected at the bottom of the distillation column T1. If necessary, the C6PRODUCT can be further purified in a separate step. The overhead vapors of unconverted ethylene and catalyst solvent S8 from the distillation column T1 are condensed to form a liquid stream S9 using a heat exchanger E3 and transported using a pump P2 operated at 150 psia (~1.03 MPaa). The condensed unconverted ethylene and catalyst solvent stream S10 and a condensed overhead vapor stream S11 from the flash drum F1 are mixed through a mixing element M1. The combined stream S7 is separated into a gas and liquid phase in second flash drum F2. The liquid stream S13 is then subcooled through a heat exchanger E4, pumped back to 800 psia (~5.52 MPaa) using a pump P3 and recycled back to the reactor R2 as a recycle stream (RECYCLE).

Although Example 6 is described herein using the pure ethylene feed (100% ethylene) and high pressure (800 psia; ~5.52 MPaa) conditions disclosed in Example 3, Example 6 can alternately use polymer grade feed and/or lower pressures (e.g., both are used in Example 5). In such cases, the process schematic can be altered (e.g., similarly to the relevant portions of Example 5 corresponding to the alternate condition(s) used) and still remain within the present invention.

Where the purification system F3 in Example 6 contains a second drum of any type connected in parallel to the first drum of any type, it can be advantageous for the bottoms stream S6 to be routed in regular service to one of the two said drums, with the other of the two said drums remaining out of service, e.g., for purging, removing, deactivating, decomposing, and/or otherwise disposing of the contaminant(s) trapped therein. By this method, one purification system drum within its type can be operational at all times, advantageously reducing the down time and allowing the process to remain relatively continuous.

Examples 7-9

In-Line Comonomer Generation Processes

Figure 14:
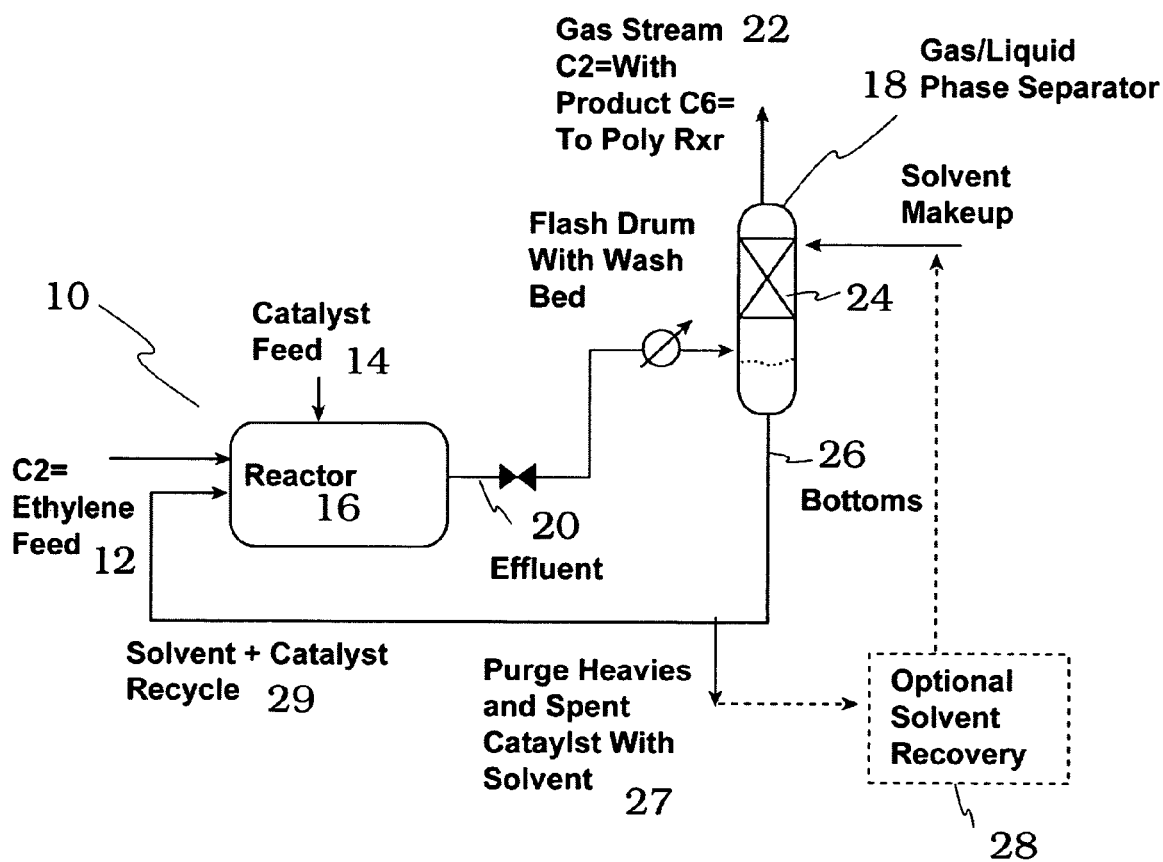
FIG. 14 depicts an illustrative schematic of the in-line process for comonomer generation utilizing a comonomer synthesis reactor and a downstream gas/liquid phase separator.

FIG. 14 depicts one exemplary process schematic of the improved in-line reaction and separation process 10 of the instant invention. In this configuration, ethylene feed 12 and catalyst feed 14 are fed to a comonomer synthesis reactor 16 (also referred to as an oligomerization reactor). The comonomer synthesis reactor 16 may be of various types, including, but not limited to a stirred tank reactor, more than one agitated vessel in series, and a long, thin tube-like contactor. If the catalyst is in the form of a fixed bed rather than slurry or solution, it may be contained in a contactor type of reactor.

In FIG. 14, the comonomer synthesis reactor 16 can be separate from the subsequent gas/liquid phase separator 18, which allows for separate control of reaction and separation conditions. The reactor temperature and pressure can be controlled to provide for acceptable reaction rates and selectivities, as well as to provide for phase separation.

With regard to catalyst solvent and/or diluent, there is flexibility as far as what catalyst solvent and/or diluent, if any, may be used. If a catalyst solvent and/or diluent is used, it should be less volatile than 1-hexene, and preferably less volatile than 1-octene, such that it is not swept out along with 1-hexene product. If 1-decene recovery is desired and the solvent and/or diluent is a hydrocarbon, then the solvent and/or diluent should have volatility different than 1-decene. On the other hand, if a solvent and/or diluent is used that is compatible with the polymerization process (e.g., isobutane and/or isopentane), it may be acceptable to allow large amounts of that solvent and/or diluent to leave the oligomerization reactor 16 along with the ethylene and 1-hexene.

Examples of other suitable catalyst solvents and/or diluents include, but are not limited to, $C_{5+}$ paraffins (preferable branched, e.g., isopentane), cycloparaffins, and aromatics. If the catalyst is in the form of a fixed bed or a slurry, it may not require additional extraneous solvent and/or diluent.

Reaction conditions can be selected to give from about 5% to about 75%, for example from about 10% to about 50%, single pass conversion of feed ethylene. Some of the chromium catalysts disclosed by Phillips, for example as disclosed in U.S. Pat. No. 5,543,375, permit a range of conditions. One exemplary, but non-limiting, set of conditions includes a reaction temperature from about 60° C. to about 150° C. or from about 80° C. to about 150° C., and a reaction pressure from about 300 psi (~21.1 kg/cm$^2$) to about 700 psi (~49.2 kg/cm$^2$). However, when utilizing an ethylene feed 12, a reaction temperature from about 60° C. to about 110° C. is typically preferred. Process conditions may be tuned to obtain desired phase separations as well as desired reactivity. Residence time is flexible, and can be chosen to provide a desired level of ethylene conversion. A range of average reaction residence times from about 30 minutes to about 4 hours is contemplated when using Phillips catalysts with a backmixed or pump around type of comonomer synthesis reactor 16, where most of the catalyst in the reactor 16 at a given time is not "fresh", but has been circulating around for some time before becoming deactivated. The range of reaction residence times may depend on other factors, such as the nature and amount of the catalyst.

The effluent 20 from the comonomer synthesis reactor 16 can be directed to the gas/liquid phase separator 18, where the gas stream 22 can exit the separator 18. A catalyst deactivator (e.g., water or alcohol) may be added to effluent 20. The gas stream 22 can contain comonomer, such as 1-hexene or 1-octene, as well as ethylene, typically predominately ethylene. The gas/liquid phase separator 18 may include, but is not limited to, a simple knockout vessel or other one-stage phase separator, but it may also include some trays or packing 24 in the zone where vapor is going up, with reflux liquid flowing down, to sharpen the $C_6/C_8$ or $C_8/C_{10}$ separation and also to wash down any catalyst or heavies that may have been carried upwards. In one embodiment, the ethylene can be bubbled through a stirred tank or pot, and can exit into a vapor space above the liquid.

In another alternative embodiment, some ethylene (not shown) can be added to the separator 18 below the feed entrance point, to strip out hexene or other comonomer (not shown) from the down-flowing solvent/diluent (not shown). The bottoms 26 from the separator 18, containing the catalyst, any undesired reaction products (in the case of 1-hexene production, such as 1-decene), and heavy solvent/diluent (if any), can be predominantly pumped back to the reactor 16. Heat exchangers (not shown) can be in-line with the pump around flow. Where waxy buildup is an issue, spare heat exchangers may also be provided. For both the bubbling pot and the pumparound type reactor/separator configurations described above, a small portion of the bottoms stream 26, containing purge heavies, spent catalyst with heavy solvent/diluent (if any) 27, and undesired reaction products (in the case of 1-hexene production, such as 1-decene), can be directed to an optional catalyst disposal and solvent/diluent recovery process 28. To minimize the load on solvent/diluent recovery process 28, it can be desirable to have a catalyst with high productivity (grams of olefin converted divided by grams of catalyst used).

In the gas stream 22 from the gas/liquid phase separator 18, ethylene (also referred to as $C_2^=$) is typically not recovered in high purity, which can save cryogenic ethylene column costs. Unconverted ethylene may be recycled back to the comonomer synthesis reactor 18, or may be sent on to another process (not shown), for example the downstream polyethylene polymerization process. Solvent/diluent and catalyst recycle 29 from the bottoms 26 of the gas/liquid phase separator 18 can be sent back to the oligomerization reactor 16. Most octene products can be swept out of the reactor or reactor/separator loop along with unconverted ethylene in the gas stream 22. The improved in-line reaction and separation process 10 typically does not include hexene/octene (also referred to as $C_6/C_8$) separation, because some of the trace octene byproduct may be used in the polymerization along with the hexene. Some trace octene may also exit the gas/liquid phase separator 18 in the bottoms stream 26 along with the decene (also referred to as $C_{10}$) byproduct.

The improved reaction and separation process of the instant invention for generating monomer in a pre-reactor immediately before the polymerization reactor can greatly simplify the required process. The exemplary process schematic of FIG. 14 permits the number of separation towers to be reduced versus the standalone concept of producing comonomer. This can result in significant operating and capital cost savings over conventional standalone processes for manufacturing comonomers, such as 1-hexene. An additional benefit of the instant invention is that the continual removal of hexene from the comonomer synthesis reactor zone can reduce the formation of decene byproduct. The improved reaction and separation process of the instant invention is believed to be compatible with a Phillips-type trimerization catalyst, but may also be useful with other homogeneous or heterogeneous selective oligomerization catalysts.

Figure 15:
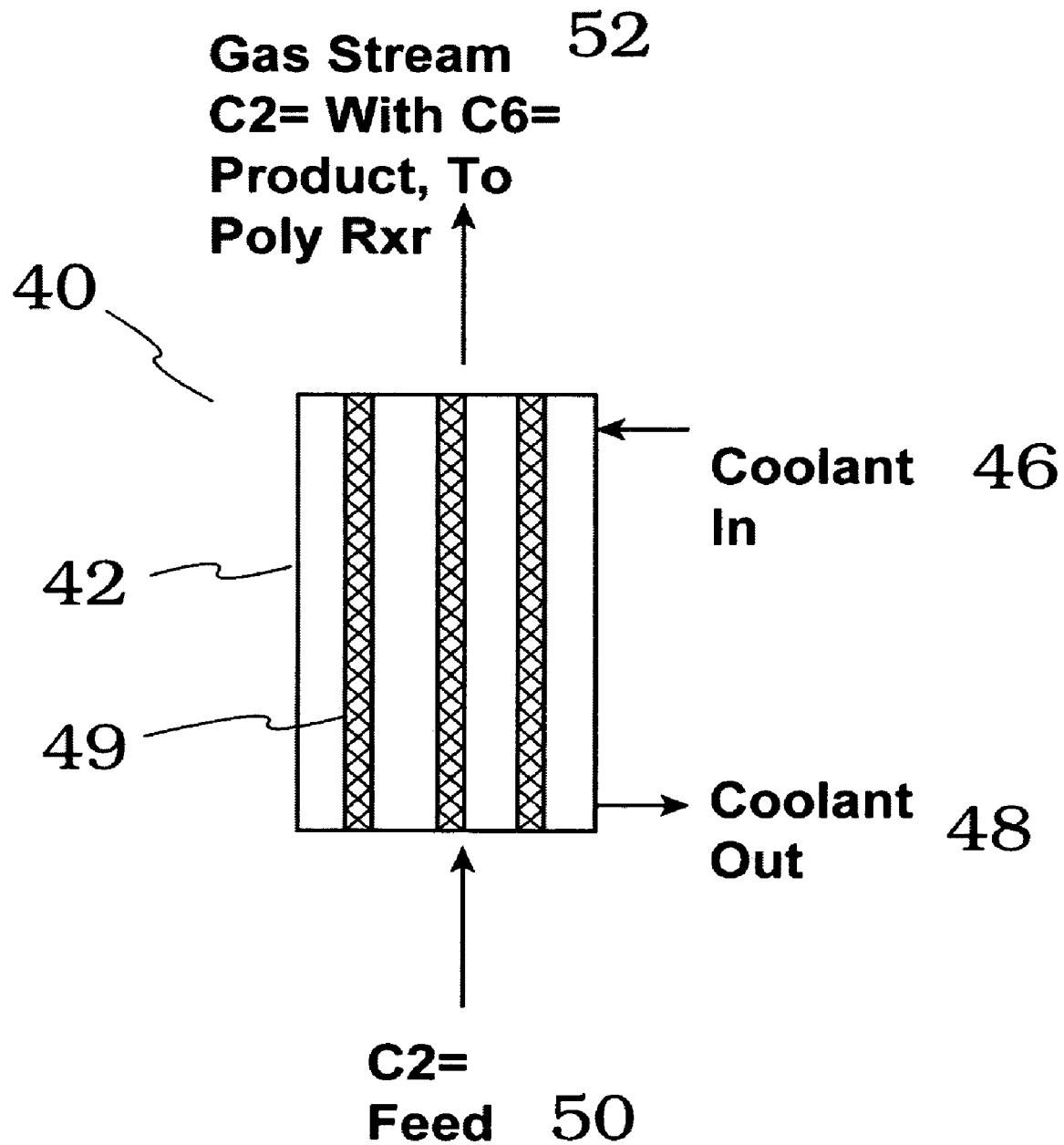
FIG. 15 depicts an illustrative schematic of the fixed bed reactors for in-line comonomer generation without a downstream gas/liquid phase separator in which catalyst is in the tubes with coolant.
Figure 16:
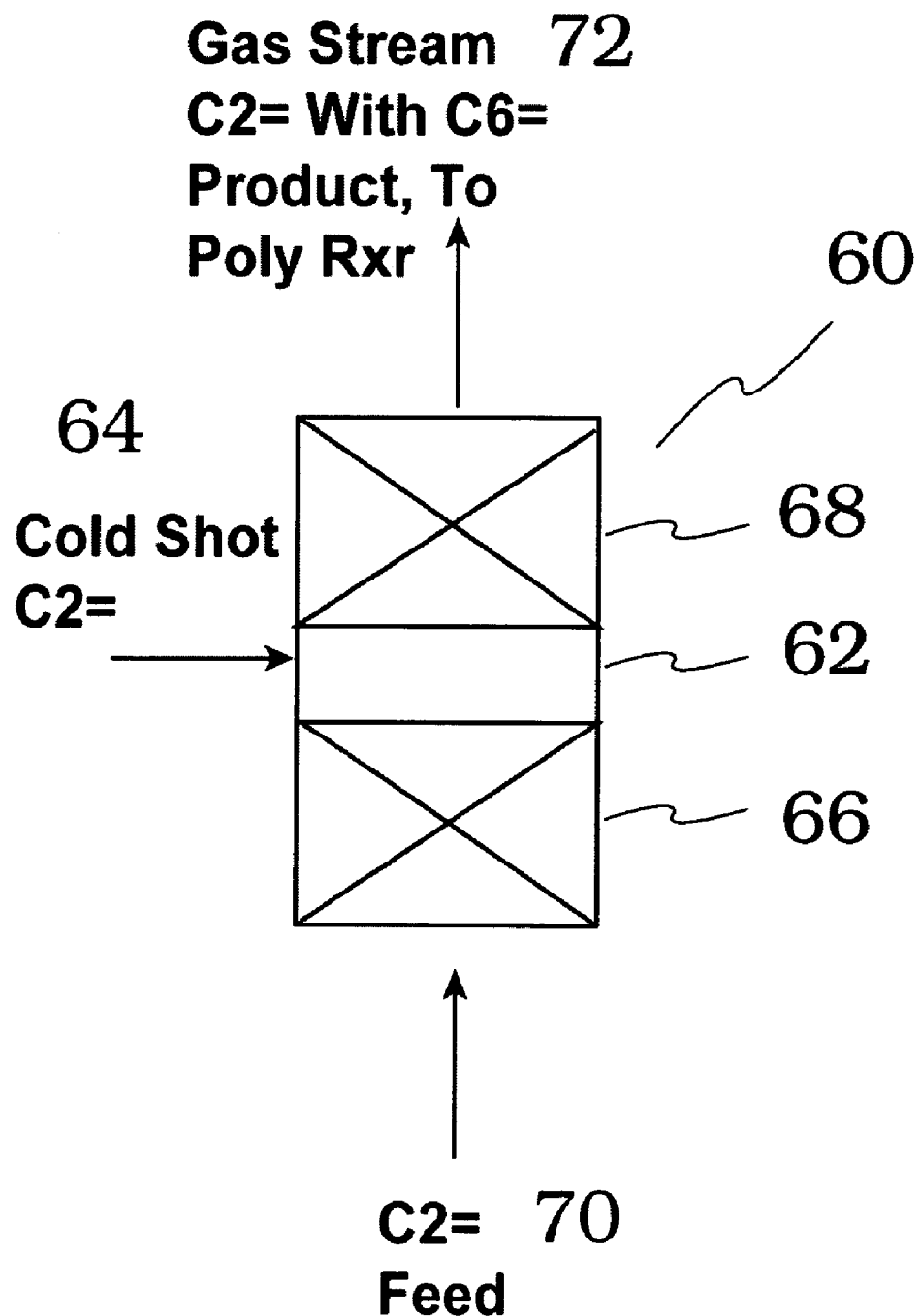
FIG. 16 depicts an illustrative schematic of the fixed bed reactors for in-line comonomer generation without a downstream gas/liquid phase separator in which cold shot cooling is utilized.

FIGS. 15 and 16 depict two other exemplary process schematics of improved in-line comonomer generation processes 40, 60 of the instant invention that do not include a gas/liquid phase separator. These embodiments represent an even more simplified approach. In both FIGS. 15 and 16, fixed bed reactor types are used, where the catalyst is in a fixed position, and where ethylene is fed past it. Catalyst types may include, but are not limited to, chromium, vanadium, tantalum, and titanium trimerization and/or tetramerization catalysts.

As comonomer (e.g., 1-hexene) is produced, it can be swept into the gas phase and carried out of the reactor. The precise form of the catalyst may include, but is not limited to, a solid, including active catalytic species anchored to a support, or in the form of a porous solid bed or monolith, which can be wetted with soluble catalyst in a heavy solvent and/or diluent. The solvent/diluent with catalyst may be trickled through the bed, to renew the solvent/diluent over time.

In gas/solids systems, temperature control can be an issue. Using 47 kcal/mol hexene for heat of reaction, it can be estimated that, for undiluted ethylene, a 10% conversion to hexene would generate about a 110° C. temperature rise, if there were no heat removal from the reactor. Also depicted in FIGS. 15 and 16 are two exemplary embodiments for managing the reaction heat generated.

In FIG. 15, the heat exchange capability is put into the reaction zone, for example, by loading the catalyst, e.g., in 1"-6" diameter tubes surrounded by a cooling medium. FIG. 15 depicts a comonomer synthesis reactor 42 with catalyst in tubes 44 with coolant. Coolant can enter and exit the comonomer synthesis reactor 42 through the coolant in 46 and coolant out 48 ports, respectively. Ethylene ($C_2^=$ feed) 50 can enter the comonomer synthesis reactor 42 and can react to form a gas stream 52 containing ethylene ($C_2^=$) along with comonomer, such as 1-hexene and/or 1-octene, which may be transferred directly to a downstream polyethylene polymerization reactor.

In FIG. 16, the reactor is divided into two or more catalyst beds, and cool feed or diluent can be injected before each stage. FIG. 16 depicts a comonomer synthesis reactor 62 with cold shot cooling of $C_2^=$ 64 between the first reaction stage 66 and the second reaction stage 68 of the comonomer synthesis reactor 62. Ethylene ($C_2^=$) feed 70 can enter the comonomer synthesis reactor 62 and again can react to form a gas stream 72 containing ethylene ($C_2^=$) along with comonomer, such as 1-hexene and/or 1-octene, which may be transferred directly to a downstream polyethylene polymerization reactor (not shown).

Simulated Example 10

In-Line Comonomer Generation Process w/Purification

Figure 17:
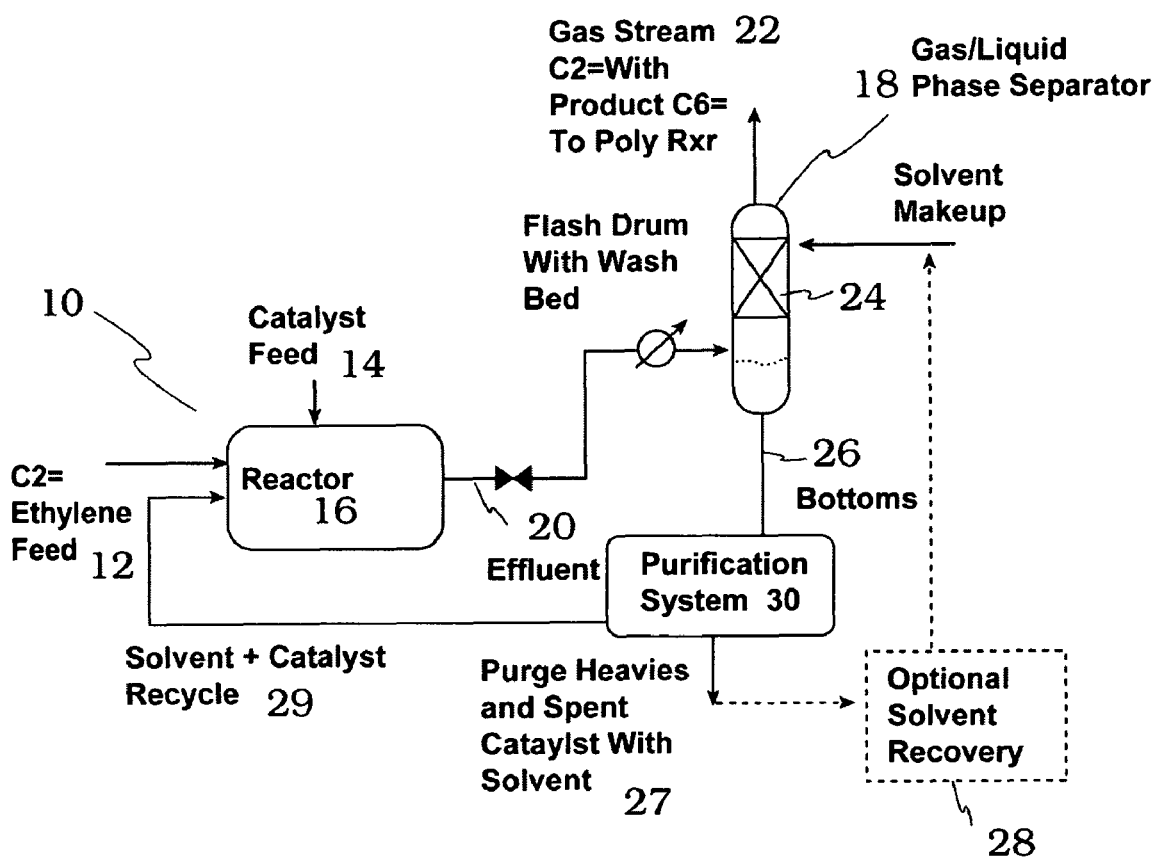
FIG. 17 depicts, an illustrative schematic of the in-line process for comonomer generation utilizing a comonomer synthesis reactor, a downstream gas/liquid phase separator, and a purification system.

The schematic representation in FIG. 17 is similar to that disclosed in FIG. 17, except that purification system 30 is included therein. Despite this, it should be understood that the exemplary embodiments for managing the reaction heat generated, as shown in FIGS. 15 and 16, may be added and/or substituted into the schematic of FIG. 17. The purification system 30, though shown in FIG. 17 downstream of the flash drum bottoms 26 but upstream of both the purge heavies and spent catalyst with solvent 27 and the solvent and catalyst recycle 29, may be located anywhere in the system both that is downstream of formation of the comonomer product and that is operable to trap and/or remove undesired contaminants from the system. Also, in FIG. 17, the solvent and catalyst recycle 29 may be recycling substantially, or only, solvent/diluent and little, or substantially no, catalyst. In an alternate embodiment, the solvent and catalyst recycle 29 may be optional but preferred.

In some embodiments, the purification system can include at least one filtration system (e.g., in the form of a drum; hereinafter "filtration drum" without any intent to limit). In a preferred embodiment, the at least one filtration drum can include at least two filtration drums in a parallel arrangement, at least one first filtration drum in fluid communication with the bottoms stream 26 and any subsequent distillation column or other downstream apparatus portion, and at least one second filtration drum not in fluid communication with the bottoms stream 26, and which is typically out of service for the purpose, e.g., of purging, removing, deactivating, decomposing, and/or otherwise disposing of contaminant(s) trapped therein.

Filtration drums according to the invention can typically have a primary purpose of filtering/trapping any polymeric and/or oligomeric material that is relatively insoluble in the solvent and/or diluent of the comonomer formation reaction process, and an optional secondary purpose of filtering/trapping relatively insoluble catalyst, catalyst activator(s), catalytic decomposition products, and/or other undesirable materials (typically organic, such as purge heavies) having considerably lower solubility in the solvent/diluent (e.g., isopentane) than the desired alpha olefin comonomer product (e.g., 1-hexene). One advantage of using a filtration drum includes a reduction and/or elimination of the need for post-distillation removal of solid/insoluble contaminants. Filtration drums are believed to have increased utility in reaction processes where relatively insoluble polymers/oligomers form, as it can be difficult to filter components from a highly soluble (e.g., homogeneous) composition.

In one embodiment, it may be advantageous to use as a filtration medium a material that can withstand the temperatures and (chemical) conditions associated with decomposition of polymers/oligomers, with deactivation of active catalyst, with exposure to active catalyst, or with combinations thereof. For example, the filtration medium can be comprised of a ceramic and/or a metal, optionally having a coating comprising a metal oxide, metal nitride, metal oxynitride, or the like, or combination thereof. In one embodiment, the filtration system can include commercially available systems, such as the CPF® (polymeric) filtration system and/or the ZHF® (centrifugal discharge) filtration system, both sold by the Pall Corporation.

Where filtration systems are present in the purification system according to the invention, one or more of the following steps may advantageously be accomplished in order to optimize the trapping/destroying/removing/deactivating efficiency of the purification system:

shutting down flow to a filtration drum, e.g., by taking a filtration drum containing some level of trapped contaminant(s) out of service (i.e., out of fluid communication with the bottoms stream 26 and optionally with any downstream distillation column or other apparatus portion), and, typically simultaneously, placing another filtration drum into service (i.e., into fluid communication with the bottoms stream 26 and any downstream apparatus portion);

depressurization of the filtration drum, e.g., through a top vent connection, which can advantageously serve to (further) cool any components trapped in the drum, e.g., for reducing the activity of any catalyst or any reactive chemical species present;

purging any volatile materials/contaminants from the filtration drum, e.g., with an inert gas and optionally with additional heat;

deactivating any residual catalyst activity, if present, e.g., by contacting with a deactivating agent such as liquid water, steam, oxygen, air, or a combination thereof, optionally also including contacting with an inert gas, e.g., in order to control any exotherm that may be caused by deactivation;

removing any remaining, typically solid, contaminants from the filtration medium for either recycling, further unrelated use, or disposal; and purging and/or drying (e.g., using heat and/or an inert gas) the filtration drum and medium to remove as much residual deactivation agent (e.g., oxygen and/or water) as possible, e.g., before returning flow to the filtration drum or putting it back into service, in order to reduce, inhibit, and/or prevent (re)circulation of deactivation agent into the system, e.g., which would typically reduce the activity and/or selectivity of the catalyst.

In other embodiments, the purification system can include at least one solid (e.g., catalyst) adsorbent system (e.g., in the form of a drum; hereinafter "catalyst adsorbent drum" without any intent to limit). In a preferred embodiment, the at least one catalyst adsorbent drum can include at least two catalyst adsorbent drums in a parallel arrangement, at least one first catalyst adsorbent drum in fluid communication with both the bottoms stream 26 and any subsequent apparatus portion for purification and/or recycling, and at least one second catalyst adsorbent drum not in fluid communication with the bottoms stream 26, and which is typically out of service for the purpose, e.g., of purging, removing, deactivating, decomposing, and/or otherwise disposing of contaminant(s) trapped therein.

Catalyst adsorbent drums according to the invention can typically have a primary purpose of adsorbing/trapping any inorganic and/or relatively insoluble solids (i.e., having considerably lower solubility in the solvent/diluent, e.g., isopentane, than the desired alpha olefin comonomer product, e.g., 1-hexene). One advantage of using a catalyst adsorbent drum includes a reduction and/or elimination of the need for post-distillation removal of solid/insoluble contaminants. Catalyst adsorbent drums are believed to have increased utility in reaction processes where catalyst and/or fines are likely to be entrained in the liquid bottoms from the gas/liquid phase separator.

The catalyst adsorbent drum typically contains a catalyst adsorbent agent, which can typically be a microporous solid, preferably having a specific surface area of at least 25 m²/g, more preferably at least 50 m²/g, for example at least 100 m²/g. Specific surface area can be measured, e.g., according to a standard nitrogen BET process, such as ASTM D3663-03 and/or D4567-03 for catalytic materials. Catalyst adsorbent agents can be characterized in at least two different categories—adsorbent agents for metals/metallic catalyst components, which can include (but are not limited to) Lewis bases; and adsorbent agents for heteroatom-containing catalyst ligand components (i.e., typically organic components, but always containing one or more heteroatoms selected from the group consisting of nitrogen, oxygen, sulfur, phosphorus, and combinations thereof), which can include (but are not limited to) Lewis acids. Examples of suitable catalyst adsorbent agents according to the invention include, but are not limited to, clay, alumina, silica, molecular sieve, cellulose and/or cellulosic materials, and the like, and combinations thereof.

In a preferred embodiment, when the bottoms stream 26 is fed into the purification system containing the catalyst adsorbent drum, the microporous solid can advantageously adsorb/trap at least 50 wt %, preferably at least 75 wt %, more preferably at least about 90 wt %, most preferably at least about 95 wt %, e.g., as much as 99 wt % or about 100 wt %, of the metal-containing solids, catalyst, and/or catalyst activator(s) from the stream entering the catalyst adsorbent drum.

In one embodiment, flash cooling of a solvent/diluent can be used to lower the temperature of the incoming stream before contacting the microporous solid in the catalyst adsorbent drum. Preferably, the incoming stream can contact the microporous solid at a temperature below 120° C., more preferably below 100° C., e.g., below 80° C., below 60° C., or below 50° C. The pressure requirements of the reaction system, including the pressure drop, reaction temperature, etc., can greatly depend on the solvent/diluent used.

In some embodiments, it can be both economical and advantageous to optimize the efficiency of the catalyst adsorbent drum by minimizing the amount of microporous solid therein, while optimally controlling the level of the metal-containing solids, heteroatom-containing solids, catalyst, and/or catalyst activator(s) that pass through the purification system and that flow into a downstream distillation column or subsequent process.

Where catalyst adsorbent systems are present in the purification system according to the invention, one or more of the following steps may advantageously be accomplished in order to optimize the trapping/destroying/removing/deactivating efficiency of the purification system:

shutting down flow to a filtration drum, e.g., by taking a catalyst adsorbent drum containing some level of trapped contaminant(s) out of service (i.e., out of fluid communication with the bottoms stream 26, and optionally with any apparatus portion downstream), and, typically simultaneously, placing another catalyst adsorbent drum into service (i.e., into fluid communication with both the bottoms stream 26 and any apparatus portion downstream);

depressurization of the catalyst adsorbent drum, e.g., through a top vent connection, which can advantageously serve to (further) cool any components trapped in the drum, e.g., for reducing the activity of any catalyst or any reactive chemical species present;

purging any volatile materials/contaminants from the catalyst adsorbent drum, e.g., with an inert gas and optionally with additional heat;

deactivating any reactive metals present, if any, and/or any residual catalyst activity, if present, e.g., by contacting with a deactivating agent such as liquid water, steam, oxygen, air, or a combination thereof, optionally also including contacting with an inert gas and/or a diluent, e.g., in order to control any exotherm that may be caused by deactivation;

oxidizing any trapped/remaining organic materials, if present, e.g., by contacting with an oxidizing agent such as an oxygen-containing gas, optionally also including contacting with an inert gas and/or a diluent, e.g., in order to control any exotherm that may be caused by oxidation, while typically seeking to avoid, if possible, apparatus damage and/or over-oxidation of metal-containing components to toxic substances (e.g., formation of $Cr^{VI}$ species);

removing any remaining contaminants from the catalyst adsorbent agent for either recycling, further unrelated use, or disposal; and purging and/or drying (e.g., using heat and/or an inert gas) the catalyst adsorbent drum and remaining catalyst adsorbent agent to remove as much residual deactivation agent (e.g., oxygen and/or water) as possible, e.g., before returning flow to the filtration drum or putting it back into service, in order to reduce, inhibit, and/or prevent (re)circulation of deactivation agent into the system, e.g., which would typically reduce the activity and/or selectivity of the catalyst.

In another embodiment, particularly where the bottoms stream 26 is in a relatively heterogeneous form (e.g., as a slurry) but also where it is in a relatively homogeneous form (e.g., as a solution), the purification system can advantageously include at least one filtration drum connected in series with at least one catalyst adsorbent drum. In another embodiment, the purification system can include at least two filtration drums connected in parallel with each other (at least one of which, e.g., would typically be out of service at any time), which at least two filtration drums are connected in series with at least two catalyst adsorbent drums connected in parallel with each other (at least one of which, e.g., would typically be out of service at any time).

Simulated Example 11

1-Hexene Production Via Ethylene Trimerization with Isopentane as Solvent

In Example 11, the apparatus/setup upon which the simulation was based is shown in the single synthesis reactor configuration in FIG. 18, although multiple reactor stages/configurations, such as those shown in FIGS. 19A and 19B, may alternately be used. Isopentane (2MBUTANE) was used as the diluent at a reaction pressure of about 200 psia (about 1.38 MPaa). The recycle rate of isopentane from the recovery section was about 200 lb/hr (about 90.0 kg/hr), and the reactor conversion was simulated to achieve a product hexene concentration of about 15.7 mol %. At these conditions, the evaporative cooling system was able to achieve a reaction temperature of about 89.9° C. The solubility of ethylene in the liquid phase at the reactor outlet was about 8.6 mol % (about 0.7 mol/L). The recycle rate of ethylene vapor from the reactor cooling system is about 169 lb/hr (about 76.8 kg/hr). Table 6 shows further details of the stream compositions and flow rates.

TABLE 6

| Stream Description | | S1 makeup C2= | S2 Rx liq prod | S3 Rx vap | S5 recycle vapor | S6 Rx cool liq | S12 hexene prod | S18 heavies | S19 recycle C2= and diluent |
|---|---|---|---|---|---|---|---|---|---|
| Phase | | Vapor | Liquid | Vapor | Vapor | Liquid | Liquid | Liquid | Liquid |
| Temperature | C. | 35.0 | 89.4 | 89.4 | 45.0 | 45.0 | 24.9 | 274.9 | 45.0 |
| Pressure | PSIA | 1203.8 | 200.0 | 200.0 | 200.0 | 200.0 | 150.0 | 120.0 | 200.0 |
| Total Molecular Weight | | 28.05 | 70.37 | 46.81 | 34.30 | 65.44 | 84.16 | 140.27 | 67.58 |
| Vapor Mole Fraction | | 1 | 0 | 1 | 1 | 0 | 0 | 0 | 0 |
| Flowrate | LB-MOL/HR | 1.78 | 3.68 | 8.26 | 4.94 | 3.32 | 0.58 | 0.01 | 3.09 |
| Total Mass Rate | LB/HR | 50.00 | 259.02 | 386.66 | 169.49 | 217.18 | 48.44 | 1.55 | 208.86 |
| Comp Mole Fractions | | | | | | | | | |
| ETHENE | | 1.0000 | 0.0858 | 0.5823 | 0.8583 | 0.1713 | 0.0000 | 0.0000 | 0.1022 |
| HEXENE 1 | | 0.0000 | 0.1564 | 0.0356 | 0.0052 | 0.0809 | 1.0000 | 0.0000 | 0.0000 |
| DECENE 1 | | 0.0000 | 0.0030 | 0.0000 | 0.0000 | 0.0001 | 0.0000 | 1.0000 | 0.0000 |
| 2MBUTANE | | 0.0000 | 0.7490 | 0.3755 | 0.1318 | 0.7384 | 0.0000 | 0.0000 | 0.8932 |
| 2MPROPANE | | 0.0000 | 0.0058 | 0.0065 | 0.0047 | 0.0093 | 0.0000 | 0.0000 | 0.0046 |
| Total Molar Comp. Rates | LB-MOL/HR | | | | | | | | |
| ETHENE | | 1.7823 | 0.3160 | 4.8098 | 4.2414 | 0.5684 | 0.0000 | 0.0000 | 0.3160 |
| HEXENE 1 | | 0.0000 | 0.5756 | 0.2942 | 0.0258 | 0.2685 | 0.5756 | 0.0000 | 0.0000 |
| DECENE 1 | | 0.0000 | 0.0111 | 0.0003 | 0.0000 | 0.0003 | 0.0000 | 0.0111 | 0.0000 |
| 2MBUTANE | | 0.0000 | 2.7571 | 3.1017 | 0.6513 | 2.4504 | 0.0000 | 0.0000 | 2.7605 |
| 2MPROPANE | | 0.0000 | 0.0213 | 0.0540 | 0.0231 | 0.0309 | 0.0000 | 0.0000 | 0.0142 |
| Total Weight Comp. Fractions | | | | | | | | | |
| ETHENE | | 1.0000 | 0.0342 | 0.3490 | 0.7020 | 0.0734 | 0.0000 | 0.0000 | 0.0424 |
| HEXENE 1 | | 0.0000 | 0.1870 | 0.0640 | 0.0128 | 0.1040 | 1.0000 | 0.0000 | 0.0000 |
| DECENE 1 | | 0.0000 | 0.0060 | 0.0001 | 0.0000 | 0.0002 | 0.0000 | 1.0000 | 0.0000 |
| 2MBUTANE | | 0.0000 | 0.7680 | 0.5788 | 0.2773 | 0.8141 | 0.0000 | 0.0000 | 0.9536 |
| 2MPROPANE | | 0.0000 | 0.0048 | 0.0081 | 0.0079 | 0.0083 | 0.0000 | 0.0000 | 0.0040 |

Although octene and polymer by-products are believed to be formed during the comonomer synthesis reaction, their content has not been reflected in the details of Table 6.

Simulated Example 12

1-Hexene Production Via Ethylene Trimerization with Isobutane as Solvent

In Example 12, the apparatus/setup upon which the simulation was based is shown in the single synthesis reactor configuration in FIG. 18, although multiple reactor stages/configurations, such as those shown in FIGS. 19A and 19B, may alternately be used. Isobutane (2MPROPANE) was used as the diluent at a reaction pressure of about 400 psia (about 2.76 MPaa). The recycle rate of isobutane from the recovery section was about 200 lb/hr (about 90.9 kg/hr), and the reactor conversion was simulated to achieve a product hexene concentration of 11.7 mol %. At these conditions, the evaporative cooling system was able to achieve a reaction temperature of about 85.8° C. The solubility of ethylene in the liquid phase at the reactor outlet was about 18.2 mol % (about 1.5 mol/L). The recycle rate of ethylene vapor from the reactor cooling system was about 79 lb/hr (about 35.9 kg/hr). Table 7 shows further details of the stream compositions and flow rates.

TABLE 7

| Stream Description | | S1 makeup C2= | S2 Rx liq prod | S3 Rx vap | S5 recy vapor | S6 Rx cool liq | S12 hexene prod | S18 heavies byprod | S19 recy C2= and diluent |
|---|---|---|---|---|---|---|---|---|---|
| Phase | | Vapor | Liquid | Vapor | Vapor | Liquid | Liquid | Liquid | Liquid |
| Temperature | C. | 35.0 | 85.8 | 85.8 | 45.0 | 45.0 | | 274.9 | 40.5 |
| Pressure | PSIA | 1203.8 | 400.0 | 400.0 | 400.0 | 400.0 | 150.0 | 120.0 | 150.0 |
| Total Molecular Weight | | 28.05 | 55.88 | 44.15 | 34.76 | 47.45 | 84.16 | 140.27 | 55.01 |
| Vapor Mole Fraction | | 1 | 0 | 1 | 1 | 0 | 0 | 0 | 0 |
| Flowrate | LB-MOL/HR | 1.78 | 4.92 | 8.73 | 2.27 | 6.46 | 0.58 | 0.01 | 3.11 |
| Total Mass Rate | LB/HR | 50.00 | 275.05 | 385.30 | 78.78 | 306.52 | 48.44 | 1.55 | 171.32 |
| Comp Mole Fractions | | | | | | | | | |
| ETHENE | | 1.0000 | 0.1819 | 0.4848 | 0.7790 | 0.3816 | 0.0000 | 0.0000 | 0.1036 |
| HEXENE 1 | | 0.0000 | 0.1169 | 0.0232 | 0.0024 | 0.0305 | 1.0000 | 0.0000 | 0.0000 |
| DECENE 1 | | 0.0000 | 0.0022 | 0.0000 | 0.0000 | 0.0001 | 0.0000 | 1.0000 | 0.0000 |
| 2MBUTANE | | 0.0000 | 0.0000 | 0.0000 | 0.0000 | 0.0000 | 0.0000 | 0.0000 | 0.0000 |
| 2MPROPANE | | 0.0000 | 0.6990 | 0.4920 | 0.2186 | 0.5879 | 0.0000 | 0.0000 | 0.8964 |
| Total Molar Comp. Rates | LB-MOL/HR | | | | | | | | |
| ETHENE | | 1.7823 | 0.8951 | 4.2303 | 1.7654 | 2.4649 | 0.0000 | 0.0000 | 0.3226 |
| HEXENE 1 | | 0.0000 | 0.5755 | 0.2026 | 0.0054 | 0.1972 | 0.5755 | 0.0000 | 0.0000 |

TABLE 7-continued

| Stream Description | S1 makeup C2= | S2 Rx liq prod | S3 Rx vap | S5 recy vapor | S6 Rx cool liq | S12 hexene prod | S18 heavies byprod | S19 recy C2= and diluent |
|---|---|---|---|---|---|---|---|---|
| DECENE 1 | 0.0000 | 0.0111 | 0.0004 | 0.0000 | 0.0004 | 0.0000 | 0.0111 | 0.0000 |
| 2MBUTANE | 0.0000 | 0.0000 | 0.0000 | 0.0000 | 0.0000 | 0.0000 | 0.0000 | 0.0000 |
| 2MPROPANE | 0.0000 | 3.4402 | 4.2931 | 0.4954 | 3.7976 | 0.0000 | 0.0000 | 2.7919 |
| Total Weight Comp. Fractions | | | | | | | | |
| ETHENE | 1.0000 | 0.0913 | 0.3080 | 0.6287 | 0.2256 | 0.0000 | 0.0000 | 0.0528 |
| HEXENE 1 | 0.0000 | 0.1761 | 0.0443 | 0.0058 | 0.0541 | 1.0000 | 0.0000 | 0.0000 |
| DECENE 1 | 0.0000 | 0.0056 | 0.0001 | 0.0000 | 0.0002 | 0.0000 | 1.0000 | 0.0000 |
| 2MBUTANE | 0.0000 | 0.0000 | 0.0000 | 0.0000 | 0.0000 | 0.0000 | 0.0000 | 0.0000 |
| 2MPROPANE | 0.0000 | 0.7270 | 0.6476 | 0.3655 | 0.7201 | 0.0000 | 0.0000 | 0.9472 |

Although octene and polymer by-products are believed to be formed during the comonomer synthesis reaction, their content has not been reflected in the details of Table 7.

Simulated Examples 13-14

1-Hexene Production Via Ethylene Trimerization with Propane as Solvent

In Example 13, the apparatus/setup upon which the simulation was based is shown in the single synthesis reactor configuration in FIG. 18, although multiple reactor stages/configurations, such as those shown in FIGS. 19A and 19B, may alternately be used. Propane was used as the diluent at a reaction pressure of about 500 psia (about 3.45 MPaa). The recycle rate of isobutane from the recovery section was about 70 lb/hr (about 31.8 kg/hr), and the reactor conversion was simulated to achieve a product hexene concentration of about 22.5 mol %. At these conditions, the evaporative cooling system was able to achieve a reaction temperature of about 80.5° C. The solubility of ethylene in the liquid phase at the reactor outlet was about 15.3 mol % (about 1.4 mol/L). The recycle rate of ethylene vapor from the reactor cooling system was about 27 lb/hr (about 12.3 kg/hr). Table 8 shows further details of the stream compositions and flow rates.

TABLE 8

| Stream Description | | S1 makeup C2= | S2 Rx liq prod | S3 Rx vap | S5 recycle C2= | S6 Rx cool liq | S12 hexene prod | S18 heavies | S19 recycle C2= and diluent |
|---|---|---|---|---|---|---|---|---|---|
| Phase | | Vapor | Liquid | Vapor | Vapor | Liquid | Liquid | Liquid | Liquid |
| Temperature | C. | 35.0 | 80.5 | 80.5 | 45.0 | 45.0 | 160.3 | 274.9 | 45.0 |
| Pressure | PSIA | 1203.8 | 500.0 | 500.0 | 500.0 | 500.0 | 150.0 | 120.0 | 500.0 |
| Total Molecular Weight | | 28.05 | 51.00 | 39.97 | 34.79 | 40.44 | 84.16 | 140.27 | 40.91 |
| Vapor Mole Fraction | | 1 | 0 | 1 | 1 | 0 | 0 | 0 | 0 |
| Flowrate | LB-MOL/HR | 1.78 | 2.57 | 9.51 | 0.79 | 8.73 | 0.58 | 0.01 | 1.98 |
| Total Mass Rate | LB/HR | 50.00 | 131.25 | 380.29 | 27.40 | 352.90 | 48.80 | 1.26 | 81.05 |
| Comp Mole Fractions | | | | | | | | | |
| ETHENE | | 1.0000 | 0.1531 | 0.3608 | 0.5919 | 0.3399 | 0.0000 | 0.0000 | 0.1988 |
| HEXENE 1 | | 0.0000 | 0.2254 | 0.0413 | 0.0047 | 0.0446 | 1.0000 | 0.0000 | 0.0000 |
| DECENE 1 | | 0.0000 | 0.0035 | 0.0001 | 0.0000 | 0.0001 | 0.0000 | 1.0000 | 0.0000 |
| 2MPROPANE | | 0.0000 | 0.0000 | 0.0000 | 0.0000 | 0.0000 | 0.0000 | 0.0000 | 0.0000 |
| PROPANE | | 0.0000 | 0.6181 | 0.5979 | 0.4034 | 0.6154 | 0.0000 | 0.0000 | 0.8012 |
| Total Molar Comp. Rates | LB-MOL/HR | | | | | | | | |
| ETHENE | | 1.7823 | 0.3940 | 3.4325 | 0.4661 | 2.9664 | 0.0000 | 0.0000 | 0.3940 |
| HEXENE 1 | | 0.0000 | 0.5799 | 0.3931 | 0.0037 | 0.3894 | 0.5799 | 0.0000 | 0.0000 |
| DECENE 1 | | 0.0000 | 0.0090 | 0.0006 | 0.0000 | 0.0006 | 0.0000 | 0.0090 | 0.0000 |
| 2MPROPANE | | 0.0000 | 0.0000 | 0.0000 | 0.0000 | 0.0000 | 0.0000 | 0.0000 | 0.0000 |
| PROPANE | | 0.0000 | 1.5905 | 5.6883 | 0.3176 | 5.3706 | 0.0000 | 0.0000 | 1.5874 |
| Total Weight Comp. Fractions | | | | | | | | | |
| ETHENE | | 1.0000 | 0.0842 | 0.2532 | 0.4773 | 0.2358 | 0.0000 | 0.0000 | 0.1364 |
| HEXENE 1 | | 0.0000 | 0.3718 | 0.0870 | 0.0114 | 0.0929 | 1.0000 | 0.0000 | 0.0000 |
| DECENE 1 | | 0.0000 | 0.0096 | 0.0002 | 0.0000 | 0.0002 | 0.0000 | 1.0000 | 0.0000 |
| 2MPROPANE | | 0.0000 | 0.0000 | 0.0000 | 0.0000 | 0.0000 | 0.0000 | 0.0000 | 0.0000 |
| PROPANE | | 0.0000 | 0.5344 | 0.6596 | 0.5113 | 0.6711 | 0.0000 | 0.0000 | 0.8636 |

Although octene and polymer by-products are believed to be formed during the comonomer synthesis reaction, their content has not been reflected in the details of Table 8.

In Example 14, the apparatus/setup upon which the simulation was based is shown in the single synthesis reactor configuration in FIG. 18, although multiple reactor stages/configurations, such as those shown in FIGS. 19A and 19B, may alternately be used. Propane is used as the diluent at a reaction pressure of about 570 psia (about 3.93 MPaa). The recycle rate of isobutane from the recovery section was about 70 lb/hr (about kg/hr), and the reactor conversion was simulated to achieve a product hexene concentration of about 21.3 mol %. At these conditions, the evaporative cooling system was able to achieve a reaction temperature of about 82.6° C. The solubility of ethylene in the liquid phase at the reactor outlet was about 19.7 mol % (about 1.8 mol/L). The recycle rate of ethylene vapor from the reactor cooling system was approximately zero; the reactor vapors were substantially/totally condensed. Table 9 shows further details of the stream compositions and flow rates.

TABLE 9

| Stream Description | | S1 makeup ethylene | S2 Rx liq prod | S3 Rx vap | S5 recycle ethylene | S6 Rx cool liq | S12 hexene prod | S18 heavies | S19 recycle C2= and diluent |
|---|---|---|---|---|---|---|---|---|---|
| Phase | | Vapor | Liquid | Vapor | Unknown | Liquid | Liquid | Liquid | Liquid |
| Temperature | C. | 35.0 | 82.6 | 82.6 | n/a | 45.0 | 160.3 | 274.9 | 45.0 |
| Pressure | PSIA | 1203.8 | 570.0 | 570.0 | n/a | 570.0 | 150.0 | 120.0 | 570.0 |
| Total Molecular Weight | | 28.05 | 49.83 | 39.23 | n/a | 39.23 | 84.16 | 140.27 | 40.06 |
| Vapor Mole Fraction | | 1 | 0 | 1 | n/a | 0 | 0 | 0 | 0 |
| Flowrate | LB-MOL/HR | 1.782 | 2.709 | 9.391 | n/a | 9.391 | 0.577 | 0.010 | 2.121 |
| Total Mass Rate | LB/HR | 50.000 | 134.984 | 368.390 | n/a | 368.390 | 48.602 | 1.389 | 84.968 |
| Comp Mole Fractions | | | | | | | | | |
| ETHENE | | 1.0000 | 0.1970 | 0.4124 | n/a | 0.4124 | 0.0000 | 0.0000 | 0.2516 |
| HEXENE 1 | | 0.0000 | 0.2132 | 0.0434 | n/a | 0.0434 | 1.0000 | 0.0000 | 0.0000 |
| DECENE 1 | | 0.0000 | 0.0037 | 0.0001 | n/a | 0.0001 | 0.0000 | 1.0000 | 0.0000 |
| 2MPROPANE | | 0.0000 | 0.0000 | 0.0000 | n/a | 0.0000 | 0.0000 | 0.0000 | 0.0000 |
| PROPANE | | 0.0000 | 0.5862 | 0.5441 | n/a | 0.5441 | 0.0000 | 0.0000 | 0.7484 |
| Total Molar Comp. Rates | LB-MOL/HR | | | | | | | | |
| ETHENE | | 1.7823 | 0.5336 | 3.8727 | n/a | 3.8727 | 0.0000 | 0.0000 | 0.5336 |
| HEXENE 1 | | 0.0000 | 0.5775 | 0.4075 | n/a | 0.4075 | 0.5775 | 0.0000 | 0.0000 |
| DECENE 1 | | 0.0000 | 0.0099 | 0.0008 | n/a | 0.0008 | 0.0000 | 0.0099 | 0.0000 |
| 2MPROPANE | | 0.0000 | 0.0000 | 0.0000 | n/a | 0.0000 | 0.0000 | 0.0000 | 0.0000 |
| PROPANE | | 0.0000 | 1.5880 | 5.1100 | n/a | 5.1100 | 0.0000 | 0.0000 | 1.5874 |
| Total Weight Comp. Fractions | | | | | | | | | |
| ETHENE | | 1.0000 | 0.1109 | 0.2949 | n/a | 0.2949 | 0.0000 | 0.0000 | 0.1762 |
| HEXENE 1 | | 0.0000 | 0.3601 | 0.0931 | n/a | 0.0931 | 1.0000 | 0.0000 | 0.0000 |
| DECENE 1 | | 0.0000 | 0.0103 | 0.0003 | n/a | 0.0003 | 0.0000 | 1.0000 | 0.0000 |
| 2MPROPANE | | 0.0000 | 0.0000 | 0.0000 | n/a | 0.0000 | 0.0000 | 0.0000 | 0.0000 |
| PROPANE | | 0.0000 | 0.5188 | 0.6117 | n/a | 0.6117 | 0.0000 | 0.0000 | 0.8238 |

Although octene and polymer by-products are believed to be formed during the comonomer synthesis reaction, their content has not been reflected in the details of Table 9.

Simulated Example 15

1-Hexene Production Via Ethylene Trimerization with Isopentane as Solvent

This example is a simulation of the overall process incorporating evaporative cooling, polymer filtration, and catalyst adsorption, using isopentane (iC5) as the solvent/diluent, and with reactor conditions of about 815 psia (about 5.62 MPaa) and about 80° C. The apparatus/setup upon which the simulation was based is shown in the single synthesis reactor configuration in FIG. 20, although multiple reactor stages/configurations, such as those shown in FIGS. 19A and 19B, may alternately be used. Table 10 shows further details of the stream compositions and flow rates.

TABLE 10

| Stream Description | | Stream Name | | | | | | |
|---|---|---|---|---|---|---|---|---|
| | | S1<br>C2<br>makeup | S2<br>Pump<br>Sucl | S3<br>Comp<br>Sucl | S4<br>Comp<br>Disch | S5<br>Pump<br>Disch | S6<br>Warm<br>Rx Fd | S7<br>Cool<br>Rx Fd |
| Phase | | Vapor | Liquid | Vapor | Vapor | Liquid | Mixed | Liquid |
| Temperature | C. | 35.00 | 33.26 | 33.26 | 151.54 | 36.31 | 100.94 | 40.00 |
| Pressure | PSIA | 300.00 | 110.00 | 110.00 | 850.00 | 850.00 | 850.00 | 850.00 |
| Total Molecular Weight | | 28.054 | 67.514 | 35.714 | 35.714 | 67.514 | 50.306 | 50.306 |
| Liquid Weight Fraction | | 0.000 | 1.000 | 0.000 | 0.000 | 1.000 | 0.934 | 1.000 |
| Flowrate | KG-MOL/HR | 100.000 | 227.335 | 268.082 | 268.082 | 227.335 | 495.418 | 495.418 |
| Flowrate | KG/HR | 2805.380 | 15348.258 | 9574.220 | 9574.220 | 15348.258 | 24922.477 | 24922.477 |
| mole fraction | | | | | | | | |
| ETHYLENE | | 1.0000 | 0.1051 | 0.6263 | 0.8263 | 0.1051 | 0.4954 | 0.4954 |
| ISOPENTANE | | 0.0000 | 0.8949 | 0.1737 | 0.1737 | 0.8949 | 0.5046 | 0.5048 |
| HEXENE 1 | | 0.0000 | 0.0000 | 0.0000 | 0.0000 | 0.0000 | 0.0000 | 0.0000 |
| OCTENE 1 | | 0.0000 | 0.0000 | 0.0000 | 0.0000 | 0.0000 | 0.0000 | 0.0000 |
| DECENE | | 0.0000 | 0.0000 | 0.0000 | 0.0000 | 0.0000 | 0.0000 | 0.0000 |
| POLYMER | | 0.0000 | 0.0000 | 0.0000 | 0.0000 | 0.0000 | 0.0000 | 0.0000 |
| molar rates | KG-MOL/HR | | | | | | | |
| ETHYLENE | | 100.00 | 23.90 | 221.51 | 221.51 | 23.90 | 245.42 | 245.42 |
| ISOPENTANE | | 0.00 | 203.43 | 46.57 | 46.57 | 203.43 | 250.00 | 250.00 |
| HEXENE 1 | | 0.00 | 0.00 | 0.00 | 0.00 | 0.00 | 0.00 | 0.00 |
| OCTENE 1 | | 0.00 | 0.00 | 0.00 | 0.00 | 0.00 | 0.00 | 0.00 |
| DECENE | | 0.00 | 0.00 | 0.00 | 0.00 | 0.00 | 0.00 | 0.00 |
| POLYMER | | 0.00 | 0.00 | 0.00 | 0.00 | 0.00 | 0.00 | 0.00 |
| Weight Comp. Fractions | | | | | | | | |
| ETHYLENE | | 1.0000 | 0.0437 | 0.6491 | 0.6491 | 0.0437 | 0.2763 | 0.2763 |
| ISOPENTANE | | 0.0000 | 0.9563 | 0.3509 | 0.3509 | 0.9583 | 0.7237 | 0.7237 |
| HEXENE 1 | | 0.0000 | 0.0000 | 0.0000 | 0.0000 | 0.0000 | 0.0000 | 0.0000 |
| OCTENE 1 | | 0.0000 | 0.0000 | 0.0000 | 0.0000 | 0.0000 | 0.0000 | 0.0000 |
| DECENE | | 0.0000 | 0.0000 | 0.0000 | 0.0000 | 0.0000 | 0.0000 | 0.0000 |
| POLYMER | | 0.0000 | 0.0000 | 0.0000 | 0.0000 | 0.0000 | 0.0000 | 0.0000 |
| Total Actual Density | KG/M3 | 25.530 | 593.624 | 11.397 | 71.584 | 597.613 | 359.213 | 524.316 |
| Vapor Viscosity | PAS | 0.00001 | n/a | 0.00001 | 0.00002 | n/a | 0.00002 | n/a |
| Liquid Viscosity | PAS | n/a | 0.00018 | n/a | n/a | 0.00019 | 0.00006 | 0.00012 |

| Stream Description | | Stream Name | | | | | |
|---|---|---|---|---|---|---|---|
| | | S8<br>Rx Eff | S9<br>Eff Flash | S10<br>Fish Vap | S11<br>Fish Liq | S12<br>Col Liq Fd | S13<br>Polymer |
| Phase | | Liquid | Mixed | Vapor | Liquid | Mixed | Liquid |
| Temperature | C. | 80.00 | 51.26 | 51.26 | 51.26 | 51.25 | 45.00 |
| Pressure | PSIA | 815.00 | 130.00 | 130.00 | 130.00 | 130.00 | 130.00 |
| Total Molecular Weight | | 58.185 | 58.185 | 38.675 | 69.497 | 69.421 | 280.538 |
| Liquid Weight Fraction | | 1.000 | 0.758 | 0.000 | 1.000 | 1.000 | 1.000 |
| Flowrate | KG-MOL/HR | 428.329 | 428.329 | 157.193 | 271.136 | 271.038 | 0.098 |
| Flowrate | KG/HR | 24922.473 | 24922.473 | 6079.354 | 18843.121 | 18815.582 | 27.540 |
| mole fraction | | | | | | | |
| ETHYLENE | | 0.3392 | 0.3392 | 0.7623 | 0.0939 | 0.0939 | 0.0000 |
| ISOPENTANE | | 0.5837 | 0.5837 | 0.2260 | 0.7910 | 0.7913 | 0.0000 |
| HEXENE 1 | | 0.0764 | 0.0764 | 0.0117 | 0.1139 | 0.1140 | 0.0000 |
| OCTENE 1 | | 0.0003 | 0.0003 | 0.0000 | 0.0004 | 0.0004 | 0.0000 |
| DECENE | | 0.0002 | 0.0002 | 0.0000 | 0.0004 | 0.0004 | 0.0000 |
| POLYMER | | 0.0002 | 0.0002 | 0.0000 | 0.0004 | 0.0000 | 1.0000 |
| molar rates | KG-MOL/HR | | | | | | |
| ETHYLENE | | 145.29 | 145.29 | 119.83 | 25.45 | 25.45 | 0.00 |
| ISOPENTANE | | 250.00 | 250.00 | 35.52 | 214.48 | 214.48 | 0.00 |
| HEXENE 1 | | 32.72 | 32.72 | 1.84 | 30.89 | 30.69 | 0.00 |
| OCTENE 1 | | 0.12 | 0.12 | 0.00 | 0.12 | 0.12 | 0.00 |
| DECENE | | 0.10 | 0.10 | 0.00 | 0.10 | 0.10 | 0.00 |
| POLYMER | | 0.10 | 0.10 | 0.00 | 0.10 | 0.00 | 0.10 |
| Weight Comp. Fractions | | | | | | | |
| ETHYLENE | | 0.1635 | 0.1635 | 0.5530 | 0.0379 | 0.0380 | 0.0000 |
| ISOPENTANE | | 0.7237 | 0.7237 | 0.4216 | 0.8212 | 0.8224 | 0.0000 |
| HEXENE 1 | | 0.1105 | 0.1105 | 0.0254 | 0.1380 | 0.1382 | 0.0000 |
| OCTENE 1 | | 0.0006 | 0.0006 | 0.0000 | 0.0007 | 0.0007 | 0.0000 |
| DECENE | | 0.0006 | 0.0006 | 0.0000 | 0.0007 | 0.0007 | 0.0000 |
| POLYMER | | 0.0011 | 0.0011 | 0.0000 | 0.0015 | 0.0000 | 1.0000 |
| Total Actual Density | KG/M3 | 509.655 | 53.234 | 13.948 | 583.223 | 581.281 | 778.225 |
| Vapor Viscosity | PAS | n/a | 0.00001 | 0.00001 | n/a | 0.00001 | n/a |
| Liquid Viscosity | PAS | 0.00010 | 0.00016 | n/a | 0.00016 | 0.00016 | 0.00337 |

TABLE 10-continued

| Stream Description | | S14<br>Col 1 OH | S15<br>Col 1 Btms | S16<br>iC5 makeup | S17<br>Col 1 Recy | S18<br>iC5 purge |
|---|---|---|---|---|---|---|
| Phase | | Mixed | Liquid | Liquid | Mixed | Liquid |
| Temperature | C. | 40.00 | 144.35 | 40.00 | 40.08 | 40.00 |
| Pressure | PSIA | 110.00 | 110.00 | 300.00 | 110.00 | 110.00 |
| Total Molecular Weight | | 55.943 | 84.433 | 72.150 | 55.943 | 72.150 |
| Liquid Weight Fraction | | 0.733 | 1.000 | 1.000 | 0.733 | 1.000 |
| Flowrate | KG-MOL/HR | 395.287 | 32.943 | 100.000 | 395.287 | 100.000 |
| Flowrate | KG/HR | 22113.439 | 2781.495 | 7215.030 | 22113.434 | 7215.033 |
| mole fraction | | | | | | |
| ETHYLENE | | 0.3675 | 0.0000 | 0.0000 | 0.3675 | 0.0000 |
| ISOPENTANE | | 0.6325 | 0.0000 | 1.0000 | 0.6325 | 1.0000 |
| HEXENE 1 | | 0.0000 | 0.9933 | 0.0000 | 0.0000 | 0.0000 |
| OCTENE 1 | | 0.0000 | 0.0037 | 0.0000 | 0.0000 | 0.0000 |
| DECENE | | 0.0000 | 0.0030 | 0.0000 | 0.0000 | 0.0000 |
| POLYMER | | 0.0000 | 0.0000 | 0.0000 | 0.0000 | 0.0000 |
| molar rates | KG-MOL/HR | | | | | |
| ETHYLENE | | 145.29 | 0.00 | 0.00 | 145.29 | 0.00 |
| ISOPENTANE | | 250.00 | 0.00 | 100.00 | 250.00 | 100.00 |
| HEXENE 1 | | 0.00 | 32.72 | 0.00 | 0.00 | 0.00 |
| OCTENE 1 | | 0.00 | 0.12 | 0.00 | 0.00 | 0.00 |
| DECENE | | 0.00 | 0.10 | 0.00 | 0.00 | 0.00 |
| POLYMER | | 0.00 | 0.00 | 0.00 | 0.00 | 0.00 |
| Weight Comp. Fractions | | | | | | |
| ETHYLENE | | 0.1843 | 0.0000 | 0.0000 | 0.1643 | 0.0000 |
| ISOPENTANE | | 0.8157 | 0.0000 | 1.0000 | 0.8157 | 1.0000 |
| HEXENE 1 | | 0.0000 | 0.9901 | 0.0000 | 0.0000 | 0.0000 |
| OCTENE 1 | | 0.0000 | 0.0050 | 0.0000 | 0.0000 | 0.0000 |
| DECENE | | 0.0000 | 0.0050 | 0.0000 | 0.0000 | 0.0000 |
| POLYMER | | 0.0000 | 0.0000 | 0.0000 | 0.0000 | 0.0000 |
| Total Actual Density | KG/M3 | 41.801 | 537.626 | 601.433 | 41.754 | 599.600 |
| Vapor Viscosity | PAS | 0.00001 | n/a | n/a | 0.00001 | n/a |
| Liquid Viscosity | PAS | 0.00017 | 0.00010 | 0.00019 | 0.00017 | 0.00019 |

Figure 20:
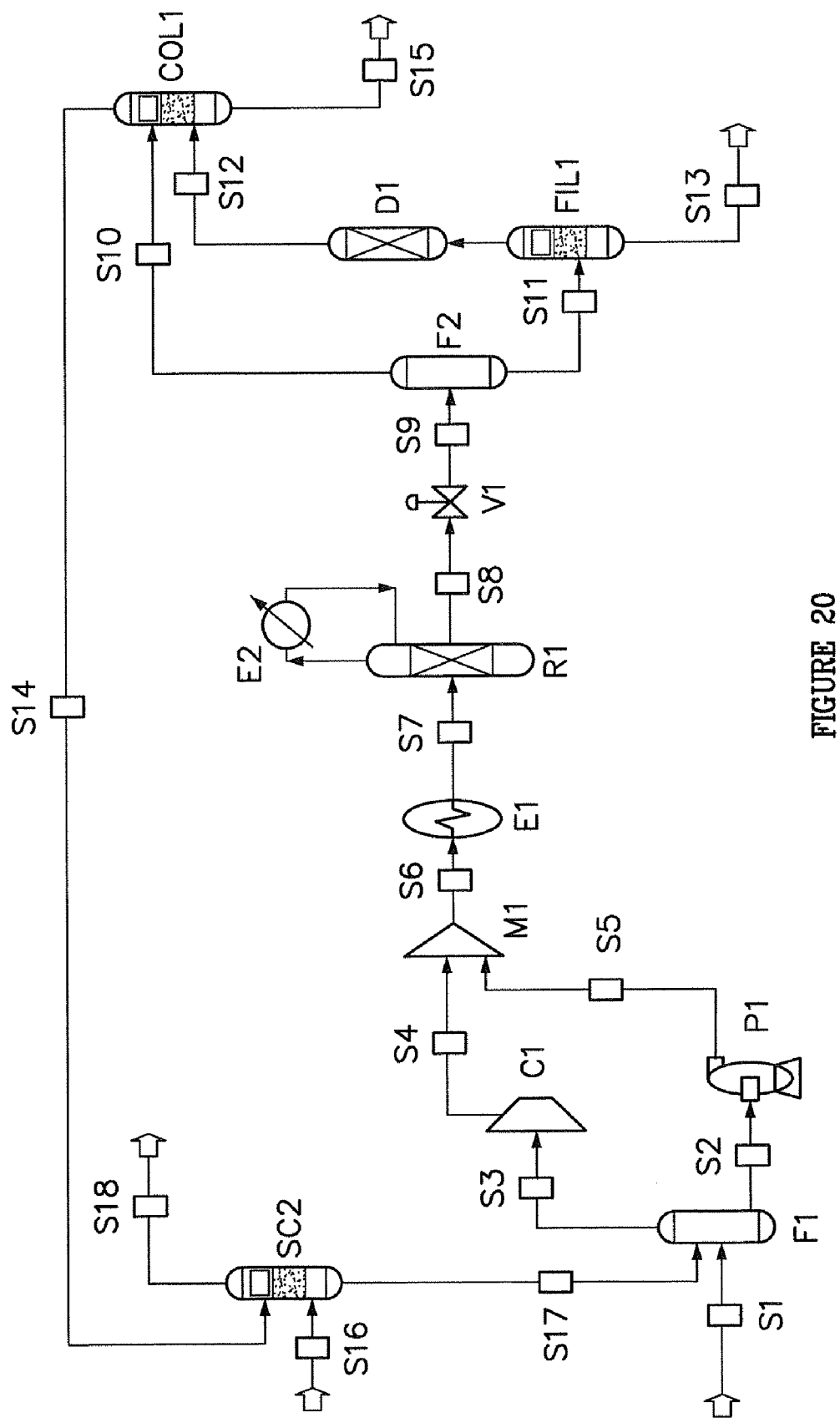
FIG. 20 depicts an exemplary process schematic of the process of the present invention for generating 1-hexene with isopentane as a solvent and/or diluent

As illustrated in FIG. 20, makeup ethylene stream S1 combines with the recycle ethylene and isopentane stream S17 to feed flash drum F1. The liquid product from F1, stream S2, is pumped with pump P1 to form pressurized liquid stream S5, and the vapor from F1, stream S3, is compressed with compressor C1 to form pressurized vapor stream S4. Streams S4 and S5 are combined in mixer M1 forming a combined reactor feed stream S6. Stream S6 is pre-cooled in exchanger E1 to form a liquid stream S7 which feeds reactor R1. Heat generated by the reaction vaporizes some of the liquid in R1; this vapor is cooled and condensed in exchanger E2, and returned to R1 as reflux. At the reaction conditions chosen in this example, all of the vapor generated is condensed and no net vapor effluent is generated from the reactor. The liquid reactor effluent stream S8 flows through a control valve V1, where the pressure is reduced, forming stream S9. The reduction in pressure results in the formation of some vapor; the vapor and liquid are separated in flash drum F2, forming streams S10 and S11, respectively. The liquid stream S11 contains any polymer byproduct and the remains of the catalyst components. The polymer is removed in filter FILL and the catalyst components are adsorbed in vessel D1, forming liquid stream S12. The vapor stream S10 and liquid stream S12 are both fed to a distillation column COL1, where the unreacted ethylene and the isopentane diluent are taken as overhead products, and the hexene and olefin byproducts (octene and decene) are taken as bottoms product stream S15. In this example, the overhead of the column produces both a liquid and vapor distillate product; these streams are combined to form stream S14. Streams S16 and S18 are dummy isopentane makeup and purge streams, and are included in the simulation to make the calculations work as desired. After the dummy makeup and purge, stream S14 becomes stream S17. Please note that streams S14 and S17 are otherwise identical.

In contrast to Examples 11-14, Example 15 and Table 10 consider not only the contens of ethylene, 1-hexene, decene, and solvent/diluent, but also 1-octene and polymer byproducts as well. The yield of 1-hexene from ethylene in this example is about 98.0 wt % (about 99.1 mol %), based on the total product weight (not including unreacted ethylene and solvent/diluent) in the reactor effluent (S9 in Example 15), while the by-product impurities are present in the following contents: about 0.5 wt % (about 0.3-0.4 mol %) octene; about 0.5 wt % (about 0.3 mol %) decene; and about 1 wt % (about 0.3 mol %) polymeric by-product.

In comonomer synthesis reaction systems similar to that schematically represented in Example 15, the yield of 1-hexene from ethylene can advantageously be at least 97.5 wt %, for example at least 97.8 wt %, at least 98.0 wt %, from 97.5 wt % to 99.0 wt %, from 97.8 wt % to 98.8 wt %, from 97.5 wt % to 99.5 wt %, or from 97.8 wt % to 99.0 wt %.

In Examples 11-15, and indeed in any of the methods according to the invention set forth herein, evaporative cooling may be utilized to reduce, inhibit, and/or prevent fouling on one or more cooling surfaces in and/or near the reactor (e.g., reactor walls, conduits leading to and/or from the reactor, and the like). In preferred embodiments, evaporative cooling is utilized (1) by selecting a solvent and/or diluent that having a boiling temperature lower than the boiling temperature of the desired olefin comonomer product(s) (at the specified reactor pressure) and (2) by using a reactor configured (i) to handle/allow evaporation of the solvent/diluent by absorption of heat present/generated in/near the reactor, (ii) to handle/allow cooling and condensation of the evaporated solvent/diluent (e.g., on the cooling surfaces, and optionally but preferably (iii) to handle/allow return of the condensed solvent/diluent to the reactor, e.g., as reflux. Without being bound by theory, it is believed that such evaporative cooling makes the cooling surfaces less prone to fouling, e.g., by reaction byproducts such as polymer and undesired oligomer, by catalyst residue and/or decomposition products, and/or even by desired oligomer product(s).

Also in Examples 11-15, and indeed in any of the methods according to the invention set forth herein, the synthesis reactor configuration may be set up to reduce, inhibit, and/or eliminate the mechanical agitation of the reactor and to approach plug flow of the liquid through the reactor system.

In some embodiments, the mechanical agitator may be eliminated if sufficient mixing energy is provided by the gas bubbles in the reactor. The ethylene trimerization process with evaporative cooling can be particularly well-suited to using only the gas bubbles for agitation. As the reaction proceeds, ethylene can react in the liquid phase. To maintain high reaction rates and selectivities, ethylene gas should typically transfer to the liquid phase to replenish the liquid-phase ethylene and should typically maintain an ethylene concentration close to the soluble limit. Also, as the reaction proceeds, heat can be generated, which generally can result in the vaporization of some of the liquids in the reactor, provided that the pressure, temperature, and choice of diluent are within an operating window where evaporative cooling is effective. The combination of a gaseous ethylene feed with the generation of gas bubbles by vaporization can provide effective mixing of the reactor, preferably keeping most, if not substantially all or completely all, insoluble catalyst components in suspension, and also preferably providing good gas-liquid mass transfer. One measure of the effectiveness of the agitation by gas bubbles can be by calculating the gas superficial velocity at the top surface of the reactor, where the gas disengages from the liquid. In some preferred embodiments, the gas superficial velocity can be from 2 cm/sec to 33 cm/sec, more preferably from 3 cm/sec to 25 cm/sec, most preferably from 4 cm/sec to 20 cm/sec.

In ethylene trimerization processes using organo-chrome catalysts, the catalyst activity can typically decline over time. In addition, small amounts of heavy byproducts are typically formed, e.g., decene isomers from the reaction of hexene with two ethylene molecules. Given these characteristics of the reaction, despite the previous observation that agitation can be desired in some embodiments, it should be recognized that catalyst utilization and product selectivies can generally be maximized by operating a reactor system that approaches plug flow behavior of the liquid phase.

Agitation within a single reactor can typically result in backmixing of the liquid contents of the reactor. Backmixing of the liquid is the opposite of plug flow behavior, where backmixing is avoided. A reactor system approaching plug flow behavior can be realized by staging the reactor system, e.g., by placing two or more backmixed reactors in series with each other. Such staging can be accomplished by placing baffles within a single reactor vessel, e.g., as shown in FIG. 19A, and/or by having multiple reactor vessels in series, as shown in FIG. 19B.

It should be recognized that there are many possible combinations of staging methods, selection of reaction diluents, temperatures, pressures, and the like, that can be made. FIGS. 19A and 19B are just two possible combinations showing representative features. In FIG. 19A, staging was achieved in a single vessel. In this embodiment, each stage can be equipped with a partial condenser and separator drum for returning the condensed liquid to the reactor stage for cooling. A common recycle blower can recirculate the uncondensed vapors back to the reaction system. In FIG. 19B, staging was achieved in two separate vessels. This embodiment represents one of the simplest overall reaction systems, as "drumless condensers" may be utilized, and no recirculation blower may be required. In one such embodiment, propane could be selected as a diluent at a pressure high enough to allow total condensation of the vapors leaving the reactors.

FIGS. 19A and 19B each show reactor systems with two stages. Addition of more stages can typically improve the approach to plug flow behavior, though adding to the overall cost of the plant. One example of a good compromise between the advantages of a closer approach to plug flow without adding too much cost can be to use three reaction stages.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law.

What is claimed is:

1. A method for preparing comonomer product from an olefin feed comprising:
    contacting said olefin, a preformed catalyst having an olefin selectivity of at least 90 mol % to a desired comonomer product, and a solvent and/or diluent as a reaction mixture in a reactor under reaction conditions sufficient to produce an effluent comprising said desired comonomer product, wherein said desired comonomer product is an alpha-olefin oligomer, and said solvent and/or diluent has a boiling point less than that of said desired comonomer product at a reactor pressure; and
    controlling the reaction temperature to between 80° C. and 90° C. by evaporatively cooling said reactor by vaporization of said solvent and/or diluent within the reactor by adjusting the reactor pressure from about 120 psia (8.44 kg/cm$^2$) to about 815 psia (57.3 kg/cm$^2$); wherein said reaction conditions yield a single pass conversion of said olefin of greater than 90% and the preformed catalyst comprises the combination of:
1) a ligand represented by the formula:

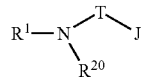

wherein:
    N is nitrogen;
    $R^1$ and $R^{20}$ are each independently selected from the group consisting of hydrogen, optionally substituted hydrocarbyl, heteroatom containing hydrocarbyl, and silyl, provided that $R^1$ or $R^{20}$ do not equal T-J, or alternately $R^1$ and $R^{20}$ are each independently a ring having from 4 to 8 atoms in the ring selected from the group consisting of substituted cycloalkyl, heterocycloalkyl, aryl, and heteroaryl;
    T is a bridging group, preferably represented by the formula -(T'R$^2$R$^3$)—, where T' is carbon or silicon, R$^2$ and R$^3$ are each independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, provided that two or more $R^2$ and/or $R^3$ groups may be joined together to form one or more optionally substituted ring systems having from 3 to 50 non-hydrogen atoms; and J is an optionally substituted six-membered heterocycle, containing at least one nitrogen atom as part of the ring, or J is an optionally substituted five-membered heterocycle, containing at least one nitrogen atom as part of the ring;

or a ligand represented by the formula:

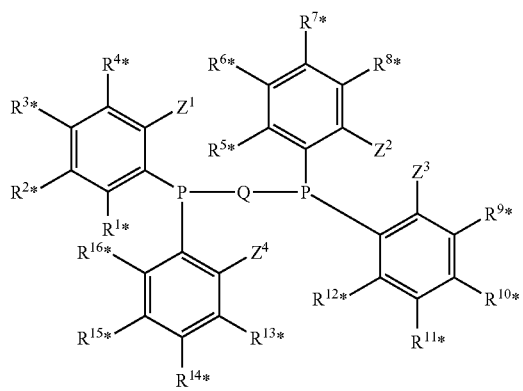

wherein:
P is phosphorus;
each of $R^{1*}, R^{2*}, R^{3*}, R^{4*}, R^{5*}, R^{6*}, R^{7*}, R^{8*}, R^{9*}, R^{10*}, R^{11*}, R^{12*}, R^{13*}, R^{14*}, R^{15*}$, and $R^{16*}$ is, independently, selected from the group consisting of hydrogen, halogen, optionally substituted hydrocarbyl, and optionally substituted heteroatom containing hydrocarbyl;
each of $Z^1, Z^2, Z^3$ or $Z^4$ is, independently, selected from the group consisting of hydrogen, a hydrocarbyl, alkoxy, aryloxy, alkylthio, arylthio, hydroxyl, mercapto, and amino; and
Q is a bridging group selected from the group consisting of optionally substituted hydrocarbyl having from 2 to 20 carbon atoms;

2) a metal precursor compound characterized by the general formula $Cr(L)_n$ where each L is independently selected from the group consisting of halide, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers, and combinations thereof, wherein two or more L groups may be combined in a ring structure having from 3 to 50 non-hydrogen atoms; and n is 1, 2, 3, 4, 5, or 6; and 3) optionally, one or more activators.

2. The method of claim 1, wherein the alpha-olefin oligomer is selected from the group consisting of 1-butene, 1-hexene, 1-octene, 1-decene, and mixtures thereof.

3. The method of claim 1, wherein said olefin feed is greater than about 99 wt % ethylene.

4. The method of claim 1, wherein the ligand of the preformed catalyst is represented by at least one of the following formulas:

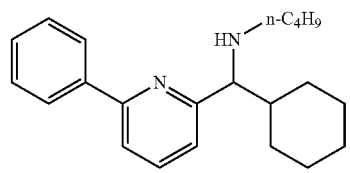

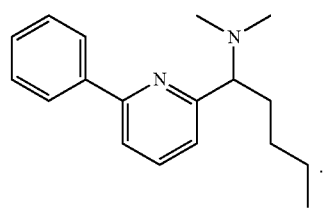

5. The method of claim 1, wherein said preformed catalyst comprises one or more activators.

6. The method of claim 1, wherein the solvent and/or diluent is selected from the group consisting of 1-butene, 1-hexene, 1-octene, toluene, propane, butane, isobutane, pentane, isopentane, and combinations thereof.

7. The method of claim 6, wherein said solvent and/or diluent is 1-hexene, isopentane, or the combination thereof.

8. The method of claim 1, wherein said reaction conditions comprise a reaction pressure from about 200 psi (8.44 kg/cm$^2$) to about 900 psi (63.3 kg/cm$^2$), and a reaction residence time from about 30 minutes to about 4 hours.

9. The method of claim 1, wherein the reactor comprises one or more bubble column reactors.

10. The method of claim 9, wherein at least one of the one or more bubble column reactors has more than one reaction stage.

11. The method of claim 9, wherein at least one of the one or more bubble column reactors comprises no mechanical agitation.

12. The method of claim 1, wherein a catalyst deactivator is added to said effluent stream exiting from said comonomer synthesis reactor.

13. The method of claim 12, wherein said catalyst deactivator comprises water, alcohol, or a combination thereof.

14. The method of claim 1, further comprising providing at least one gas/liquid phase separator downstream from said reactor.

15. The method of claim 14, wherein said downstream gas/liquid phase separator further comprise trays or packing in the vapor zone.

16. The method of claim 14, further comprising the step of adding olefin that is the same as said olefin feed to said downstream gas/liquid phase separator to strip out said desired comonomer product from said effluent.

17. The method of claim 14, further comprising providing a distillation column.

18. The method of claim 17, wherein said distillation column comprises less than three distillation columns.

19. The method of claim 17, wherein said distillation column separates unreacted olefin from the top and said desired comonomer product from the bottom.

20. The method of claim 19, wherein said distillation column further separates said solvent and/or diluent from the top.

21. The method of claim 17, wherein said distillation column comprises a divided wall type column.

22. The method of claim 17, wherein said distillation column separates said desired comonomer product from the bottom and said solvent and/or diluent from the top.

23. The method of claim 22, wherein the distillation column further separates unreacted olefin from the top.

24. The method of claim 14, wherein one or more of the following:
   (i) said reactor comprises two or more reactors in series;
   (ii) said gas/liquid phase separator comprises two or more gas/liquid phase separators in series; and
   (iii) said distillation column comprises two or more distillation columns in series.

25. The method of claim 14, wherein the reactor comprises two or more reactors in series, wherein the gas/liquid phase separator comprises two or more gas/liquid phase separators in series, or both.

26. The method of claim 1, further comprising purifying said effluent, which comprises filtering at least a portion of said effluent.

27. The method of claim 1, further comprising purifying said effluent, which comprises adsorbing catalyst from at least a portion of said effluent.

28. The method of claim 27, where said purifying step further comprises filtering at least a portion of said effluent.

29. The method of claim 1, wherein said effluent comprises a gas stream and a liquid stream.

30. The method of claim 29, wherein said gas stream comprises said desired comonomer product.

31. The method of claim 29, wherein said liquid stream comprises said desired comonomer product.

32. The method of claim 1, wherein the reactor comprises a combination of a comonomer synthesis reactor and a gas/liquid phase separator.

33. The method of claim 1, further comprising recycling to said reactor unreacted olefin and at least a portion of said solvent and/or diluent.

34. The method of claim 1, wherein said desired comonomer product is selected from the group consisting of 1-butene, 1-hexene, 1-octene, and 1-decene.

35. The method of claim 34, wherein said catalyst has an olefin selectivity of at least 95 mol % to said desired comonomer product.

36. The method of claim 34, wherein said catalyst has an olefin selectivity of at least 97 mol % to said desired comonomer product.

37. The method of claim 34, wherein said catalyst has an olefin selectivity of at least 98.5 mol % to said desired comonomer product.

38. The method of claim 1, wherein said catalyst has an olefin selectivity of at least 95 mol % to said desired comonomer product, and wherein said desired comonomer product is two olefins selected from the group consisting of 1-butene, 1-hexene, 1-octene, and 1-decene.

39. The method of claim 38, wherein said catalyst has an olefin selectivity of at least 98.5 mol % to said desired comonomer product.

40. The method of claim 1, wherein said catalyst has an olefin selectivity of at least 98.5 mol % to said desired comonomer product, and wherein said desired comonomer product is three olefins selected from the group consisting of 1-butene, 1-hexene, 1-octene, and 1-decene.

41. The method of claim 40, wherein said catalyst has an olefin selectivity of at least 99 mol % to said desired comonomer product.

42. The method of claim 1, wherein said catalyst has an olefin selectivity of at least 97.5 mol % to said desired comonomer product, and wherein the desired comonomer product is 1-hexene.

43. The method of claim 1, wherein said catalyst has an olefin selectivity of at least 98.5 mol % to said desired comonomer product, and wherein the desired comonomer product is 1-hexene.

44. The method of claim 1, further comprising storing the desired comonomer product prior to a subsequent use thereof.

45. The method of claim 1, wherein said vaporized solvent and/or diluent forms gas bubbles within said reactor, said bubbles acting to agitate the reaction mixture therein.

46. The method of claim 45, further comprising controlling vaporization of said solvent and/or effluent such that said gas bubbles disengage from said reaction mixture at a gas superficial velocity of from 2 cm/sec to 33 cm/sec.

* * * * *